US006001354A

United States Patent [19]
Pot et al.

[11] Patent Number: 6,001,354
[45] Date of Patent: Dec. 14, 1999

[54] GRB2 ASSOCIATING POLYPEPTIDES AND NUCLEIC ACIDS ENCODING THEREFOR

[75] Inventors: David A. Pot, San Francisco; Lewis T. Williams, Tiburon, both of Calif.; Anne Bennett Jefferson; Philip W. Majerus, both of University City, Mich.

[73] Assignees: Washington University, St. Louis, Mo.; The Regents of the University of California, Oakland, Calif.

[21] Appl. No.: 08/560,005

[22] Filed: Nov. 17, 1995

[51] Int. Cl.[6] .............................. A61K 38/51; C12Q 1/42; C12N 9/12; C07K 1/00

[52] U.S. Cl. .......................... 424/94.5; 435/21; 435/69.1; 435/194; 435/252.3; 435/320.1; 530/300; 530/350; 536/23.2

[58] Field of Search .......................... 424/94.5; 530/350; 536/23.2; 435/194, 69.1, 252.3, 320.1, 21

[56] References Cited

PUBLICATIONS

Motto et al. (1994). J. Biol. Chem. 269 (34):21608–613, Aug. 26, 1994.

Berridge and Irvine, "Inositol phosphates and cell signalling," *Nature*, 341:197–205 (1989).

Cantley et al., "Oncogenes and Signal Transduction," *Cell*, 74:1657 (1993).

Clark et al., "C. elegans cell–signalling gene sem–5 encodes a protein with SH2 and SH3 domains," *Nature*, 356:340–344 (1992).

Fantl et al., "Distinct Phosphotyrosines on a Growth Factor Receptor Bind to Specific Molecules that Mediate Different Signalling Pathways," *Cell*, 69:413 (1992).

Hawkins et al., "Platelet–derived growth factor stimulates synthesis of PtdIns $(3,4,5)P_3$ by activating a PtdIns $(4,5)$ $P_2$ 3–OH kinase," *Nature*, 358:157–159 (1992).

Hu et al., "Binding of NCK to SOS and Activation of ras–Dependent Gene Expression," *Mol. Cell. Biol.*, 15:1169–1174 (1995).

Janknecht et al., "Signal Integration at the c–fos Promoter," *Carcinogenesis*, 16(3):443–450 (1995).

Katzav et al., "vav, a Novel Human Oncogene Derived from a Locus Ubiquitously Expressed in Hematopoietic Cells," *EMBO J.*, 8:2283–2290 (1989).

Klippel et al., "The C–Terminal SH2 Domain of p85 Accounts for the High Affinity and Specificity of the Binding of Phosphatidylinositol 3–Kinase to Phosphorylated Platelet–Derived Growth Factor β Receptor," *Mol. Cell. Biol.* 12(4):1451–1459 (1992).

Maruta and Burgess, "Regulation of the Ras signalling Network," *Bioessays*, 16(7):489–496 (1994).

Piechaczyk et al., "c–fos Proto–Oncogene Regulation and Function," *Crit. Rev. Oncol./Hematol.*, 17(2):93–131(1994).

Pot et al., "Cloning and Characterization of a Novel Grb2 Associateing Protein Binding Through the SH3 Domains of Grb2; Similarity to Inositol Polyphosphate 5' Phosphatase," Conference on Signal Transduction of Normal and Tumor Cells, Banff, Alberta, Canada, Apr. 1–6, 1995.

Stephens et al., "Pathway of phosphatidylinositol(3,4, 5)–triphosphate synthesis in activated neutrophils," *Nature*, 351:33–39 (1991).

Stern et al., "The Human GRB2 and Drosophila Drk Genes Can Functionally Replace *the Caenorhabditis elegads* Cell Signalling Gene sem–5," *Mol. Biol. Cell*, 4:1175–1188 (1993).

Valius et al., "Phospholipase C–γl and Phosphatidylinositol 3 Kinase are the Downstream Mediators of the PDGF Receptor's Mitogenic Signal," *Cell*, 73:321 (1993).

York et al., "Isolation and heterologous expression of a cDNA encoding bovine inositol polyphosphate 1–phosphatase," *PNAS*, 87:9548–9552 (1990).

Damen, J.E., et al., "The 145–kDa protein induced to associate with Shc by multiple cytokines is an inositol tetraphosphate and phosphatidylinositol 3,4,5–triphosphate 5–phosphatase," *Proc. Natl. Acad. Sci.*, 93:1689–1693 (1996).

Hejna, J.A., et al., "Cloning and Characterization of a Human cDNA (INPPLI) Sharing Homology with Inositol Polyphosphate Phosphatases," *Genomics*, 29:285–287 (1995).

Jackson, S.P., et al., "Phosphatidylinositol 3,4,5–triphosphate is a substrate for the 75 kDA inositol polyphosphate 5–phosphatase and a novel 5–phosphatase which forms a complex with the p85/p110 form of phosphonositide 3–kinase," *The EMBO Journal*, 14(18):4490–4500 (1995).

Kavanaugh, W.M., et al., "Multiple forms of an inositol polyphosphate 5–phosphatase form signaling complexes with Shc and Grb2," (Research Paper) *Current Biology*, 6(4):438–445 (1996).

Laxminarayan, K.M., et al., "Characterization of cDNA Encoding the 43–kDA Membrane–associated Inositol–polyphosphate 5–Phosphatase," *J. Biol. Chem.*, 269(25):17305–17310, Issue of Jun. 24 (1994).

Norris, F.A., et al., "The Isolation and Characterization of cDNA Encoding Human and Rat Brain Inositol Polyphosphate 4–Phosphatase," *J. Biol. Chem*, 270(27):16128–16133, Issue of Jul. 7 (1995).

Odai, H. "The Proto–oncogene Product c–Cbl Becomes Tyrosine Phosphorylated by Stimulation with GM–CSF or Epo and Constitutivity Binds to the SH3 Domain of Grb2/ Ash in Human Hematopoietic Cells," *J. Biol. Chem.*, 270(18):10800–10805, Issue of May 5 (1995).

*Primary Examiner*—Ponnathapura Achutamurthy
*Assistant Examiner*—Tekchand Saidha
*Attorney, Agent, or Firm*—Townsend and Townsend and Crew LLP

[57] ABSTRACT

The present invention generally relates to novel GRB2 associating proteins and nucleic acids which encode these protein. In particular, these novel proteins possess inositol polyphosphate 5-phosphatase and phosphatidylinositol 5-phosphatase activities, important in growth factor mediated signal transduction. As such, the proteins, nucleic acids encoding the proteins, cells capable of expressing these nucleic acids and antibodies specific for these proteins will find a variety of uses in a variety of screening, therapeutic and other applications.

15 Claims, 27 Drawing Sheets

FIG. 10-1

```
CGCCCACTAATCCTTGATGTTCACCTTGTCCCCTGCCCCCAGAGAAGTCATCCGGACCCTCCCATCCCTGGAGTCTCTGCAGAGGTTATTTGACCA
              M  F  T  L  S  P  A  P  R  E  V  I  R  T  L  P  S  L  E  S  L  Q  R  L  F  D  Q
CATCAACATGGTGTCCAAGCTCAGCCAACTGACAAGCCTGTTGTCATCCATTGAAGACAAGGTCAAGGCCTTGCTGCACGAGGGTCCTGAGTCTCC
 I  N  M  V  S  K  L  S  Q  L  T  S  L  L  S  S  I  E  D  K  V  K  A  L  L  H  E  G  P  E  S  P
GGGGATTCCTCAGAAAATGCAGTTGAAAGTCGACGTTGAGTCTGGGAAACTGATCATTAAGAAGTCCAAGGATGGTTCTGAGGACAAGTTCTACAG
 G  I  P  Q  K  M  Q  L  K  V  D  V  E  S  G  K  L  I  I  K  K  S  K  D  G  S  E  D  K  F  Y  S
GATCTTGGTGGAAACAGAGAAGGAGAAGATCCTGCGGAAGGAATATGTTTTTGCTGACTCCAAAAAGAGAGAAGGCTTCTGCCAGCTCCTGCAGCA
 D  L  V  E  T  E  K  E  K  I  L  R  K  E  Y  V  F  A  D  S  K  K  R  E  G  F  C  Q  L  L  Q  Q
CGGCACCTGGAACATGGGTAACGCCCCCCCCAAGAAGATCACGTCTCCTGGTTCTCTCCAAGGGGAGGAAAGACGCGGGAGACTCTGCGGA
 G  T  W  N  M  G  N  A  P  P  K  K  I  T  S  W  F  L  S  K  G  Q  G  K  T  R  D  D  S  A  D
GAAGGAGTGGCTGGAGATCCTCAAACACTCCCTGCAAGAAATCACCAGTGTGACTTTTAAAACAGTGGCCATCCACACGCTCTGGAACATCCGCAT
 E  E  W  L  E  I  L  K  H  S  L  Q  E  I  T  S  V  T  F  K  T  V  A  I  H  T  L  W  N  I  R  I
CAACGTGAACACAGGCATTGCAAACACACTGGGGAACAAGGCCGTGGGTGTCAGTTTCATGTTCAATGGAACCTCCTTAGGGTTCGTCAACAG
 N  V  N  T  G  I  A  N  T  L  G  N  K  G  A  V  G  V  S  F  M  F  N  G  T  S  L  G  F  V  N  S
CATTCTCCGGTTCCTGGGGCTGGGAGATAAGAAGCTGAGTCCCTTTAACATCACTCACCGCTTCACGCACACTTCTTCTACACTTGGAGGAGAAGAAATCACGTT
 I  L  R  F  L  A  L  G  D  K  K  L  S  P  F  N  I  T  H  R  F  T  H  L  F  W  F  G  D  L  N  Y
GCAGCAGTACGCAGACCTCCTGTCCCACGACCAGCTGACCGAGTCTTCCTGGTGTGACCGAGTCCTCTGGAAGTCTTATCCCCTGGTGCACGTGTGTCAGTCTTA
    Q  Q  Y  A  D  L  L  S  H  D  Q  L  L  T  E  R  R  E  Q  K  V  F  L  H  F  E  E  E  I  T  F
GCAGAAAGCGACAGGGATGAAGTACAACTTGCCTTCCTGGTGTGACCGAGTCCTCTGGAAGTCTTATCCCCTGGTGCACGTGTGTCAGTCTTA
    Q  K  A  T  G  M  K  Y  N  L  P  S  W  C  D  R  V  L  W  K  S  Y  P  L  V  H  V  C  Q  S  Y
TGAGGCAGGAGAGTCACTTCCCAGTTTGTCTCTCAAGAACGGTCCCGGACTGTTGACAGCCAAGGACAGATTGAGTTTCTCAGGTGCTATGCCACATT
    E  A  G  V  T  S  Q  F  V  S  K  N  G  P  G  T  V  D  S  Q  G  Q  I  E  F  L  R  C  Y  A  T  L
GAGTTTGTCAAGAGTCAGGAAGGAGAATGAAGAAGGAGAGTCCGGGACTCTTCCAAAGCTGAAGCCCATT
    E  F  V  K  S  Q  E  G  E  N  E  E  G  S  E  G  E  L  V  K  F  G  E  T  L  P  K  L  K  P  I
CTCTGACAGCGACGAATCCTATGGCGAGGGCTGCATTGCCCTTCGGTTAGAGGCCACAGAAACGCAGCTGCCCATCTACACGCCTCTCACCCACCA
    S  F  V  K  S  Q  E  G  E  N  E  E  G  S  E  G  E  L  V  K  F  G  E  T  L  P  K  L  K  P  I
CTCTGACAGCGACGAATCCTATGGCGAGGGCTGCATTGCCCTTCGGTTAGAGGCCACAGAAACGCAGCTGCCCATCTACACGCCTCTCACCCACCA
    S  D  S  D  E  S  Y  G  E  G  C  I  A  L  R  L  E  A  T  E  T  Q  L  P  I  Y  T  P  L  T  H  H
```

FIG. 10-2

```
GCAGCTCTCCCCGGGCCTCCGTCCACGTCCTCAGGTTCCTGGTGAGGCCAATCC      150
 Q  L  S  P  G  L  R  P  R  P  Q  V  P  G  E  A  N  P       45
GCACCGGCCCTCCCTTATCCCCAGTCACCTTTGAGGTGAAGGCAGAGTCTCT        300
 H  R  P  S  L  I  P  P  V  T  F  E  V  K  A  E  S  L       95
CCACAAGAAATCCTGCAGCTCATTAAGTCACAGAAATTTCTGAATAAGTTGGT       450
 H  K  K  I  L  Q  L  I  K  S  Q  K  F  L  N  K  L  V      145
GATGAAGAACAAGCACTCAGAGAGCCAGCCCGACATGATCACCATCTTCAT         600
 M  K  N  K  H  S  E  Q  P  E  P  D  M  I  T  I  F  I      195
CTACATCCCCATGACATTTACGTGATCGGCACCCAAGAGGACCCCCTGAGTGA       750
 Y  I  P  H  D  I  Y  V  I  G  T  Q  E  D  P  L  S  E      245
CGTGGTGCTGGCCAAGCCTGAGCACGAGAACCGGATCAGCCACATCTGTACTGA      900
 V  V  L  A  K  P  E  H  E  N  R  I  S  H  I  C  T  D      295
CCACTTGACTTCAGGAAGTGAAAAGAAACTCAGGCGAAACTCAAAACTATATGAA     1050
 H  L  T  S  G  S  E  K  K  L  R  R  N  Q  N  Y  M  N      345
CCGTGTGGATCTGCCTACCTGGGAGGCAGAAACCATCATCCAGAAAATCAAGCA      1200
 R  V  D  L  P  T  W  E  A  E  T  I  I  Q  K  I  K  Q      395
TGCCCCAACCTACCGTTTTGAGAGACTGACTCGGGACAAATACGCCTACACCAA      1350
 A  P  T  Y  R  F  E  R  L  T  R  D  K  Y  A  Y  T  K      445
TGGCAGTACCAGCGACATCATGACGAGTGACCACAGCCCTGTCTTTGCCACATT      1500
 G  S  T  S  D  I  M  T  S  D  H  S  P  V  F  A  T  F      495
GAAGACCAAGTCCCAGACCAAATTCTACCTGGAGTTCCACTCGAGCTGCTTGGA     1650
 K  T  K  S  Q  T  K  F  Y  L  E  F  H  S  S  C  L  E      545
TATCTCTGACCCTGAGTACCTGCTAGACCAGCACATCCTCATCAGCATCAAGTC     1800
 I  S  D  P  E  Y  L  L  D  Q  H  I  L  I  S  I  K  S      595
TGGGGAGTTGACAGGCCACTTCCAGGGGGAGATCAAGCTGCAGACCTCTCAGGG     1950
 G  E  L  T  G  H  F  Q  G  E  I  K  L  Q  T  S  Q  G      645
```

```
GAAGCAGTGGGAAGTCACTAGCAGGGCCCCTCCGTGCAGTGGCTTCCAGCATCAC        2100
 K  Q  W  E  V  T  S  R  A  P  P  C  S  G  S  S  I  T          695
AGCCTGGGAGCTACGACCAGCCGCCAAGGAACGCGCCCCGCTGGGGCCCTGCAGGGG       2250
 A  W  S  Y  D  Q  P  P  K  D  S  P  L  G  P  C  R  G          745
GTCAAGGCCCAGTGACCTGGGGAAGAACGCAGGGGACACGCTGCCTCAGGAGGA          2400
 S  R  P  S  D  L  G  K  N  A  G  D  T  L  P  Q  E  D          795
CAAAATGCCGCGGAAGGAACCCCCGCCCTGCCCGGAACCCGGCATCTTGTCGCC          2550
 K  M  P  R  K  E  P  P  P  C  P  E  P  G  I  L  S  P          845
CTCTGCCGAGGGCAGGGCGCGGCGGGGGACAAGAGACCAAGGAAGCCCAAGAC           2700
 S  A  E  G  R  A  A  G  G  D  K  S  Q >G  K  P  K  T          895
GCCGGCCGCTGCCAGTCGAAGAGCTCGGAGCTGCACCTCCAGCACTCCAAGGG           2850
 P  P  L  P  V  K  S  P  A  V  L  H  Q  H  S  K  G             945
AAGCCCTCAGTGAGCTGCCACTGAGTCGGGAGCCCAGAGGAACGGGCGTGAAGCC         3000
976
CCACAGAGTTCACTGCCTGCCTGTGAGACTTAGCACCAAGTGCTGAGGCTGGAAGAAA      3150
GGAACTGCAGCCGCCGATTTGAGGGTGGAGATATAGATAATAATATTAATAA            3300
AGGCTCTAGCACCTAAAAACCACGTGCCCAAACCACCAGTTTAAAACGGTGTGT          3450
GGGTACAAGAAGCCTGTTCTGTCCAGCTTGACACAAGCTGCTTTAGCTAA              3600
CCAGTGGAGAGATCTGGCCTAGGCCTCCAAGGCCTGTGCCAG                      3750
GCTGTTGCTCCGAAAGCCGTGCTCTCCAGCCTGCTGCCAGGGAGGGTGGGCC            3900
TGTCTTTCCTTATGTTGCTTTTCAACATAGCAGAATTAATGTAGGGAGCTAAA           4050
C   4147
```

FIG. 11-A

```
celegptase    .                                                                          0
ysc5ptase     . MRLFIGRRSR  SIVISSNNYC  LSFQRLRSIP  GASSQQRQLS  KTPSVTIKSY  PDTDLSSDSN   60
51c           .                                                                          0
ga5ptase      .                                                                          0
5ptaseii      .                                                                          0
ocrl          .                                                                          0
arab5ptase    .                                                                          0
h5ptase43     .                                                                          0
Consensus     .                                                                          0 celegptase    .                                                                          0
ysc5ptase     . YLEVKSCIFN  GLLGLVCLNG  DIYVAVISGV  QNVGFPRWKL  IDHQVRPSES  IYKVLDVDFY  120
51c           .                                                                          0
ga5ptase      .                                                                          0
5ptaseii      .                                                                          0
ocrl          .                                                                          0
arab5ptase    .                                                                          0
h5ptase43     .                                                                          0
Consensus     .                                                                          0
```

FIG. 11-B

| | | | | | | | | | | |
|---|---|---|---|---|---|---|---|---|---|---|
| celegptase | . . . . . . . . | . . . . . . . . | . . . . . . . . | . . . . . . . . | . . . . . . . . | . . . . . . . . | . . . . . . . . | . . . . . . . . | . . . . . . . . | 0 |
| ysc5ptase | . SLENDVFDYL | . LCERSEQNYD | . KLIHEHPCGP | . LKKLFSDGTF | . YYSRDFDISN | . IVKNHGLSHN | | | | 180 |
| 51c | . . . . . . . . | . . . . . . . . | . . . . . . . . | . . . . . . . . | . . . . . . . . | . MCTRIAFCL | | | | 9 |
| ga5ptase | . . . . . . . . | . . . . . . . . | . . . . . . . . | . . . . . . . . | . . . . . . . . | . . . . . . . . | | | | 0 |
| 5ptaseii | . . . . . . . . | . . . . . . . . | . . . . . . . . | . . . . . . . . | . . . . . . . . | . . . . . . . . | | | | 0 |
| ocrl | . . . . . . . . | . . . . . . . . | . . . . . . . . | . . . . . . . . | . . . . . . . . | . . . . . . . . | | | | 0 |
| arab5ptase | . . . . . . . . | . . . . . . . . | . . . . . . . . | . . . . . . . . | . . . . . . . . | . . . . . . . . | | | | 0 |
| h5ptase43 | . . . . . . . . | . . . . . . . . | . . . . . . . . | . . . . . . . . | . . . . . . . . | . . . . . . . . | | | | 0 |
| Consensus | - - - - - - - - | - - - - - - - - | - - - - - - - - | - - - - - - - - | - - - - - - - - | - - - - - - - - | | | | 180 |

| | | | | | | | | | | |
|---|---|---|---|---|---|---|---|---|---|---|
| celegptase | . . . . . . . . | . SFIWNANLAS | . EVNWRSKIS | . NEERQLFANA | . GFLTFVIRGY | . QKTALEDGP | | | | 0 |
| ysc5ptase | . LEYTVDNQDL | . . . . . . . . | . PWVSSACTR | . SPTRALCAPC | . LELYRVESR | . THRMTGMPQM | | | | 240 |
| 51c | . MEKISWLCRP | . RRVCHCPASR | . . . . . . . . | . . . . . . . . | . . . . . . . . | . . . . . . . . | | | | 69 |
| ga5ptase | . . . . . . . . | . . . . . . . . | . . . . . . . . | . AESRAPCGDS | . SGGCVRSAGA | . SMDQSVAIQE | | | | 0 |
| 5ptaseii | . . . . . . . . | . . . . . . . . | . VTVPEPGA | . PRSRLPADGA | . RRGAVPQTTE | . SRGGWWGR | | | | 38 |
| ocrl | . MKFFV | . FKSFLSDCYF | . SLRDKSQLPA | . . . . . . . . | . . . . . . . . | . . . . . . . . | | | | 54 |
| arab5ptase | . . . . . . . . | . . . . . . . . | . . . . . . . . | . . . . . . . . | . . . . . . . . | . . . . . . . . | | | | 0 |
| h5ptase43 | . . . . . . . . | . . . . . . . . | . . . . . . . . | . . . . . . . . | . . . . . . . . | . . . . . . . . | | | | 0 |
| Consensus | - E - - - - - - | - - - L - - - - | - V - - S - - - | - ESRA - CA - A | - F - - VVS - GR | - V - - Q - - - | | | | 240 |

|  |  |  |  |  |  |  |  |  |  |
|---|---|---|---|---|---|---|---|---|---|
| celegptase |  |  |  |  |  |  |  |  | 398 |
| ysc5ptase | ALLPGPLELQ | PPPGTALGLW | PAPQLPSTP. | .HPGEHPGRP | GRGGSVPAGR | AGQRAGRGRH | | | 946 |
| 51c | PIKPSRSEIN | QQTPPTPTPR | PPLPVKSPAV | LHLQHSKGRD | YRDNTELPHH | GKHRPEEGPP | | | 1137 |
| ga5ptase |  |  |  |  |  |  |  |  | 967 |
| 5ptaseii |  |  |  |  |  |  |  |  | 942 |
| ocr1 |  |  |  |  |  |  |  |  | 968 |
| arab5ptase |  |  |  |  |  |  |  |  | 121 |
| h5ptase43 |  |  |  |  |  |  |  |  | 363 |
| Consensus | --P------- | ---------- | P---P----- | -H----GR-- | ------R--- | ----R----G | | | 1380 |

| | | |
|---|---|---|
| celegptase | | .398 |
| ysc5ptase | | .946 |
| 51c | ECEAAGHRLG AL1149 |
| ga5ptase | GPLGRTAMQ. | .976 |
| 5ptaseii | | .942 |
| ocr1 | | .968 |
| arab5ptase | | .121 |
| h5ptase43 | | .363 |
| Consensus | --E------- | --1392 |

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 4147 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 17..2944

(xi) SEQUENCE DESCRIPTION: SEQ ID NO:1:

```
CGCCCACTAA TCCTTG ATG TTC ACC TTG TCC CCT GCC CCC AGA GAA GTC                49
                  Met Phe Thr Leu Ser Pro Ala Pro Arg Glu Val
                   1               5                      10

ATC CGG ACC CTC CCA TCC CTG GAG TCT CTG CAG AGG TTA TTT GAC CAG              97
Ile Arg Thr Leu Pro Ser Leu Glu Ser Leu Gln Arg Leu Phe Asp Gln
            15                  20                  25

CAG CTC TCC CCG GGC CTC CGT CCA CGT CCT CAG GTT CCT GGT GAG GCC             145
Gln Leu Ser Pro Gly Leu Arg Pro Arg Pro Gln Val Pro Gly Glu Ala
                30                  35                  40

AAT CCC ATC AAC ATG GTG TCC AAG CTC AGC CAA CTG ACA AGC CTG TTG             193
Asn Pro Ile Asn Met Val Ser Lys Leu Ser Gln Leu Thr Ser Leu Leu
        45                  50                  55

TCA TCC ATT GAA GAC AAG GTC AAG GCC TTG CTG CAC GAG GGT CCT GAG             241
Ser Ser Ile Glu Asp Lys Val Lys Ala Leu Leu His Glu Gly Pro Glu
60                  65                  70                  75

TCT CCG CAC CGG CCC TCC CTT ATC CCT CCA GTC ACC TTT GAG GTG AAG             289
Ser Pro His Arg Pro Ser Leu Ile Pro Pro Val Thr Phe Glu Val Lys
                80                  85                  90

GCA GAG TCT CTG GGG ATT CCT CAG AAA ATG CAG CTC AAA GTC GAC GTT             337
Ala Glu Ser Leu Gly Ile Pro Gln Lys Met Gln Leu Lys Val Asp Val
            95                  100                 105

GAG TCT GGG AAA CTG ATC ATT AAG AAG TCC AAG GAT GGT TCT GAG GAC             385
Glu Ser Gly Lys Leu Ile Ile Lys Lys Ser Lys Asp Gly Ser Glu Asp
        110                 115                 120

AAG TTC TAC AGC CAC AAG AAA ATC CTG CAG CTC ATT AAG TCA CAG AAA             433
Lys Phe Tyr Ser His Lys Lys Ile Leu Gln Leu Ile Lys Ser Gln Lys
    125                 130                 135

TTT CTG AAT AAG TTG GTG ATC TTG GTG GAA ACA GAG AAG GAG AAG ATC             481
Phe Leu Asn Lys Leu Val Ile Leu Val Glu Thr Glu Lys Glu Lys Ile
140                 145                 150                 155

CTG CGG AAG GAA TAT GTT TTT GCT GAC TCC AAA AAG AGA GAA GGC TTC             529
Leu Arg Lys Glu Tyr Val Phe Ala Asp Ser Lys Lys Arg Glu Gly Phe
                160                 165                 170

TGC CAG CTC CTG CAG CAG ATG AAG AAC AAG CAC TCA GAG CAG CCG GAG             577
Cys Gln Leu Leu Gln Gln Met Lys Asn Lys His Ser Glu Gln Pro Glu
            175                 180                 185

CCC GAC ATG ATC ACC ATC TTC ATC GGC ACC TGG AAC ATG GGT AAC GCC             625
Pro Asp Met Ile Thr Ile Phe Ile Gly Thr Trp Asn Met Gly Asn Ala
        190                 195                 200

CCC CCT CCC AAG AAG ATC ACG TCC TGG TTT CTC TCC AAG GGG CAG GGA             673
Pro Pro Pro Lys Lys Ile Thr Ser Trp Phe Leu Ser Lys Gly Gln Gly
    205                 210                 215

AAG ACG CGG GAC GAC TCT GCG GAC TAC ATC CCC CAT GAC ATT TAC GTG             721
Lys Thr Arg Asp Asp Ser Ala Asp Tyr Ile Pro His Asp Ile Tyr Val
220                 225                 230                 235

ATC GGC ACC CAA GAG GAC CCC CTG AGT GAG AAG GAG TGG CTG GAG ATC             769
Ile Gly Thr Gln Glu Asp Pro Leu Ser Glu Lys Glu Trp Leu Glu Ile
                240                 245                 250

CTC AAA CAC TCC CTG CAA GAA ATC ACC AGT GTG ACT TTT AAA ACA GTC             817
Leu Lys His Ser Leu Gln Glu Ile Thr Ser Val Thr Phe Lys Thr Val
            255                 260                 265

GCC ATC CAC ACG CTC TGG AAC ATC CGC ATC GTG GTG CTG GCC AAG CCT             865
Ala Ile His Thr Leu Trp Asn Ile Arg Ile Val Val Leu Ala Lys Pro
        270                 275                 280

GAG CAC GAG AAC CGG ATC AGC CAC ATC TGT ACT GAC AAC GTG AAG ACA             913
Glu His Glu Asn Arg Ile Ser His Ile Cys Thr Asp Asn Val Lys Thr
    285                 290                 295

GGC ATT GCA AAC ACA CTG GGG AAC AAG GGA GCC GTG GGG GTG TCG TTC             961
Gly Ile Ala Asn Thr Leu Gly Asn Lys Gly Ala Val Gly Val Ser Phe
```

-continued

```
              300                 305                 310                 315
ATG TTC AAT GGA ACC TCC TTA GGG TTC GTC AAC AGC CAC TTG ACT TCA        1009
Met Phe Asn Gly Thr Ser Leu Gly Phe Val Asn Ser His Leu Thr Ser
                    320                 325                 330

GGA AGT GAA AAG AAA CTC AGG CGA AAC CAA AAC TAT ATG AAC ATT CTC        1057
Gly Ser Glu Lys Lys Leu Arg Arg Asn Gln Asn Tyr Met Asn Ile Leu
                335                 340                 345

CGG TTC CTG GCC CTG GGC GAC AAG AAG CTG AGT CCC TTT AAC ATC ACT        1105
Arg Phe Leu Ala Leu Gly Asp Lys Lys Leu Ser Pro Phe Asn Ile Thr
            350                 355                 360

CAC CGC TTC ACG CAC CTC TTC TGG TTT GGG GAT CTT AAC TAC CGT GTG        1153
His Arg Phe Thr His Leu Phe Trp Phe Gly Asp Leu Asn Tyr Arg Val
        365                 370                 375

GAT CTG CCT ACC TGG GAG GCA GAA ACC ATC ATC CAG AAA ATC AAG CAG        1201
Asp Leu Pro Thr Trp Glu Ala Glu Thr Ile Ile Gln Lys Ile Lys Gln
380                 385                 390                 395

CAG CAG TAC GCA GAC CTC CTG TCC CAC GAC CAG CTG CTC ACA GAG AGG        1249
Gln Gln Tyr Ala Asp Leu Leu Ser His Asp Gln Leu Leu Thr Glu Arg
                    400                 405                 410

AGG GAG CAG AAG GTC TTC CTA CAC TTC GAG GAG GAA GAA ATC ACG TTT        1297
Arg Glu Gln Lys Val Phe Leu His Phe Glu Glu Glu Glu Ile Thr Phe
                415                 420                 425

GCC CCA ACC TAC CGT TTT GAG AGA CTG ACT CGG GAC AAA TAC GCC TAC        1345
Ala Pro Thr Tyr Arg Phe Glu Arg Leu Thr Arg Asp Lys Tyr Ala Tyr
            430                 435                 440

ACC AAG CAG AAA GCG ACA GGG ATG AAG TAC AAC TTG CCT TCC TGG TGT        1393
Thr Lys Gln Lys Ala Thr Gly Met Lys Tyr Asn Leu Pro Ser Trp Cys
        445                 450                 455

GAC CGA GTC CTC TGG AAG TCT TAT CCC CTG GTG CAC GTG GTG TGT CAG        1441
Asp Arg Val Leu Trp Lys Ser Tyr Pro Leu Val His Val Val Cys Gln
460                 465                 470                 475

TCT TAT GGC AGT ACC AGC GAC ATC ATG ACG AGT GAC CAC AGC CCT GTC        1489
Ser Tyr Gly Ser Thr Ser Asp Ile Met Thr Ser Asp His Ser Pro Val
                    480                 485                 490

TTT GCC ACA TTT GAG GCA GGA GTC ACT TCC CAG TTT GTC TCC AAG AAC        1537
Phe Ala Thr Phe Glu Ala Gly Val Thr Ser Gln Phe Val Ser Lys Asn
                495                 500                 505

GGT CCC GGG ACT GTT GAC AGC CAA GGA CAG ATT GAG TTT CTC AGG TGC        1585
Gly Pro Gly Thr Val Asp Ser Gln Gly Gln Ile Glu Phe Leu Arg Cys
            510                 515                 520

TAT GCC ACA TTG AAG ACC AAG TCC CAG ACC AAA TTC TAC CTG GAG TTC        1633
Tyr Ala Thr Leu Lys Thr Lys Ser Gln Thr Lys Phe Tyr Leu Glu Phe
        525                 530                 535

CAC TCG AGC TGC TTG GAG AGT TTT GTC AAG AGT CAG GAA GGA GAA AAT        1681
His Ser Ser Cys Leu Glu Ser Phe Val Lys Ser Gln Glu Gly Glu Asn
540                 545                 550                 555

GAA GAA GGA AGT GAG GGG GAG CTG GTG GTG AAG TTT GGT GAG ACT CTT        1729
Glu Glu Gly Ser Glu Gly Glu Leu Val Val Lys Phe Gly Glu Thr Leu
                    560                 565                 570

CCA AAG CTG AAG CCC ATT ATC TCT GAC CCT GAG TAC CTG CTA GAC CAG        1777
Pro Lys Leu Lys Pro Ile Ile Ser Asp Pro Glu Tyr Leu Leu Asp Gln
                575                 580                 585

CAC ATC CTC ATC AGC ATC AAG TCC TCT GAC AGC GAC GAA TCC TAT GGC        1825
His Ile Leu Ile Ser Ile Lys Ser Ser Asp Ser Asp Glu Ser Tyr Gly
            590                 595                 600

GAG GGC TGC ATT GCC CTT CGG TTA GAG GCC ACA GAA ACG CAG CTG CCC        1873
Glu Gly Cys Ile Ala Leu Arg Leu Glu Ala Thr Glu Thr Gln Leu Pro
        605                 610                 615

ATC TAC ACG CCT CTC ACC CAC CAT GGG GAG TTG ACA GGC CAC TTC CAG        1921
Ile Tyr Thr Pro Leu Thr His His Gly Glu Leu Thr Gly His Phe Gln
```

-continued

```
           620                 625                 630                 635
GGG GAG ATC AAG CTG CAG ACC TCT CAG GGC AAG ACG AGG GAG AAG CTC    1969
Gly Glu Ile Lys Leu Gln Thr Ser Gln Gly Lys Thr Arg Glu Lys Leu
                    640                 645                 650

TAT GAC TTT GTG AAG ACG GAG CGT GAT GAA TCC AGT GGG CCA AAG ACC    2017
Tyr Asp Phe Val Lys Thr Glu Arg Asp Glu Ser Ser Gly Pro Lys Thr
                655                 660                 665

CTG AAG AGC CTC ACC AGC CAC GAC CCC ATG AAG CAG TGG GAA GTC ACT    2065
Leu Lys Ser Leu Thr Ser His Asp Pro Met Lys Gln Trp Glu Val Thr
            670                 675                 680

AGC AGG GCC CCT CCG TGC AGT GGC TCC AGC ATC ACT GAA ATC ATC AAC    2113
Ser Arg Ala Pro Pro Cys Ser Gly Ser Ser Ile Thr Glu Ile Ile Asn
        685                 690                 695

CCC AAC TAC ATG GGA GTG GGC CCC TTT GGG CCA CCA ATG CCC CTG CAC    2161
Pro Asn Tyr Met Gly Val Gly Pro Phe Gly Pro Pro Met Pro Leu His
700                 705                 710                 715

GTG AAG CAG ACC TTG TCC CCT GAC CAG CAG CCC ACA GCC TGG AGC TAC    2209
Val Lys Gln Thr Leu Ser Pro Asp Gln Gln Pro Thr Ala Trp Ser Tyr
                720                 725                 730

GAC CAG CCG CCC AAG GAC TCC CCG CTG GGG CCC TGC AGG GGA GAA AGT    2257
Asp Gln Pro Pro Lys Asp Ser Pro Leu Gly Pro Cys Arg Gly Glu Ser
                735                 740                 745

CCT CCG ACA CCT CCC GGC CAG CCG CCC ATA TCA CCC AAG AAG TTT TTA    2305
Pro Pro Thr Pro Pro Gly Gln Pro Pro Ile Ser Pro Lys Lys Phe Leu
            750                 755                 760

CCC TCA ACA GCA AAC CGG GGT CTC CCT CCC AGG ACA CAG GAG TCA AGG    2353
Pro Ser Thr Ala Asn Arg Gly Leu Pro Pro Arg Thr Gln Glu Ser Arg
        765                 770                 775

CCC AGT GAC CTG GGG AAG AAC GCA GGG GAC ACG CTG CCT CAG GAG GAC    2401
Pro Ser Asp Leu Gly Lys Asn Ala Gly Asp Thr Leu Pro Gln Glu Asp
780                 785                 790                 795

CTG CCG CTG ACG AAG CCC GAG ATG TTT GAG AAC CCC CTG TAT GGG TCC    2449
Leu Pro Leu Thr Lys Pro Glu Met Phe Glu Asn Pro Leu Tyr Gly Ser
                800                 805                 810

CTG AGT TCC TTC CCT AAG CCT GCT CCC AGG AAG GAC CAG GAA TCC CCC    2497
Leu Ser Ser Phe Pro Lys Pro Ala Pro Arg Lys Asp Gln Glu Ser Pro
                815                 820                 825

AAA ATG CCG CGG AAG GAA CCC CCG CCC TGC CCG GAA CCC GGC ATC TTG    2545
Lys Met Pro Arg Lys Glu Pro Pro Pro Cys Pro Glu Pro Gly Ile Leu
            830                 835                 840

TCG CCC AGC ATC GTG CTC ACC AAA GCC CAG GAG GCT GAT CGC GGC GAG    2593
Ser Pro Ser Ile Val Leu Thr Lys Ala Gln Glu Ala Asp Arg Gly Glu
        845                 850                 855

GGG CCC GGC AAG CAG GTG CCC GCG CCC CGG CTG CGC TCC TTC ACG TGC    2641
Gly Pro Gly Lys Gln Val Pro Ala Pro Arg Leu Arg Ser Phe Thr Cys
860                 865                 870                 875

TCA TCC TCT GCC GAG GGC AGG GCG GCC GGC GGG GAC AAG AGC CAA GGG    2689
Ser Ser Ser Ala Glu Gly Arg Ala Ala Gly Gly Asp Lys Ser Gln Gly
                880                 885                 890

AAG CCC AAG ACC CCG GTC AGC TCC CAG GCC CCG GTG CCG GCC AAG AGG    2737
Lys Pro Lys Thr Pro Val Ser Ser Gln Ala Pro Val Pro Ala Lys Arg
                895                 900                 905

CCC ATC AAG CCT TCC AGA TCG GAA ATC AAC CAG CAG ACC CCG CCC ACC    2785
Pro Ile Lys Pro Ser Arg Ser Glu Ile Asn Gln Gln Thr Pro Pro Thr
            910                 915                 920

CCG ACG CCG CGG CCG CCG CTG CCA GTC AAG AGC CCG GCG GTG CTG CAC    2833
Pro Thr Pro Arg Pro Pro Leu Pro Val Lys Ser Pro Ala Val Leu His
        925                 930                 935

CTC CAG CAC TCC AAG GGC CGC GAC TAC CGC GAC AAC ACC GAG CTC CCG    2881
Leu Gln His Ser Lys Gly Arg Asp Tyr Arg Asp Asn Thr Glu Leu Pro
```

-continued

```
        940                 945                 950                 955
CAT CAC GGC AAG CAC CGG CCG GAG GAG GGG CCA CCA GGG CCT CTA GGC         2929
His His Gly Lys His Arg Pro Glu Glu Gly Pro Pro Gly Pro Leu Gly
                        960                 965                 970

AGG ACT GCC ATG CAG TGAAGC CCTCAGTGAG CTGCCACTGA GTCGGGA               2977
Arg Thr Ala Met Gln
            975

GCCCAGAGGA ACGGCGTGAA GCCACTGGAC CCTCTCCCGG GACCTCCTGC TGGCTCCTCC      3037

TGCCCAGCTT CCTATGCAAG GCTTTGTGTT TTCAGGAAAG GGCCTAGCTT CTGTGTGGCC      3097

CACAGAGTTC ACTGCCTGTG AGACTTAGCA CCAAGTGCTG AGGCTGGAAG AAAAACGCAC      3157

ACCAGACGGG CAACAAACAG TCTGGGTCCC CAGCTCGCTC TTGGTACTTG GGACCCCAGT      3217

GCCTCGTTGA GGGCGCCATT CTGAAGAAAG GAACTGCAGC GCCGATTTGA GGGTGGAGAT      3277

ATAGATAATA ATAATATTAA TAATAATAAT GGCCACATGG ATCGAACACT CATGATGTGC      3337

CAAATGCTGT GCTAAGTGCT TTACGAACAT TCGTCATATC AGGATGACCT CGAGAGCTGA      3397

GGCTCTAGCA CCTAAAACCA CGTGCCCAAA CCCACCAGTT TAAAACGGTG TGTGTTCGGA      3457

GGGGTGAAAG CATTAAGAAG CCCAGTGCCC TCCTGGAGTG AGACAAGGGC TCGGCCTTAA      3517

GGAGCTGAAG AGTCTGGGTA GCTTGTTTAG GGTACAAGAA GCCTGTTCTG TCCAGCTTCA      3577

GTGACACAAG CTGCTTTAGC TAAAGTCCCG CGGGTTCCGG CATGGCTAGG CTGAGAGCAG      3637

GGATCTACCT GGCTTCTCAG TTCTTTGGTT GGAAGGAGCA GGAAATCAGC TCCTATTCTC      3697

CAGTGGAGAG ATCTGGCCTC AGCTTGGGCT AGAGATGCCA AGGCCTGTGC CAGGTTCCCT      3757

GTGCCCTCCT CGAGGTGGGC AGCCATCACC AGCCACAGTT AAGCCAAGCC CCCAACATG       3817

TATTCCATCG TGCTGGTAGA AGAGTCTTTG CTGTTGCTCC CGAAAGCCGT GCTCTCCAGC      3877

CTGGCTGCCA GGGAGGGTGG GCCTCTTGGT TCCAGGCTCT TGAAATAGTG CAGCCTTTTC      3937

TTCCTATCTC TGTGGCTTTC AGCTCTGCTT CCTTGGTTAT TAGGAGAATA GATGGGTGAT      3997

GTCTTTCCTT ATGTTGCTTT TTCAACATAG CAGAATTAAT GTAGGGAGCT AAATCCAGTG      4057

GTGTGTGTGA ATGCAGAAGG GAATGCACCC CACATTCCCA TGATGGAAGT CTGCGTAACC     4117

AATAAATTGT GCCTTTCTCA CTCAAAACCC                                       4147
```

(2) INFORMATION FOR SEQ ID NO:2:

(i) SEQUENCE CHARACTERISTICS:
        (A) LENGTH: 976 amino acids
        (B) TYPE: amino acid
        (D) TOPOLOGY: linear (ii) MOLECULE TYPE: protein (xi) SEQUENCE DESCRIPTION: SEQ ID NO:2:

```
Met Phe Thr Leu Ser Pro Ala Pro Arg Glu Val Ile Arg Thr Leu Pro
 1               5                  10                  15

Ser Leu Glu Ser Leu Gln Arg Leu Phe Asp Gln Leu Ser Pro Gly
            20                  25                  30

Leu Arg Pro Arg Pro Gln Val Pro Gly Glu Ala Asn Pro Ile Asn Met
        35                  40                  45

Val Ser Lys Leu Ser Gln Leu Thr Ser Leu Leu Ser Ser Ile Glu Asp
    50                  55                  60

Lys Val Lys Ala Leu Leu His Glu Gly Pro Glu Ser Pro His Arg Pro
65                  70                  75                  80

Ser Leu Ile Pro Pro Val Thr Phe Glu Val Lys Ala Glu Ser Leu Gly
                85                  90                  95
```

-continued

```
Ile Pro Gln Lys Met Gln Leu Lys Val Asp Val Glu Ser Gly Lys Leu
             100                 105                 110
Ile Ile Lys Lys Ser Lys Asp Gly Ser Glu Asp Lys Phe Tyr Ser His
             115                 120                 125
Lys Lys Ile Leu Gln Leu Ile Lys Ser Gln Lys Phe Leu Asn Lys Leu
             130                 135                 140
Val Ile Leu Val Glu Thr Glu Lys Lys Ile Leu Arg Lys Glu Tyr
145                  150                 155                 160
Val Phe Ala Asp Ser Lys Lys Arg Glu Gly Phe Cys Gln Leu Leu Gln
                 165                 170                 175
Gln Met Lys Asn Lys His Ser Glu Gln Pro Glu Pro Asp Met Ile Thr
             180                 185                 190
Ile Phe Ile Gly Thr Trp Asn Met Gly Asn Ala Pro Pro Lys Lys
             195                 200                 205
Ile Thr Ser Trp Phe Leu Ser Lys Gly Gln Gly Lys Thr Arg Asp Asp
             210                 215                 220
Ser Ala Asp Tyr Ile Pro His Asp Ile Tyr Val Ile Gly Thr Gln Glu
225                  230                 235                 240
Asp Pro Leu Ser Glu Lys Glu Trp Leu Glu Ile Leu Lys His Ser Leu
                 245                 250                 255
Gln Glu Ile Thr Ser Val Thr Phe Lys Thr Val Ala Ile His Thr Leu
             260                 265                 270
Trp Asn Ile Arg Ile Val Val Leu Ala Lys Pro Glu His Glu Asn Arg
             275                 280                 285
Ile Ser His Ile Cys Thr Asp Asn Val Lys Thr Gly Ile Ala Asn Thr
             290                 295                 300
Leu Gly Asn Lys Gly Ala Val Gly Val Ser Phe Met Phe Asn Gly Thr
305                  310                 315                 320
Ser Leu Gly Phe Val Asn Ser His Leu Thr Ser Gly Ser Glu Lys Lys
                 325                 330                 335
Leu Arg Arg Asn Gln Asn Tyr Met Asn Ile Leu Arg Phe Leu Ala Leu
             340                 345                 350
Gly Asp Lys Lys Leu Ser Pro Phe Asn Ile Thr His Arg Phe Thr His
             355                 360                 365
Leu Phe Trp Phe Gly Asp Leu Asn Tyr Arg Val Asp Leu Pro Thr Trp
             370                 375                 380
Glu Ala Glu Thr Ile Ile Gln Lys Ile Lys Gln Gln Gln Tyr Ala Asp
385                  390                 395                 400
Leu Leu Ser His Asp Gln Leu Leu Thr Glu Arg Arg Glu Gln Lys Val
                 405                 410                 415
Phe Leu His Phe Glu Glu Glu Ile Thr Phe Ala Pro Thr Tyr Arg
             420                 425                 430
Phe Glu Arg Leu Thr Arg Asp Lys Tyr Ala Tyr Thr Lys Gln Lys Ala
             435                 440                 445
Thr Gly Met Lys Tyr Asn Leu Pro Ser Trp Cys Asp Arg Val Leu Trp
             450                 455                 460
Lys Ser Tyr Pro Leu Val His Val Cys Gln Ser Tyr Gly Ser Thr
465                  470                 475                 480
Ser Asp Ile Met Thr Ser Asp His Ser Pro Val Phe Ala Thr Phe Glu
                 485                 490                 495
Ala Gly Val Thr Ser Gln Phe Val Ser Lys Asn Gly Pro Gly Thr Val
             500                 505                 510
Asp Ser Gln Gly Gln Ile Glu Phe Leu Arg Cys Tyr Ala Thr Leu Lys
             515                 520                 525
```

-continued

Thr Lys Ser Gln Thr Lys Phe Tyr Leu Glu Phe His Ser Ser Cys Leu
        530                 535                 540

Glu Ser Phe Val Lys Ser Gln Glu Gly Glu Asn Glu Glu Gly Ser Glu
545                 550                 555                 560

Gly Glu Leu Val Val Lys Phe Gly Thr Leu Pro Lys Leu Lys Pro
                565                 570                 575

Ile Ile Ser Asp Pro Glu Tyr Leu Leu Asp Gln His Ile Leu Ile Ser
                580                 585                 590

Ile Lys Ser Ser Asp Ser Asp Glu Ser Tyr Gly Glu Gly Cys Ile Ala
            595                 600                 605

Leu Arg Leu Glu Ala Thr Glu Thr Gln Leu Pro Ile Tyr Thr Pro Leu
        610                 615                 620

Thr His His Gly Glu Leu Thr Gly His Phe Gln Gly Glu Ile Lys Leu
625                 630                 635                 640

Gln Thr Ser Gln Gly Lys Thr Arg Glu Lys Leu Tyr Asp Phe Val Lys
                645                 650                 655

Thr Glu Arg Asp Glu Ser Ser Gly Pro Lys Thr Leu Lys Ser Leu Thr
                660                 665                 670

Ser His Asp Pro Met Lys Gln Trp Glu Val Thr Ser Arg Ala Pro Pro
        675                 680                 685

Cys Ser Gly Ser Ser Ile Thr Glu Ile Ile Asn Pro Asn Tyr Met Gly
        690                 695                 700

Val Gly Pro Phe Gly Pro Pro Met Pro Leu His Val Lys Gln Thr Leu
705                 710                 715                 720

Ser Pro Asp Gln Gln Pro Thr Ala Trp Ser Tyr Asp Gln Pro Pro Lys
                725                 730                 735

Asp Ser Pro Leu Gly Pro Cys Arg Gly Glu Ser Pro Thr Pro Pro
                740                 745                 750

Gly Gln Pro Pro Ile Ser Pro Lys Lys Phe Leu Pro Ser Thr Ala Asn
                755                 760                 765

Arg Gly Leu Pro Pro Arg Thr Gln Glu Ser Arg Pro Ser Asp Leu Gly
        770                 775                 780

Lys Asn Ala Gly Asp Thr Leu Pro Gln Glu Asp Leu Pro Leu Thr Lys
785                 790                 795                 800

Pro Glu Met Phe Glu Asn Pro Leu Tyr Gly Ser Leu Ser Ser Phe Pro
                805                 810                 815

Lys Pro Ala Pro Arg Lys Asp Gln Glu Ser Pro Lys Met Pro Arg Lys
            820                 825                 830

Glu Pro Pro Pro Cys Pro Glu Pro Gly Ile Leu Ser Pro Ser Ile Val
        835                 840                 845

Leu Thr Lys Ala Gln Glu Ala Asp Arg Gly Glu Gly Pro Gly Lys Gln
850                 855                 860

Val Pro Ala Pro Arg Leu Arg Ser Phe Thr Cys Ser Ser Ser Ala Glu
865                 870                 875                 880

Gly Arg Ala Ala Gly Gly Asp Lys Ser Gln Gly Lys Pro Lys Thr Pro
                885                 890                 895

Val Ser Ser Gln Ala Pro Val Pro Ala Lys Arg Pro Ile Lys Pro Ser
            900                 905                 910

Arg Ser Glu Ile Asn Gln Gln Thr Pro Pro Thr Pro Thr Pro Arg Pro
        915                 920                 925

Pro Leu Pro Val Lys Ser Pro Ala Val Leu His Leu Gln His Ser Lys
        930                 935                 940

Gly Arg Asp Tyr Arg Asp Asn Thr Glu Leu Pro His His Gly Lys His

```
                945            950            955           960
       Arg Pro Glu Glu Gly Pro Pro Gly Pro Leu Gly Arg Thr Ala Met Gln
                       965            970           975
```

(2) INFORMATION FOR SEQ ID NO:3:

(i) SEQUENCE CHARACTERISTICS:
        (A) LENGTH: 398 amino acids
        (B) TYPE: amino acid
        (D) TOPOLOGY: linear (ii) MOLECULE TYPE: protein (ix) FEATURE:
        (A) NAME/KEY: Region
        (B) LOCATION: 1..398
        (D) OTHER INFORMATION: /note= "celegptase"

(xi) SEQUENCE DESCRIPTION: SEQ ID NO:3:

```
Met Asp Thr Lys Ile Thr Ile Phe Thr Tyr Asn Leu Ala Met Lys Ala
 1               5                  10                  15

Ser Asp Ser Glu Ala Val His Lys Asn Leu Asn Gly Met Ile Asp Asp
             20                  25                  30

His Thr His Leu Val Ala Ile Gly Leu Gln Glu Val Ala His Ser Glu
         35                  40                  45

Thr Ile Gly Gly Ala Val Leu Thr Trp Ala Thr Thr Ile Ala Ser Trp
     50                  55                  60

Met Asn Thr Asn Gly Arg Met Val Leu Leu Ala Lys Thr Phe Gln Ala
65                  70                  75                  80

Thr Asn Gln Val Leu Ile Phe Gly Arg Lys Gln Leu Ile Gly Gln Ile
                 85                  90                  95

Lys Arg Ile Asp Tyr Arg Phe Gln Arg Asn Thr Met Gly Gly Leu Thr
            100                 105                 110

Gly His Lys Gly Ser Ile Gly Val Arg Leu Gln Leu Ala Ser Pro Tyr
        115                 120                 125

Ser Ile Val Pro Val Asp Ser His Phe Ile His Gly Pro Glu Asn Tyr
    130                 135                 140

Gly Lys Arg Val Glu Gln Tyr His Thr Asn Arg Asn Cys Ser Phe Pro
145                 150                 155                 160

Glu Asp Lys Ser Val Arg Ala Ala Phe Trp Phe Gly Asp Asp Asn Phe
                165                 170                 175

Arg Val Glu Glu Asp Val Asn Thr Val Ile Arg Lys Ile Lys Asn Gly
            180                 185                 190

Thr His Leu Glu Leu Leu Asp Thr Arg Glu Gln Leu Lys Arg Ala Leu
        195                 200                 205

Val Glu Arg Asp Ala Phe Ile Gly Phe His Glu Gln Pro Val Thr Phe
    210                 215                 220

Glu Pro Thr Tyr Arg Val Thr Val Gly Thr Thr Glu Gln Asp Gly Lys
225                 230                 235                 240

Arg Val Pro Ser Trp Thr Asp Arg Ile Leu Tyr Lys Gly Asp Gly Ile
                245                 250                 255

Thr Gly Leu Ser Tyr Thr Asn Asn Lys Lys Ala Val Ala Ser Asp His
            260                 265                 270

Leu Pro Val Val Ala Met Phe Arg Met Thr Ala Pro Ala Pro Lys
        275                 280                 285

Pro Gln Trp Glu Val Ile Phe Glu His Leu Pro Thr Trp Tyr Thr Ser
    290                 295                 300

Ile Pro Leu Val Gly Arg Phe Gln Val Asn Glu Leu Tyr Tyr Lys Glu
```

-continued

```
      305                 310                 315                 320

Asn Gly Ser Tyr Arg Asp Trp Ile Gly Val Phe Pro Ser Ser Ile Asn
                    325                 330                 335

Asp Cys Thr Thr Ala Thr Asn Trp Ile Tyr Ala Ala Thr Cys Phe Glu
                    340                 345                 350

Gln Val Ile Glu Gly Ser Lys Phe Leu Ala Cys Glu Phe Asn Asn Ile
                    355                 360                 365

Pro Ala Gly Asn Tyr Arg Leu Gly Tyr Phe Ser Cys His Leu His Cys
                    370                 375                 380

Leu Val Gly Leu Ser Lys Val Phe Gln Ile Val Glu Gln Pro
385                 390                 395
```

(2) INFORMATION FOR SEQ ID NO:4:

(i) SEQUENCE CHARACTERISTICS:
        (A) LENGTH: 946 amino acids
        (B) TYPE: amino acid
        (D) TOPOLOGY: linear (ii) MOLECULE TYPE: protein (ix) FEATURE:
        (A) NAME/KEY: Region
        (B) LOCATION: 1..946
        (D) OTHER INFORMATION: /note= "ysc5ptase"

(xi) SEQUENCE DESCRIPTION: SEQ ID NO:4:

```
Met Arg Leu Phe Ile Gly Arg Arg Ser Arg Ser Ile Val Ile Ser Ser
1               5                   10                  15

Asn Asn Tyr Cys Leu Ser Phe Gln Arg Leu Arg Ser Ile Pro Gly Ala
                20                  25                  30

Ser Ser Gln Gln Arg Gln Leu Ser Lys Thr Pro Ser Val Thr Ile Lys
                35                  40                  45

Ser Tyr Pro Asp Thr Asp Leu Ser Ser Asp Ser Asn Tyr Leu Glu Val
            50                  55                  60

Lys Ser Cys Ile Phe Asn Gly Leu Leu Gly Leu Val Cys Leu Asn Gly
65                  70                  75                  80

Asp Ile Tyr Val Ala Val Ile Ser Gly Val Gln Asn Val Gly Phe Pro
                85                  90                  95

Arg Trp Lys Leu Ile Asp His Gln Val Arg Pro Ser Glu Ser Ile Tyr
                100                 105                 110

Lys Val Leu Asp Val Asp Phe Tyr Ser Leu Glu Asn Asp Val Phe Asp
                115                 120                 125

Tyr Leu Leu Cys Glu Arg Ser Glu Gln Asn Tyr Asp Lys Leu Ile His
            130                 135                 140

Glu His Pro Cys Gly Pro Leu Lys Lys Leu Phe Ser Asp Gly Thr Phe
145                 150                 155                 160

Tyr Tyr Ser Arg Asp Phe Asp Ile Ser Asn Ile Val Lys Asn His Gly
                165                 170                 175

Leu Ser His Asn Leu Glu Tyr Thr Val Asp Asn Gln Asp Leu Ser Phe
                180                 185                 190

Ile Trp Asn Ala Asn Leu Ala Ser Glu Val Ile Asn Trp Arg Ser Lys
                195                 200                 205

Ile Ser Asn Glu Glu Lys Gln Leu Phe Ala Asn Ala Gly Phe Leu Thr
            210                 215                 220

Phe Val Ile Arg Gly Tyr Cys Lys Thr Ala Leu Ile Glu Asp Gly Pro
225                 230                 235                 240

Asn Thr Ala Ser Ile Thr Ile Ile Ser Arg Ile Ser Thr Glu Ser Lys
```

-continued

```
                245                 250                 255
Gln Asp Thr Leu Glu Leu Glu Gly Ile Ser Glu Asp Gly Arg Val Ser
            260                 265                 270

Leu Phe Val Glu Thr Glu Ile Val Val Thr Glu Lys Phe Ile Phe
        275                 280                 285

Ser Tyr Thr Gln Val Asn Gly Ser Ile Pro Leu Phe Trp Glu Ser Val
290                 295                 300

Glu Ser Gln Leu Leu Tyr Gly Lys Lys Ile Lys Val Thr Lys Asp Ser
305                 310                 315                 320

Ile Glu Ala Cys Gly Ala Glu Asp Arg His Phe Asp Asn Leu Thr Ser
                325                 330                 335

Lys Tyr Gly Val Val Ser Ile Val Asn Ile Ile Lys Pro Lys Ser Glu
            340                 345                 350

Ser Gln Glu Lys Leu Ala Leu Thr Tyr Lys Asp Cys Ala Glu Ser Lys
        355                 360                 365

Gly Ile Lys Ile Thr Asn Ile Glu Tyr Ser Ser Val Leu Thr Lys
    370                 375                 380

Ser Pro His Lys Leu Leu Tyr Leu Leu Lys Gln Asp Ile Tyr Glu Phe
385                 390                 395                 400

Gly Ala Phe Ala Tyr Asp Ile Ser Arg Gly Ile Tyr Phe Ala Lys Gln
                405                 410                 415

Thr Gly Val Leu Arg Ile Ser Ala Phe Asp Ser Ile Glu Lys Pro Asn
            420                 425                 430

Thr Val Glu Arg Leu Val Ser Lys Glu Val Leu Glu Thr Asn Asn
        435                 440                 445

Glu Ile Asp Val Phe Glu Leu Thr Ser Pro Phe Leu Asp Ala His Asp
    450                 455                 460

Lys Leu Trp Ser Glu Asn Tyr Tyr Trp Leu Asp Arg Thr Tyr Thr Lys
465                 470                 475                 480

His Thr Lys Asn Ser Gly Lys Tyr Thr Lys Val Tyr Ser Lys Leu Phe
                485                 490                 495

Gly Ser Arg Val Arg Leu Tyr Asp Pro Leu His Ile Tyr Ile Ser Gln
            500                 505                 510

Tyr Leu Lys Gln Leu Arg Ser Lys Tyr Thr Phe Glu Lys Asp Ile Ser
        515                 520                 525

Ile Phe Ala Gly Thr Phe Asn Ile Ser Gly Lys Ile Pro Lys Asp Asp
530                 535                 540

Ile Lys Asp Trp Ile Phe Pro Lys Ser Met Ser Lys Glu Asp Phe Met
545                 550                 555                 560

Ala Asp Leu Tyr Val Ile Gly Leu Glu Glu Val Val Glu Leu Thr Pro
                565                 570                 575

Gly His Met Leu Ala Thr Asp Pro Tyr Val Arg Gln Phe Trp Glu Lys
            580                 585                 590

Lys Ile Leu Thr Leu Leu Asn Gly Pro Gly Arg Lys Lys Lys Tyr Ile
        595                 600                 605

Arg Leu Trp Ser Thr Gln Leu Gly Gly Ile Leu Leu Leu Phe Met
    610                 615                 620

Asn Glu Thr Glu Tyr Ser Lys Val Lys His Ile Glu Gly Asp Val Lys
625                 630                 635                 640

Lys Thr Gly Phe Gly Gly Met Ala Ser Asn Lys Gly Ala Val Ala Val
                645                 650                 655

Ser Phe Lys Tyr Ser Ala Thr Arg Phe Cys Val Leu Val Ser His Leu
            660                 665                 670
```

```
Ala Ala Gly Leu Glu Asn Val Glu Gln Arg His Asn Asp Tyr Lys Thr
            675                 680                 685
Ile Ala Lys Ser Ile Arg Phe Ser Lys Gly Leu Arg Ile Lys Asp His
        690                 695                 700
Asp Ala Ile Phe Trp Phe Gly Asp Glu Asn Tyr Arg Ile Leu Met Ser
705                 710                 715                 720
Asn Glu Asp Val Arg Arg Lys Ile Val Ser Lys Glu Tyr Ala Ser Leu
                    725                 730                 735
Phe Glu Lys Asp Gln Leu Asn Gln Gln Met Ile Ala Gly Glu Ser Phe
                740                 745                 750
Pro Tyr Phe His Glu Met Ala Ile Asp Phe Pro Thr Tyr Lys Phe
            755                 760                 765
Asp Pro Gly Thr Lys Asn Tyr Asp Thr Ser Glu Lys Met Arg Leu Pro
770                 775                 780
Ala Trp Thr Asp Arg Ile Leu Ser Arg Gly Glu Val Leu Glu Gln Leu
785                 790                 795                 800
Glu Tyr Lys Cys Cys Glu Asp Ile Leu Phe Ser Asp His Arg Pro Val
                805                 810                 815
Tyr Ala Ile Phe Arg Ala Arg Val Thr Val Val Asp Glu Gln Lys Lys
                820                 825                 830
Thr Thr Leu Gly Thr Gln Ile Tyr Glu Lys Ile Met Glu Arg Leu Glu
            835                 840                 845
Gly Leu Asp Asp Asp Glu Lys Ile Ala Val Leu Ser Asp Asp Ala Phe
850                 855                 860
Val Ile Glu Ser Phe Glu Gly Ser Asp Ser Ile Ala Gly Pro Thr His
865                 870                 875                 880
Ser Pro Thr Pro Ile Pro Glu Pro Lys Arg Gly Arg Lys Leu Pro Pro
                885                 890                 895
Pro Ser Ser Asp Leu Lys Lys Trp Trp Ile Gly Ser Gly Lys Gln Val
                900                 905                 910
Lys Val Val Leu Asp Val Asp Pro Ala Val Tyr Met Ile Asn Pro Lys
                915                 920                 925
Arg Asp Pro Asn Pro Glu Val Glu Asn Glu Asp Glu Pro Leu Phe Ile
930                 935                 940
Glu Arg
945

(2) INFORMATION FOR SEQ ID NO:5:

(i) SEQUENCE CHARACTERISTICS:
        (A) LENGTH: 1149 amino acids
        (B) TYPE: amino acid
        (D) TOPOLOGY: linear (ii) MOLECULE TYPE: protein (ix) FEATURE:
        (A) NAME/KEY: Region
        (B) LOCATION: 1..1149
        (D) OTHER INFORMATION: /note= "51c"

(xi) SEQUENCE DESCRIPTION: SEQ ID NO:5:

Met Cys Thr Arg Ile Ala Pro Cys Leu Met Glu Lys Ile Ser Trp Leu
1               5                   10                  15
Cys Arg Pro Arg Arg Val Cys Leu Cys Pro Ala Ser Arg Pro Trp Val
                20                  25                  30
Ser Ser Ser Ala Cys Thr Pro Ser Pro Thr Arg Ala Leu Cys Ala Pro
            35                  40                  45
```

-continued

| | | | | | | | | | | | |
|---|---|---|---|---|---|---|---|---|---|---|---|
|Cys|Leu|Phe|Leu|Tyr|Arg|Val|Ser|Glu|Ser|Arg|Thr|His|Arg|Met|Thr|
| |50| | | | |55| | | | |60| | | | |
|Gly|Met|Pro|Gln|Met|Gly|Arg|Met|Arg|Ser|Pro|Arg|Cys|Pro|Arg|Ala|
|65| | | | |70| | | | |75| | | | |80|
|Leu|Ala|Pro|Pro|Ala|Phe|Leu|Pro|Pro|Thr|Gly|Pro|Ser|Ser|Pro|Leu|
| | | | |85| | | | |90| | | | |95| |
|Pro|Ala|Pro|Glu|Thr|Pro|Thr|Ala|Pro|Ala|Ala|Glu|Ser|Ala|Pro|Asn|
| | | |100| | | | |105| | | | |110| | |
|Gly|Leu|Ser|Thr|Val|Ser|His|Asp|Tyr|Leu|Lys|Gly|Ser|Tyr|Gly|Leu|
| | |115| | | | |120| | | | |125| | | |
|Asp|Leu|Glu|Ala|Val|Arg|Gly|Gly|Ala|Ser|His|Leu|Pro|His|Leu|Thr|
| |130| | | | |135| | | | |140| | | | |
|Arg|Thr|Leu|Ala|Thr|Ser|Cys|Arg|Arg|Leu|His|Ser|Glu|Val|Asp|Lys|
|145| | | | |150| | | | |155| | | | |160|
|Val|Leu|Ser|Gly|Leu|Glu|Ile|Leu|Ser|Lys|Val|Phe|Asp|Gln|Gln|Ser|
| | | | |165| | | | |170| | | | |175| |
|Ser|Pro|Met|Val|Thr|Arg|Leu|Leu|Gln|Gln|Gln|Asn|Leu|Pro|Gln|Thr|
| | | |180| | | | |185| | | | |190| | |
|Gly|Glu|Glu|Glu|Leu|Glu|Ser|Leu|Val|Leu|Lys|Leu|Ser|Val|Leu|Lys|
| | |195| | | | |200| | | | |205| | | |
|Asp|Phe|Leu|Ser|Gly|Ile|Gln|Lys|Lys|Ala|Leu|Lys|Ala|Leu|Gln|Asp|
| |210| | | | |215| | | | |220| | | | |
|Met|Ser|Ser|Thr|Ala|Pro|Pro|Ala|Pro|Gln|Pro|Ser|Thr|Arg|Lys|Ala|
|225| | | | |230| | | | |235| | | | |240|
|Lys|Thr|Met|Pro|Val|Gln|Ala|Phe|Glu|Val|Lys|Leu|Asp|Val|Thr|Leu|
| | | | |245| | | | |250| | | | |255| |
|Gly|Asp|Leu|Thr|Lys|Ile|Gly|Lys|Ser|Gln|Lys|Phe|Thr|Leu|Ser|Val|
| | | |260| | | | |265| | | | |270| | |
|Asp|Val|Glu|Gly|Gly|Arg|Leu|Val|Leu|Leu|Arg|Arg|Gln|Arg|Asp|Ser|
| | |275| | | | |280| | | | |285| | | |
|Gln|Glu|Asp|Trp|Thr|Thr|Phe|Thr|His|Asp|Arg|Ile|Arg|Gln|Leu|Ile|
| |290| | | | |295| | | | |300| | | | |
|Lys|Ser|Gln|Arg|Val|Gln|Asn|Lys|Leu|Gly|Val|Val|Phe|Glu|Lys|Glu|
|305| | | | |310| | | | |315| | | | |320|
|Lys|Asp|Arg|Thr|Gln|Arg|Lys|Asp|Phe|Ile|Phe|Val|Ser|Ala|Arg|Lys|
| | | | |325| | | | |330| | | | |335| |
|Arg|Glu|Ala|Phe|Cys|Gln|Leu|Leu|Gln|Gln|Met|Lys|Asn|Lys|His|Ser|
| | | |340| | | | |345| | | | |350| | |
|Lys|Gln|Asp|Glu|Pro|Asp|Met|Ile|Ser|Met|Phe|Ile|Gly|Thr|Trp|Asn|
| | |355| | | | |360| | | | |365| | | |
|Met|Gly|Ser|Val|Pro|Pro|Lys|Asn|Val|Thr|Ser|Trp|Phe|Thr|Ser|
| |370| | | | |375| | | | |380| | | | |
|Lys|Gly|Leu|Gly|Lys|Thr|Leu|Asp|Glu|Val|Thr|Val|Thr|Ile|Pro|His|
|385| | | | |390| | | | |395| | | | |400|
|Asp|Ile|Tyr|Val|Phe|Gly|Thr|Gln|Glu|Asn|Ser|Val|Gly|Asp|Arg|Glu|
| | | | |405| | | | |410| | | | |415| |
|Trp|Leu|Asp|Leu|Leu|Arg|Gly|Gly|Leu|Lys|Glu|Leu|Thr|Asp|Leu|Asp|
| | | |420| | | | |425| | | | |430| | |
|Tyr|Arg|Pro|Val|Ala|Met|Gln|Ser|Leu|Trp|Asn|Ile|Lys|Val|Ala|Val|
| | |435| | | | |440| | | | |445| | | |
|Leu|Val|Lys|Pro|Glu|His|Glu|Asn|Arg|Ile|Ser|His|Val|Ser|Thr|Ser|
| |450| | | | |455| | | | |460| | | | |
|Ser|Val|Lys|Thr|Gly|Ile|Ala|Asn|Thr|Leu|Gly|Asn|Lys|Gly|Ala|Val|
|465| | | | |470| | | | |475| | | | |480|

```
Gly Val Ser Phe Met Phe Asn Gly Thr Ser Phe Gly Phe Val Asn Cys
                485                 490                 495

His Leu Thr Ser Gly Ser Glu Lys Thr Ala Arg Arg Asn Gln Asn Tyr
                500                 505                 510

Leu Asp Ile Leu Arg Leu Leu Ser Leu Gly Asp Arg Gln Leu Asn Ala
                515                 520                 525

Phe Asp Ile Ser Leu Arg Phe Thr His Leu Phe Trp Phe Gly Asp Leu
530                 535                 540

Asn Tyr Arg Leu Asp Met Asp Ile Gln Glu Ile Leu Asn Tyr Ile Ser
545                 550                 555                 560

Ser Lys Glu Phe Glu Pro Leu leu Arg Val Asp Gln Leu Asn Leu Glu
                565                 570                 575

Arg Glu Lys His Lys Val Phe Leu Arg Phe Ser Glu Glu Ile Ser
                580                 585                 590

Phe Pro Pro Thr Tyr Arg Tyr Glu Arg Gly Ser Arg Asp Thr Tyr Ala
                595                 600                 605

Trp His Lys Gln Lys Pro Thr Gly Val Arg Thr Asn Val Pro Ser Trp
                610                 615                 620

Cys Asp Arg Ile Leu Trp Lys Ser Tyr Pro Glu Thr His Ile Val Cys
625                 630                 635                 640

Asn Ser Tyr Gly Cys Thr Asp Asp Ile Val Thr Ser Asp His Ser Pro
                645                 650                 655

Val Phe Gly Thr Phe Glu Val Gly Val Thr Ser Gln Phe Ile Ser Lys
                660                 665                 670

Lys Gly Leu Ser Lys Thr Ser Asp Gln Ala Tyr Ile Glu Phe Glu Ser
                675                 680                 685

Ile Glu Ala Ile Val Lys Thr Ala Ser Arg Thr Lys Phe Tyr Ile Glu
                690                 695                 700

Phe Tyr Ser Thr Cys Leu Glu Glu Tyr Lys Lys Ser Phe Glu Asn Asp
705                 710                 715                 720

Ala Gln Ser Ser Asp Asn Ile Asn Phe Leu Lys Val Lys Trp Ser Ser
                725                 730                 735

Arg Gln Leu Pro Thr Leu Lys Pro Ile Leu Ala Asp Ile Glu Tyr Leu
                740                 745                 750

Gln Asp Gln His Leu Leu Leu Thr Val Lys Ser Met Asp Gly Tyr Glu
                755                 760                 765

Ser Tyr Gly Glu Cys Val Val Ala Leu Lys Ser Met Ile Gly Ser Thr
                770                 775                 780

Ala Gln Gln Phe Leu Thr Phe Leu Ser His Arg Gly Glu Glu Thr Gly
785                 790                 795                 800

Asn Ile Arg Gly Ser Met Lys Val Arg Val Pro Thr Glu Arg Leu Gly
                805                 810                 815

Thr Arg Glu Arg Leu Tyr Glu Trp Ile Ser Ile Asp Lys Asp Glu Ala
                820                 825                 830

Gly Ala Lys Ser Ser Pro Ile His Thr Leu Cys Tyr Met Arg Glu Pro
                835                 840                 845

Arg Ser Gly Ser Arg Lys Pro Ala Phe Thr Glu Ala Ser Cys Pro Leu
                850                 855                 860

Ser Arg Leu Phe Glu Glu Pro Glu Lys Pro Pro Thr Gly Arg Pro
865                 870                 875                 880

Pro Ala Pro Pro Arg Ala Ala Pro Arg Glu Glu Pro Leu Thr Pro Arg
                885                 890                 895

Leu Lys Pro Glu Gly Ala Pro Glu Pro Glu Gly Val Ala Ala Pro Pro
```

```
                    900             905             910
Pro Lys Asn Ser Phe Asn Asn Pro Ala Tyr Tyr Val Leu Glu Gly Val
            915                 920             925

Pro His Gln Leu Leu Pro Pro Glu Pro Pro Ser Pro Ala Arg Ala Pro
    930                 935                 940

Val Pro Ser Ala Thr Lys Asn Lys Val Ala Ile Thr Val Pro Ala Pro
945                 950                 955                 960

Gln Leu Gly His His Arg His Pro Arg Val Gly Gly Ser Ser Ser
                965             970                 975

Asp Glu Glu Ser Gly Gly Thr Leu Pro Pro Asp Phe Pro Pro
            980             985                 990

Pro Leu Pro Asp Ser Ala Ile Phe Leu Pro Pro Ser Leu Asp Pro Leu
    995                 1000                1005

Pro Gly Pro Val Val Arg Gly Arg Gly Gly Ala Glu Ala Arg Gly Pro
    1010                1015            1020

Pro Pro Pro Lys Ala His Pro Arg Pro Leu Pro Pro Gly Pro Ser
1025            1030            1035                1040

Pro Ala Ser Thr Phe Leu Gly Glu Val Ala Ser Gly Asp Asp Arg Ser
                1045            1050                1055

Cys Ser Val Leu Gln Met Ala Lys Thr Leu Ser Glu Val Asp Tyr Ala
            1060                1065            1070

Pro Ala Gly Pro Ala Ala Ser Ala Leu Leu Pro Gly Pro Leu Glu Leu
            1075            1080            1085

Gln Pro Pro Pro Gly Thr Ala Leu Gly Leu Trp Pro Ala Pro Gln Leu
    1090            1095            1100

Pro Ser Thr Pro His Pro Gly Glu His Pro Gly Arg Pro Gly Arg Gly
1105            1110            1115                1120

Gly Ser Val Pro Ala Gly Arg Ala Gly Gln Arg Ala Gly Arg Gly Arg
            1125            1130            1135

His Glu Cys Leu Ala Ala Gly His Arg Leu Gly Ala Leu
            1140            1145

(2) INFORMATION FOR SEQ ID NO:6:

(i) SEQUENCE CHARACTERISTICS:
        (A) LENGTH: 942 amino acids
        (B) TYPE: amino acid
        (D) TOPOLOGY: linear (ii) MOLECULE TYPE: protein (ix) FEATURE:
        (A) NAME/KEY: Region
        (B) LOCATION: 1..942
        (D) OTHER INFORMATION: /note= "majptase"

(xi) SEQUENCE DESCRIPTION: SEQ ID NO:6:

Val Thr Val Pro Glu Pro Gly Ala Ala Glu Ser Arg Ala Pro Cys Gly
 1               5                  10                  15

Asp Ser Ser Gly Gly Cys Val Arg Ser Ala Gly Ala Ser Met Asp Gln
            20                  25                  30

Ser Val Ala Ile Gln Glu Thr Leu Ala Glu Gly Glu Tyr Cys Val Ile
        35                  40                  45

Ala Val Gln Gly Val Leu Cys Glu Gly Asp Ser Arg Gln Ser Arg Leu
    50                  55                  60

Leu Gly Leu Val Arg Tyr Arg Leu Glu His Gly Gln Glu His Ala
65              70                  75                  80

Leu Phe Leu Tyr Thr His Arg Arg Met Ala Ile Thr Gly Asp Asp Val
```

```
                85                    90                     95
Ser Leu Asp Gln Ile Val Pro Val Ser Arg Asp Phe Thr Leu Glu Glu
            100                     105                    110

Val Ser Pro Asp Gly Glu Leu Tyr Ile Leu Gly Ser Asp Val Thr Val
        115                     120                    125

Gln Leu Asp Thr Ala Glu Leu Ser Leu Val Phe Gln Leu Pro Phe Gly
    130                     135                    140

Ser Gln Thr Arg Met Phe Leu His Glu Val Ala Arg Ala Cys Pro Gly
145                     150                    155                    160

Phe Asp Ser Ala Thr Arg Asp Pro Glu Phe Leu Trp Leu Ser Arg Tyr
                165                    170                    175

Arg Cys Ala Glu Leu Glu Leu Glu Met Pro Thr Pro Arg Gly Cys Asn
            180                    185                    190

Ser Ala Trp Val Thr Trp Pro Gly Tyr Ala Thr Ile Gly Gly Gly Gly
        195                    200                    205

Ser Asn Phe Asp Gly Leu Arg Pro Asn Gly Lys Gly Val Pro Met Asp
    210                    215                    220

Gln Ser Ser Arg Gly Gln Asp Lys Pro Glu Ser Leu Gln Pro Arg Gln
225                    230                    235                    240

Asn Lys Ser Lys Ser Glu Ile Thr Asp Met Val Arg Ser Ser Thr Ile
                245                    250                    255

Thr Val Ser Asp Lys Ala His Ile Leu Ser Met Gln Lys Phe Gly Leu
            260                    265                    270

Arg Asp Thr Ile Val Lys Ser His Leu Leu Gln Lys Glu Glu Asp Tyr
        275                    280                    285

Thr Tyr Ile Gln Asn Phe Arg Phe Phe Ala Gly Thr Tyr Asn Val Asn
    290                    295                    300

Gly Gln Ser Pro Lys Glu Cys Leu Arg Leu Trp Leu Ser Asn Gly Ile
305                    310                    315                    320

Gln Ala Pro Asp Val Tyr Cys Val Gly Phe Gln Glu Leu Leu Leu Ser
                325                    330                    335

Lys Glu Ala Phe Phe Phe His Asp Thr Pro Lys Glu Glu Glu Trp Phe
            340                    345                    350

Lys Ala Val Ser Glu Gly Leu His Pro Asp Ala Lys Tyr Ala Lys Val
        355                    360                    365

Lys Leu Ile Arg Leu Val Gly Ile Met Leu Leu Leu Tyr Val Lys Gln
    370                    375                    380

Glu His Ala Ala Tyr Ile Ser Glu Val Glu Ala Glu Thr Val Gly Thr
385                    390                    395                    400

Gly Ile Met Gly Arg Met Gly Asn Lys Gly Gly Val Ala Ile Arg Phe
                405                    410                    415

Gln Phe His Asn Thr Ser Ile Cys Val Val Asn Ser His Leu Ala Ala
            420                    425                    430

His Ile Glu Glu Tyr Glu Arg Arg Asn Gln Asp Tyr Lys Asp Ile Cys
        435                    440                    445

Ser Arg Met Gln Phe Cys Gln Pro Asp Pro Ser Leu Pro Pro Leu Thr
    450                    455                    460

Ile Ser Asn His Asp Val Ile Leu Trp Met Gly Asp Leu Asn Tyr Arg
465                    470                    475                    480

Ile Glu Glu Leu Asp Val Glu Lys Val Lys Lys Leu Ile Glu Glu Lys
                485                    490                    495

Asp Phe Gln Met Leu Tyr Ala Tyr Asp Gln Leu Lys Ile Gln Val Ala
            500                    505                    510
```

-continued

```
Ala Lys Thr Val Phe Glu Gly Phe Thr Glu Gly Leu Thr Phe Gln
    515                 520                 525

Pro Thr Tyr Lys Tyr Asp Thr Gly Ser Asp Asp Trp Asp Thr Ser Glu
    530                 535                 540

Lys Cys Arg Ala Pro Ala Trp Cys Asp Arg Ile Leu Trp Lys Gly Lys
545                 550                 555                 560

Asn Ile Thr Gln Leu Ser Tyr Gln Ser His Met Ala Leu Lys Thr Ser
                565                 570                 575

Asp His Lys Pro Val Ser Ser Val Phe Asp Ile Gly Val Arg Val Val
                580                 585                 590

Asn Asp Glu Leu Tyr Arg Lys Thr Leu Glu Glu Ile Val Arg Ser Leu
                595                 600                 605

Asp Lys Met Glu Asn Ala Asn Ile Pro Ser Val Ser Leu Ser Lys Arg
610                 615                 620

Glu Phe Cys Phe Gln Asn Val Lys Tyr Met Gln Leu Lys Val Glu Ser
625                 630                 635                 640

Phe Thr Ile His Asn Gly Gln Val Pro Cys His Phe Glu Phe Ile Asn
                645                 650                 655

Lys Pro Asp Glu Glu Ser Tyr Cys Lys Gln Trp Leu Asn Ala Asn Pro
                660                 665                 670

Ser Arg Gly Phe Leu Leu Pro Asp Ser Asp Val Glu Ile Asp Leu Glu
                675                 680                 685

Leu Glu Val Asn Lys Thr Thr Ala Thr Lys Leu Asn Ser Gly Glu Asp
690                 695                 700

Lys Ile Glu Asp Ile Leu Val Leu His Leu Asp Arg Gly Lys Asp Tyr
705                 710                 715                 720

Phe Leu Ser Val Ser Gly Asn Tyr Leu Pro Ser Cys Phe Gly Ser Pro
                725                 730                 735

Ile His Thr Leu Cys Tyr Met Arg Glu Pro Ile Leu Asp Leu Pro Leu
                740                 745                 750

Glu Thr Ile Ser Glu Leu Thr Leu Met Pro Val Trp Thr Gly Asp Asp
                755                 760                 765

Gly Ser Gln Leu Asp Ser Pro Met Glu Ile Pro Lys Glu Leu Trp Met
                770                 775                 780

Met Val Asp Tyr Leu Tyr Arg Asn Ala Val Gln Gln Glu Asp Leu Phe
785                 790                 795                 800

Gln Cys Pro Gly Leu Arg Ser Glu Phe Glu His Ile Arg Asp Cys Leu
                805                 810                 815

Asp Thr Gly Met Ile Asp Asn Leu Ser Ala Ser Asn His Ser Val Ala
                820                 825                 830

Glu Ala Leu Leu Ile Phe Leu Glu Ser Leu Pro Glu Pro Val Ile Cys
                835                 840                 845

Tyr Ser Thr Tyr His Asn Cys Leu Glu Cys Ser Gly Asn Tyr Thr Ala
850                 855                 860

Ser Lys Gln Val Ile Ser Thr Leu Pro Ile Phe His Lys Asn Val Phe
865                 870                 875                 880

His Tyr Leu Met Ala Phe Leu Arg Glu Leu Leu Lys Asn Ser Ala Lys
                885                 890                 895

Asn His Leu Asp Glu Asn Ile Leu Ala Ser Ile Phe Gly Ser Leu Leu
                900                 905                 910

Leu Arg Asn Pro Ala Gly His Gln Lys Leu Asp Met Thr Glu Lys Lys
                915                 920                 925

Lys Ala Gln Glu Phe Ile His Gln Phe Leu Cys Asn Pro Leu
930                 935                 940
```

(2) INFORMATION FOR SEQ ID NO:7:

(i) SEQUENCE CHARACTERISTICS:
        (A) LENGTH: 968 amino acids
        (B) TYPE: amino acid
        (D) TOPOLOGY: linear (ii) MOLECULE TYPE: protein (ix) FEATURE:
        (A) NAME/KEY: Region
        (B) LOCATION: 1..968
        (D) OTHER INFORMATION: /note= "ocr1"

(xi) SEQUENCE DESCRIPTION: SEQ ID NO:7:

```
Met Lys Phe Phe Val Phe Lys Ser Phe Leu ser Asp Cys Tyr Arg Ser
 1               5                  10                  15

Leu Leu Asp Lys Ser Gln Leu Pro Ala Pro Arg Ser Arg Leu Pro Ala
            20                  25                  30

Pro Gly Ala Arg Arg Gly Ala Val Pro Gln Thr Thr Arg Ser Arg Gly
        35                  40                  45

Gly Trp Val Trp Gly Arg Gly Ser Gln Cys Arg Arg Ile Gly Pro Gln
 50                  55                  60

Ser Ala Val Leu Leu Ser Pro Glu Ala Ala Trp Met Glu Pro Pro Leu
 65                  70                  75                  80

Pro Val Gly Ala Gln Pro Leu Ala Thr Val Glu Gly Met Glu Met Lys
                85                  90                  95

Gly pro Leu Arg Glu Pro Cys Ala Leu Thr Leu Ala Gln Arg Asn Gly
            100                 105                 110

Gln Tyr Glu Leu Ile Ile Gln Leu His Glu Lys Glu Gln His Val Gln
        115                 120                 125

Asp Ile Ile Pro Ile Asn Ser His Phe Arg Cys Val Gln Glu Ala Glu
    130                 135                 140

Glu Thr Leu Leu Ile Asp Ile Ala Ser Asn Ser Gly Cys Lys Ile Arg
145                 150                 155                 160

Val Gln Gly Asp Trp Ile Arg Glu Arg Arg Phe Glu Ile Pro Asp Glu
                165                 170                 175

Glu His Cys Leu Lys Glu Leu Ser Ala Val Leu Ala Ala Gln Lys Ala
            180                 185                 190

Gln Ser Gln Leu Leu Val Pro Glu Gln Lys Asp Ser Ser Ser Trp Tyr
        195                 200                 205

Gln Lys Leu Asp Thr Lys Asp Lys Pro Ser Val Phe Ser Gly Leu Leu
    210                 215                 220

Gly Phe Glu Asp Asn Phe Ser Ser Met Asn Leu Asp Lys Lys Ile Asn
225                 230                 235                 240

Ser Gln Asn Gln Pro Thr Gly Thr His Arg Glu Pro Pro Pro Pro
                245                 250                 255

Phe Ser Val Asn Lys Met Leu Pro Arg Glu Lys Glu Ala Ser Asn Lys
            260                 265                 270

Glu Gln Pro Lys Val Thr Asn Thr Met Arg Lys Phe Phe Val Pro Asn
        275                 280                 285

Thr Gln Ser Gly Gln Arg Glu Gly Leu Ile Lys His Ile Leu Ala Lys
    290                 295                 300

Arg Glu Lys Glu Tyr Val Asn Ile Gln Thr Phe Arg Phe Val Gly
305                 310                 315                 320

Thr Trp Asn Val Asn Gly Gln Ser Pro Asp Ser Gly Leu Glu Pro Trp
                325                 330                 335
```

```
Leu Asn Cys Asp Pro Asn Pro Pro Asp Ile Tyr Cys Ile Gly Phe Gln
            340                 345                 350

Glu Leu Leu Leu Ser Thr Glu Ala Phe Phe Tyr Phe Glu Ser Val Lys
                355                 360                 365

Glu Gln Glu Trp Ser Met Ala Val Glu Arg Gly Leu His Ser Lys Ala
    370                 375                 380

Lys Tyr Lys Lys Val Gln Leu Val Arg Leu Val Gly Met Met Leu Leu
385                 390                 395                 400

Ile Phe Ala Arg Lys Asp Gln Cys Arg Tyr Ile Arg Asp Ile Ala Thr
                405                 410                 415

Glu Thr Val Gly Thr Gly Ile Met Gly Lys Met Gly Asn Lys Gly Gly
            420                 425                 430

Val Ala Val Arg Phe Val Phe His Asn Thr Thr Phe Cys Ile Val Asn
            435                 440                 445

Ser His Leu Ala Ala His Val Glu Asp Leu Glu Arg Arg Asn Gln Asp
        450                 455                 460

Tyr Lys Asp Ile Cys Ala Arg Met Ser Phe Val Val Pro Asn Gln Thr
465                 470                 475                 480

Leu Pro Gln Leu Asn Ile Met Lys His Glu Val Val Ile Trp Met Gly
                485                 490                 495

Asp Leu Asn Tyr Arg Leu Cys Met Pro Asp Ala Asn Glu Val Lys Ser
            500                 505                 510

Leu Ile Asn Lys Lys Asp Leu Gln Arg Leu Leu Lys Phe Asp Gln Leu
        515                 520                 525

Asn Ile Gln Arg Thr Gln Lys Lys Ala Phe Val Asp Phe Asn Glu Gly
        530                 535                 540

Glu Ile Lys Phe Ile Pro Thr Tyr Lys Tyr Asp Ser Lys Thr Asp Arg
545                 550                 555                 560

Trp Asp Ser Ser Gly Lys Cys Arg Val Pro Ala Trp Cys Asp Arg Ile
                565                 570                 575

Leu Trp Arg Gly Thr Asn Val Asn Gln Leu Asn Tyr Arg Ser His Met
            580                 585                 590

Leu Leu Lys Thr Ser Asp His Lys Pro Val Ser Ala Leu Phe His Ile
        595                 600                 605

Gly Val Lys Val Val Asp Glu Arg Arg Tyr Arg Lys Val Phe Glu Asp
    610                 615                 620

Ser Val Arg Ile Met Asp Arg Met Glu Asn Asp Phe Leu Pro Ser Leu
625                 630                 635                 640

Glu Leu Ser Arg Arg Glu Phe Val Phe Glu Asn Val Lys Phe Arg Gln
                645                 650                 655

Leu Gln Lys Gly Lys Phe Gln Ile Ser Asn Asn Gly Gln Val Pro Cys
            660                 665                 670

His Phe Ser Phe Ile Pro Lys Leu Asn Asp Ser Gln Tyr Cys Lys Pro
        675                 680                 685

Trp Leu Arg Ala Glu Pro Phe Glu Gly Tyr Leu Glu Pro Asn Glu Thr
    690                 695                 700

Val Asp Ile Ser Leu Asp Val Tyr Val Ser Lys Asp Ser Val Thr Ile
705                 710                 715                 720

Leu Asn Ser Gly Glu Asp Lys Ile Glu Asp Ile Leu Val Leu His Leu
                725                 730                 735

Asp Arg Gly Lys Asp Tyr Phe Leu Thr Ile Ser Gly Asn Tyr Leu Pro
            740                 745                 750

Ser Cys Phe Gly Thr Ser Leu Glu Ala Leu Cys Arg Met Lys Arg Pro
```

```
                     755                 760                 765
Ile Arg Glu Val Pro Val Thr Lys Leu Ile Asp Leu Glu Lys Ser Leu
    770                 775                 780
Leu Gln Met Val Pro Leu Asp Glu Gly Ala Ser Glu Arg Pro Leu Gln
785                 790                 795                 800
Val Pro Lys Glu Ile Trp Leu Leu Val Asp His Leu Phe Lys Tyr Ala
                805                 810                 815
Cys His Gln Glu Asp Leu Phe Gln Thr Pro Gly Met Gln Glu Glu Leu
                820                 825                 830
Gln Gln Ile Ile Asp Cys Leu Asp Thr Ser Ile Pro Glu Thr Ile Pro
                835                 840                 845
Gly Ser Asn His Ser Val Ala Glu Ala Leu Leu Ile Phe Leu Glu Ala
850                 855                 860
Leu Pro Glu Pro Val Ile Cys Tyr Glu Leu Tyr Gln Arg Cys Leu Asp
865                 870                 875                 880
Ser Ala Tyr Asp Pro Arg Ile Cys Arg Gln Val Ile Ser Gln Leu Pro
                885                 890                 895
Arg Cys His Arg Asn Val Phe Arg Tyr Leu Met Ala Phe Leu Arg Glu
                900                 905                 910
Leu Leu Lys Phe Ser Glu Tyr Asn Ser Val Asn Ala Asn Met Ile Ala
                915                 920                 925
Thr Leu Phe Thr Ser Leu Leu Leu Arg Pro Pro Pro Asn Leu Met Ala
930                 935                 940
Arg Gln Thr Pro Ser Asp Arg Gln Arg Ala Ile Gln Phe Leu Leu Gly
945                 950                 955                 960
Phe Leu Leu Gly Ser Glu Glu Asp
                965

(2) INFORMATION FOR SEQ ID NO:8:

(i) SEQUENCE CHARACTERISTICS:
        (A) LENGTH: 121 amino acids
        (B) TYPE: amino acid
        (D) TOPOLOGY: linear (ii) MOLECULE TYPE: protein (ix) FEATURE:
        (A) NAME/KEY: Region
        (B) LOCATION: 1..121
        (D) OTHER INFORMATION: /note= "arab5ptase"

(xi) SEQUENCE DESCRIPTION: SEQ ID NO:8:

Ser Gly Glu Lys Asp Thr Asp Gln Glu Lys Arg Asn Asp Asp Val Arg
1               5                  10                  15
Glu Ile His Arg Arg Thr Gln Phe Leu Pro His Ser Leu Asn Ala Asn
                20                  25                  30
Glu Leu Pro Arg Ser Ile Cys Asn His Glu Arg Ile Ile Asn Met Gly
            35                  40                  45
Asp Leu Asn Tyr Arg Ile Asn Leu Ser Tyr Glu Lys Thr His Glu Leu
        50                  55                  60
Ile Ala Arg Lys Ser Trp Gln Arg Leu Val Glu Tyr Asp Gln Leu Ser
65                  70                  75                  80
Arg Glu Met Thr Lys Gly Asn Leu Phe Glu Gly Trp Ser Glu Gly Thr
                85                  90                  95
Leu Asp Phe Ala Pro Thr Tyr Lys Tyr Glu Ser Ile Gln Lys Ile Thr
            100                 105                 110
Ser Glu Met Thr Arg Asn Pro Gly Thr
```

115                 120

(2) INFORMATION FOR SEQ ID NO:9:

(i) SEQUENCE CHARACTERISTICS:
        (A) LENGTH: 412 amino acids
        (B) TYPE: amino acid
        (D) TOPOLOGY: linear (ii) MOLECULE TYPE: protein (ix) FEATURE:
        (A) NAME/KEY: Region
        (B) LOCATION: 1..412
        (D) OTHER INFORMATION: /note= "c5ptase43"

(xi) SEQUENCE DESCRIPTION: SEQ ID NO:9:

Met Ala Gly Lys Ala Ala Pro Gly Thr Ala Val Leu Leu Val Thr
 1               5                  10                  15

Ala Asn Val Gly Ser Leu Phe Asp Asp Pro Glu Asn Leu Gln Lys Asn
                20                  25                  30

Trp Leu Arg Glu Phe Tyr Gln Val Val His Thr His Lys Pro His Phe
                35                  40                  45

Met Ala Leu His Cys Gln Glu Phe Gly Gly Lys Asn Tyr Glu Ala Ser
        50                  55                  60

Met Ser His Val Asp Lys Phe Val Lys Glu Leu Leu Ser Ser Asp Ala
65                  70                  75                  80

Met Lys Glu Tyr Asn Arg Ala Arg Val Tyr Leu Asp Glu Asn Phe Lys
                85                  90                  95

Ser Gln Glu His Phe Thr Ala Leu Gly Ser Phe Tyr Phe Leu His Glu
                100                 105                 110

Ser Leu Lys Asn Ile Tyr Gln Phe Asp Phe Lys Ala Lys Lys Tyr Lys
            115                 120                 125

Lys Val Thr Gly Lys Glu Ile Tyr Ser Asp Thr Leu Glu Ser Thr Pro
        130                 135                 140

Met Leu Glu Lys Glu Lys Phe Pro Gln Asp Tyr Phe Pro Glu Cys Lys
145                 150                 155                 160

Trp Ser Arg Lys Gly Phe Val Arg Thr Arg Trp Cys Val Ala Asp Cys
                165                 170                 175

Ala Phe Asp Leu Val Asn Ile His Leu Phe His Asp Ala Ser Asn Leu
                180                 185                 190

Val Ala Trp Glu Thr Ser Pro Ser Leu Tyr Ser Gly Ile Arg His Lys
            195                 200                 205

Ala Leu Gly Tyr Val Leu Asp Arg Ile Ile Asp Gln Arg Phe Glu Lys
        210                 215                 220

Val Ser Tyr Phe Val Phe Gly Asp Glu Asn Phe Arg Leu Asp Ser Lys
225                 230                 235                 240

Ser Val Val Glu Thr Leu Cys Thr Lys Ala Thr Met Gln Thr Val Arg
                245                 250                 255

Ala Ala Asp Thr Asn Glu Val Val Lys Leu Ile Phe Arg Glu Ser Asp
                260                 265                 270

Asn Asp Arg Lys Val Met Leu Gln Leu Glu Lys Lys Leu Phe His Tyr
            275                 280                 285

Phe Asn Gln Glu Val Phe Arg Asp Asn Asn Gly Thr Ala Asp Leu Glu
        290                 295                 300

Phe Asp Lys Glu Leu Ser Val Phe Lys Asp Arg Leu Tyr Glu Leu Asp
305                 310                 315                 320

Ile Ser Phe Pro Pro Ser Tyr Pro Tyr Ser Glu Asp Ser Gly Gln Gly

|  | | | | 325 | | | | 330 | | | | 335 | |
| --- | --- | --- | --- | --- | --- | --- | --- | --- | --- | --- | --- | --- | --- |

Arg Gln Tyr Met Asn Thr Arg Cys Pro Ala Trp Cys Asp Arg Val Leu
                  340                        345                    350

Met Ser Pro Ser Ala Arg Glu Leu Ile Leu Lys Ser Glu Ser Glu Glu
    355                        360                    365

Lys Val Val Thr Tyr Asp His Ile Gly Pro Asn Val Cys Met Gly Asp
    370                        375                    380

His Lys Pro Val Phe Leu Ala Phe Arg Ile Ala Pro Gly Ala Gly Lys
385                        390                    395                    400

Pro His Ala His Val His Lys Cys Cys Val Val Gln
                  405                        410

(2) INFORMATION FOR SEQ ID NO:10:

(i) SEQUENCE CHARACTERISTICS:
        (A) LENGTH: 654 amino acids
        (B) TYPE: amino acid
        (D) TOPOLOGY: linear (ii) MOLECULE TYPE: protein (ix) FEATURE:
        (A) NAME/KEY: Region
        (B) LOCATION: 1..654
        (D) OTHER INFORMATION: /note= "consensus"

(xi) SEQUENCE DESCRIPTION: SEQ ID NO:10:

Glu Leu Arg Val Ser Ala Glu Ser Arg Ala Cys Ala Ala Phe Val Val
1                    5                    10                    15

Ser Gly Arg Ser Val Cys Ala Ser Cys Ser Gln Leu Pro Glu Ser Pro
                  20                        25                    30

Leu Pro Val Gly Gln Pro Ala Leu Phe Ser His Gly Ser Leu Thr Glu
     35                        40                    45

Val Glu Phe Thr Leu Ala Arg Gln Gly Glu Leu Glu Leu Ser Leu Glu
    50                        55                    60

Val Phe Asp Gln Ser Pro Ala Glu Gln Leu Leu Pro Gly Glu Ser Ile
65                       70                    75                    80

Val Lys Leu Ser Leu Ser Leu Ser Ser Ile Lys Leu Leu Leu Leu Ser
                  85                        90                    95

Ala Ala Glu Arg Pro Pro Ser Ala Phe Glu Val Lys Leu Asp Ile Ser
                100                      105                  110

Gly Lys Val Asp Val Glu Lys Leu Ile Gln Pro Ser Leu Asp Ser His
         115                    120                    125

Ile Gln Leu Ile Ser Gln Lys Asn Lys Leu Glu Glu Lys Val Arg Lys
130                      135                    140

Phe Ile Phe Lys Lys Glu Arg Phe Gln Leu Gln Leu Lys Asn Lys Ser
145                      150                    155                    160

Tyr Glu Pro Ile Ile Phe Gly Thr Trp Asn Gly Pro Lys Thr Ser Trp
                165                      170                  175

Leu Ile Lys Gly Gln Gly Lys Thr Asp Asp Glu Ile Pro Asp Ile Tyr
                  180                      185                  190

Val Ile Gly Leu Gln Phe Ala Glu Leu Ser Ala Leu Lys Gln Glu Trp
        195                    200                    205

Phe Ala Ser Gly Leu Thr Asp Tyr Lys Lys Val Ala Leu Leu Lys Thr
    210                        215                    220

Leu Gly Ile Met Leu Leu Ile Phe Lys Glu His Glu Asn Ile Ser His
225                      230                    235                    240

Ile Glu Thr Thr Val Lys Thr Gly Ile Gly Gly Asn Lys Gly Ala Val

-continued

```
                    245                 250                 255
Val Arg Phe Phe Thr Ser Phe Val Asn Ser His Leu Ala Ala Gly
            260                 265                 270

Glu Asn Tyr Glu Arg Arg Asn Cys Asp Tyr Lys Asp Ile Arg Arg Ser
        275                 280                 285

Phe Gly Asp Pro Leu Leu Arg Ile Thr His Ile Phe Trp Phe Gly
        290                 295                 300

Asp Leu Asn Tyr Arg Asp Met Asp Glu Glu Val Leu Ile Lys Arg Lys
305                 310                 315                 320

Glu Gln Arg Leu Leu Glu Tyr Asp Gln Leu Asn Arg Thr Gly Lys Phe
                325                 330                 335

Leu Gly Phe Glu Gly Glu Ile Thr Phe Pro Pro Thr Tyr Lys Tyr Arg
            340                 345                 350

Gly Arg Asp Tyr Ala Tyr Lys Gln Lys Asp Thr Ser Glu Lys Thr Arg
                355                 360                 365

Val Pro Ala Trp Cys Asp Arg Ile Leu Trp Lys Gly Thr Gln Leu Val
            370                 375                 380

Cys Ser Tyr Gly Ser Met Asp Ile Thr Ser Asp His Lys Pro Val Phe
385                 390                 395                 400

Ala Thr Phe Arg Ile Gly Val Thr Gln Phe Val Ser Lys Val Val Glu
                405                 410                 415

Thr Leu Tyr Arg Gln Ile Glu Glu Val Arg Ile Ser Arg Val Leu Phe
                420                 425                 430

Arg Phe Cys Glu Lys Glu Ser Asn Val Lys Phe Val Phe Ser Glu
            435                 440                 445

Pro Lys Gln Leu Leu Tyr Cys Lys Ser Asp Ala Glu Tyr Gly Lys Ala
450                 455                 460

Leu Lys Leu Glu Pro Thr Ala Ile Leu Thr Leu Val His Lys Gly
465                 470                 475                 480

Glu Leu Thr Gly Leu Ser Gly Glu Asp Lys Ile Asp Ile Val Leu His
                485                 490                 495

Leu Arg Lys Tyr Phe Leu Ser Gly Asn Pro Ser Cys Phe Gly Thr Ser
            500                 505                 510

Leu Cys Glu Pro Ile Pro Thr Glu Leu Cys Ser Leu Ser Glu Asp Glu
        515                 520                 525

Gly Pro Pro Pro Glu Trp Val Asp Leu Pro Ala Pro Gln Glu Asp Leu
530                 535                 540

Phe Gln Gln Pro Glu Leu Ile Asp Cys Leu Asp Thr Ser Pro Ala Ser
545                 550                 555                 560

Asn His Ser Val Ala Ala Leu Leu Pro Leu Leu Pro Pro Val Ile
                565                 570                 575

Cys Tyr Cys Leu Ala Thr Pro Ala Val Ile Ser Leu Pro Arg Phe His
                580                 585                 590

Asn Val Phe Tyr Leu Met Phe Leu Arg Glu Leu Lys Pro Pro Asn Asn
            595                 600                 605

Pro Ala Ile Ser Leu Leu Arg Pro Ala Gly Ala Arg Gly Pro Pro Lys
        610                 615                 620

Gln Pro Phe Leu Phe Leu Cys Ser Ser Ala Gly Asp Ser Lys Thr Ser
625                 630                 635                 640

Leu Pro Pro Gly Ser Thr Pro Pro Gly Arg Gly Arg Cys Ala
                645                 650
```

GRB2 ASSOCIATING POLYPEPTIDES AND NUCLEIC ACIDS ENCODING THEREFOR

The present invention generally relates to novel GRB2 associating polypeptides and nucleic acids which encode these polypeptides. In particular, these novel polypeptides possess inositol polyphosphate 5-phosphatase activity, important in growth factor mediated signal transduction. As such, the polypeptides, nucleic acids encoding the polypeptides, cells capable of expressing these nucleic acids and antibodies specific for the polypeptides will find a variety of uses in a wide range of screening, therapeutic and other applications.

The present invention was made with government support under Grant Nos. HL32898 and HL16634, awarded by the National Institutes of Health. The government has certain rights in this invention.

BACKGROUND OF THE INVENTION

Receptor signaling pathways are the subject of widespread research efforts. A better understanding of these signaling pathways will lead to the design of new and more effective drugs in the treatment of many diseases. Of particular interest are the growth factor and related receptor signaling pathways and their role in cell growth and differentiation. Binding of a particular growth factor to its receptor on the cell plasma membrane can stimulate a wide variety of biochemical responses, including changes in ion fluxes, activation of various kinases, alteration of cell shape, transcription of various genes and modulation of enzymatic activities in cellular metabolism.

Growth factors play a role in embryonic development, cancer, atherosclerosis and the responses of tissues to injury. Growth factors are involved in several normal developmental processes as well as in pathological conditions. Many growth factor receptors are tyrosine kinases whose signalling is dependent upon tyrosine phosphorylation of both the receptor and other molecules. Specific phosphorylated tyrosine residues on these receptors recruit soluble intracellular signaling molecules to the complex upon growth factor stimulation, thus initiating the growth factor signaling cascade. The signal can then proceed through a series of steps to the nucleus and other subcellular locations where the final effects of activation by the extracellular ligand are produced. Recruitment of molecules is often carried out by adapter molecules containing only protein-protein interaction domains with no associated enzymatic activity. By examining the molecules that interact with these adapters, important parts of the signaling mechanism can be discovered, monitored and controlled. One such adapter protein is GRB2, a 24 kDa cytosolic adapter protein containing two SH3 domains flanking an SH2 domain, which is known to be involved in linking many important molecules in signal transduction.

Because disregulation of the cellular processes involved in cell growth can have disastrous effects, it is important to understand and gain control over these processes. This requires identifying the participants in the signaling events that lead to mitogenesis and elucidating their mechanism of function. The identification of these participants is important for a wide range of diagnostic, therapeutic and screening applications. In particular, by knowing the structure of a particular participant in a growth factor activation cascade, one can design compounds which affect that cascade, to either activate an otherwise inactive pathway, or inactivate an overly active pathway. Similarly, having identified a particular participant in a growth factor cascade, one can also identify situations where that cascade is defective, resulting in a particular pathological state. The identification of participants in particular growth factor activation cascades is thus of critical importance for screening compounds that affect these cascades and treating a variety of disorders resulting from anomalies in these cascades, both as therapeutic agents and as model systems for identification of compounds which affect the pathway and thus may be useful as therapeutic agents. The present invention meets these and many other needs.

SUMMARY OF THE INVENTION

The present invention generally provides substantially pure polypeptides, comprising an amino acid sequence that is substantially homologous to the amino acid sequence shown in FIG. 10 (SEQ ID NO:2), or biologically active fragments thereof.

The present invention also provides isolated nucleic acid segments, which encode a polypeptide having an amino acid sequence substantially homologous to the amino acid sequence shown in FIG. 10 (SEQ ID NO:2), or biologically active fragments thereof.

Also provided are isolated antibodies that are specifically immunoreactive with a polypeptide having an amino acid sequence substantially homologous to the amino acid sequence shown in FIG. 10 (SEQ ID NO:2) or its biologically active fragments.

In a further aspect, the present invention provides methods of using these polypeptides. In particular, the invention provides a method of determining whether a test compound is an agonist or antagonist of a GRB2/GA5Ptase interaction. The method comprises contacting GRB2 with GA5Ptase (SEQ ID NO:2) under conditions conducive to forming a GRB2/GA5Ptase complex, in the presence and absence of the test compound. The amount of GRB2/GA5Ptase complex formed in the presence and absence of the test compound is then determined. An increase or decrease in the amount of GRB2/GA5Ptase complex formed in the presence of the test compound is indicative that the test compound is an agonist or antagonist of GRB2/GA5Ptase interaction, respectively.

In a related aspect, the present invention provides a method for determining whether a test compound is an agonist or antagonist of an inositol polyphosphate 5-phosphatase activity. The method comprises incubating a mixture of inositol polyphosphate substrate and GA5Ptase, in the presence and absence of the test compound. The mixture is then assayed to determine the amount of GA5Ptase product formed in the presence and absence of the test compound. The amount of product of GA5Ptase activity in the presence of the test compound is compared to the amount of product of GA5Ptase activity in the absence of the test compound. An increase or decrease in the amount of product of GA5Ptase activity in the presence of the test compound is indicative that the test compound is an agonist or antagonist of an inositol polyphosphate 5-phosphatase activity, respectively.

The present invention also provides a method of identifying the presence of GRB2 in a sample. The method comprises incubating the sample with the polypeptide of the invention, and detecting binding between the polypeptide and a portion of the sample. This binding is indicative of the presence of GRB2 in the sample.

Also provided is a method of purifying GRB2 from a mixture of different proteins containing GRB2. The method comprises immobilizing the polypeptide of the invention, on a solid support. The mixture of proteins is then contacted with the solid support under conditions in which the polypeptide binds GRB2. The solid support is washed to remove unbound proteins, and GRB2 is eluted from the solid support.

The present invention also provides kits for practicing these methods.

In a further aspect, the present invention provides a method of treating a patient suffering from a proliferative disorder. The method comprises administering to the patient a therapeutically effective amount of the polypeptide of the invention.

The present invention also provides substantially pure polypeptides that are immunologically cross-reactive with antibodies to the GA5ptase polypeptides and fragments, described herein.

BRIEF DESCRIPTION OF THE DRAWINGS

FIG. 8A shows conversion of $^3$H-Ins(1,3,4,5)P$_4$ to $^3$H-Ins(1,3,4)P$_3$ (peak) in the presence of GA5Ptase.

FIG. 8B shows the conversion of $^3$H-Ins(1,3,4,5)P$_4$ to $^3$H-Ins(3,4)P$_2$ (peak), in the presence of GA5Ptase and inositol polyphosphate 1-phosphatase.

FIG. 8C shows the conversion of $^3$H-Ins(1,3,4,5)P$_4$ to $^3$H-Ins(1,3)P$_2$ (peak) in the presence of GA5Ptase and inositol polyphosphate 4-phosphatase.

FIG. 10 shows the nucleotide sequence (SEQ ID NO:1) and deduced amino acid sequence (SEQ ID NO:2) of the GRB2 associating protein GA5Ptase.

FIG. 11 shows a comparison between the amino acid sequence of GA5Ptase (SEQ ID NO:2) and that of a number of other inositol polyphosphate 5-phosphatases. Level of shading indicates similarity in residue structure. Black boxes indicate a consensus sequence. The sequences shown are C. elegans inositol polyphosphate 5-phosphatase ("celegptase") (SEQ ID NO:3), S. cereviseae inositol polyphosphate 5-phosphatase ("ysc5ptase") (SEQ ID NO:4), GA5Ptase (SEQ ID NO:2), human 51c ("51c") (SEQ ID NO:5), human inositol polyphosphate 5-phosphatase 75 kDa ("5ptaseii") (SEQ ID NO:6), human ocr1 protein responsible for human oculocerebrorenal syndrome ("ocr1") (SEQ ID NO:7), Arabidopsis inositol polyphosphate 5-phosphatase ("arab5ptase") (SEQ ID NO:8) and canine inositol polyphosphate 5-phosphatase 43 kDa ("h5ptase43") (SEQ ID NO:9). The identified consensus sequence is also provided ("consensus") (SEQ ID NO:10).

DESCRIPTION OF THE PREFERRED EMBODIMENT

I. General Description

Figure 1:
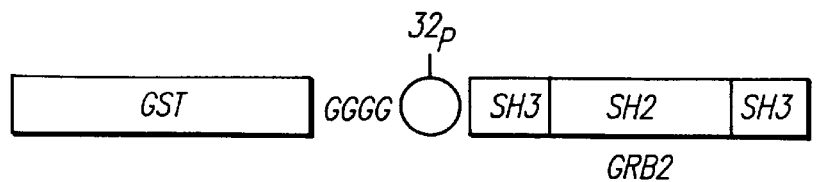
FIG. 1 shows a schematic representation of the probe used to screen a λgt11 expression library.

The present invention generally provides novel GRB2 associating polypeptides. These polypeptides are generally involved in signal transduction pathways following growth factor activation. In particular, the polypeptides of the present invention contribute to the mediation of inositol polyphosphate based signal transduction pathways, following growth factor activation.

Also provided by the present invention are nucleic acids encoding these novel polypeptides, expression vectors containing these nucleic acids, cells capable of expressing these expression vectors, antibodies which specifically recognize and bind these polypeptides and methods of using these polypeptides and nucleic acids in screening and therapeutic applications.

The polypeptides of the present invention have been identified as possessing unique specificity for inositol polyphosphates. In particular, the polypeptides of the present invention have inositol polyphosphate 5-phosphatase activity, and more particularly, the ability to remove the 5-phosphate from D-myo-Inositol 1,3,4,5-tetrakisphosphate ("Ins(1,3,4,5)P$_4$") and Phosphatidylinositol 3,4,5-trisphosphate ("PtdIns(3,4,5)P$_3$"), but not D-myo-Inositol 1,4,5-trisphosphate ("Ins(1,4,5)P$_3$") or Phosphatidylinositol (4,5)-bisphosphate ("PtdIns(4,5)P2"). Accordingly, the polypeptides of the present invention are generally referred to herein by the abbreviation GA5Ptase, for GRB2 Associating inositol polyphosphate 5-phosphatase.

Inositol polyphosphates have been broadly implicated in cell signalling pathways. For example, stimulation of cell surface receptors has been found to initiate hydrolysis of membrane-bound inositol lipid, which produces at least two second messengers: diacylglycerol (DAG) and inositol(1,4, 5)trisphosphate. These messengers are generated by a membrane transduction process which comprises three main components: a receptor, a coupling G protein and phosphoinositidase C. DAG acts by stimulating protein kinase C, whereas Ins(1,4,5)P$_3$ releases calcium from internal stores (see, Berridge and Irvine, Nature (1989) 341:197–205).

PtdIns(3,4,5)P$_3$ in particular, is the product of phosphatidyl inositol 3-kinase ("PI3 kinase"), an important agonist activated signaling protein, stimulated in growth factor mediated signal transduction. PI3-kinase is known to be involved in the regulation of cell growth and oncogenic transformation (Cantley et al., Cell, 64:1657 (1993)). Upon growth factor receptor stimulation, the wild-type PI3-kinase is activated and can phosphorylate phosphatidylinositol ("PtdIns") at the 3' position of the inositol ring. These phosphatidylinositol 3-phosphates are candidate second messenger molecules. The PI3-kinase enzyme is found associated with receptor protein tyrosine kinases such as PDGF-R-β, CSF-1 receptor, Insulin receptor and IGF-1 receptor as well as non-receptor tyrosine kinase oncogenes, e.g., src, gag-abl and fyn. Studies on mutants of platelet-derived growth factor (PDGF) receptor have shown that PI3-kinase is a key mediator of PDGF-mediated mitogenic signaling (Fantl et al., Cell, 69:413 (1992); Valius et al., ibid., 73:321 (1993)). PDGF-R mutants that are unable to bind PI3-kinase are also unable to induce a mitogenic response after growth factor stimulation and unable to activate p21c-Ras (Ras). These data indicate that PI3-kinase acts upstream of Ras in PDGF-stimulated signaling. Studies also indicate that the PI3-kinase product, PtdIns(3,4,5)P$_3$ is not the final product produced during the initial phases of signaling, indicating further processing of this signaling molecule. Stephens, et al., Nature 351:33–39 (1991), Hawkins, et al., Nature 358:157–159 (1992).

The action of the polypeptides of the present invention upon the specific product of PI3-kinase implicates these polypeptides as important downstream mediators of growth factor activation signaling cascades. Furthermore, in addition to inositol polyphosphate 5-phosphatase activity, the polypeptides of the invention also associate with GRB2, in cell culture. GRB2 is an intracellular signalling molecule that is recruited to the cell membrane/receptor complex upon growth factor stimulation. GRB2 is specifically recruited to the PDGF, EGF and other tyrosine growth factor receptors. It is also in the signaling pathway that activates Ras upon growth factor stimulation. GRB2 is a small protein (24 kDa) that functions as an adapter molecule using its two SH3 domains and single SH2 domain to provide a bridge between other important signaling molecules. Clark, et al., Nature 356:340–344 (1992), Stern, et al., Mol. Biol. Cell 4:1175–1188 (1993). The ability of the polypeptides of the invention to specifically associate with GRB2 further indicates the importance of these polypeptides as downstream mediators of growth factor activation signal transduction, generally.

The polypeptides of the present invention have also been shown to activate signaling through the Fos serum response element (SRE) in fibroblast cells when these polypeptides are co-expressed with GRB2 and c-Ras. This activation is four to six fold over the activation seen with GRB2, Ras or GRB2/Ras alone. The Fos SRE is a gene that is known to be turned on early in growth factor activation, and has been identified as an upstream event for many response elements for cell growth. See, e.g., Janknecht et al., Carcinogenesis 16(3)443–450 (1995), Piechaczyk et al., Crit. Rev. Oncol./Hematol. 17(2):93–131 (1994), Maruta et al., Bioessays 16(7):489–496 (1994). The Fos gene is also responsive to a large number of growth factors. In particular, the Fos SRE is believed to be the direct target induced by growth factor stimulation through the Ras oncogene.

The combination of the activities and specificities of the polypeptides of the present invention implicates these polypeptides as key elements in the activation of Ras and as downstream molecules generally, in agonist activated signal transduction cascades.

II. Proteins and Polypeptides of the Invention

In one aspect, the present invention provides substantially pure, or isolated polypeptides that are generally characterized by one or more of the following activities: inositol polyphosphate 5-phosphatase activity; the ability to associate with GRB2; and/or the ability to enhance activation of the Fos SRE when co-expressed with c-Ras or c-Ras and GRB2. In particular, the polypeptides of the present invention will generally possess inositol polyphosphate 5-phosphatase activity, and be capable of removing the 5-phosphate from D-myo-Inositol 1,3,4,5-tetrakisphosphate ("Ins(1,3,4,5)P$_4$") and Phosphatidylinositol 3,4,5-trisphosphate ("PtdIns(3,4,5)P$_3$"), but not D-myo-Inositol 1,4,5-trisphosphate ("Ins(1,4,5)P$_3$") or Phosphatidylinositol (4,5)-bisphosphate ("PtdIns(4,5)P$_2$").

The terms "substantially pure" or "isolated", when referring to proteins and polypeptides, denotes those polypeptides that are separated from proteins or other contaminants with which they are naturally associated. A protein or polypeptide is considered substantially pure when that protein makes up greater than about 50% of the total protein content of the composition containing that protein, and typically, greater than about 60% of the total protein content. More typically, a substantially pure protein will make up from about 75 to about 90% of the total protein. Preferably, the protein will make up greater than about 90%, and more preferably, greater than about 95% of the total protein in the composition.

Particularly preferred polypeptides will have an amino acid sequence that is substantially homologous to the amino acid sequence shown in FIG. 10 (SEQ ID NO:2), or biologically active fragments thereof. Still more preferred polypeptides include the GA5Ptase protein (SEQ ID NO:2) or biologically active fragments thereof.

In describing the polypeptides of the present invention, conventional amino acid abbreviations will generally be used as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. In the polypeptide notation used herein, the lefthand direction is the amino terminal direction and the righthand direction is the carboxy-terminal direction, in accordance with standard usage and convention.

The term "biologically active fragment" as used herein, refers to portions of the proteins or polypeptides which portions possess a particular biological activity. For example, such biological activity may include the ability to bind a particular protein or substrate, block or otherwise inhibit an interaction between two proteins or between an enzyme and its substrate, or may include a particular catalytic activity. With regard to the polypeptides of the present invention, particularly preferred polypeptides or biologically active fragments include, e.g., polypeptides that possess one or more of the biological activities described above, such as the ability to associate or bind GRB2 or affect the binding of GRB2 to its ligand, e.g., GA5Ptase. Also included are those fragments that bind the GA5Ptase substrates described above, are capable of affecting the binding of GA5Ptase to those substrates or that are capable of affecting the hydrolysis of those substrates. Fragments possessing this catalytic activity are also termed "catalytically active fragments." Fragments that are specifically recognized and bound by antibodies raised against the GA5Ptase polypeptides are also included in the definition of biologically active fragments. Such fragments are also referred to herein as "immunologically active fragments." Particularly preferred polypeptides or biologically active fragments are capable of enhancing the activation of Fos SRE when co-expressed with Ras or Ras and GRB2.

Biologically active fragments of the polypeptides of the invention will generally be useful where it is desired to analyze a single particular biological activity of the polypeptide. For example, where the fragment is used in a model to screen for agonists or antagonists of GA5Ptase/GRB2 interaction (discussed in greater detail, below), it may be desirable to utilize only the GRB2 binding portion of the polypeptides of the invention. Similarly, therapeutic applications will generally target a single biological activity of the GA5Ptase signaling operation, e.g. GRB2 binding, substrate binding or substrate catalysis, and as such, peptides having fewer than all of these activities will be desired, as discussed in greater detail, below. Alternatively, such fragments may be useful where use of a full length protein is unsuitable for the particular application, e.g. therapeutic treatments where administration of full length proteins is difficult.

Generally, biologically active fragments of the above described proteins will be from about 5 to about 1000 amino acids in length. Typically, these peptides will be from about 10 to about 500 amino acids in length, more typically about 20 to about 250 amino acids in length, and preferably from about 50 to about 200 amino acids in length. Generally, the length of the fragment may depend, in part, upon the application for which the particular peptide is to be used. For example, for raising antibodies, the peptides may be of a shorter length, e.g., from about 5 to about 50 amino acids in length, whereas for binding applications, the peptides will generally have a greater length, e.g., from about 50 to about 1000 amino acids in length, preferably, from about 100 to about 500 amino acids in length, and more preferably, from about 100 to about 200 amino acids in length.

The terms "substantially homologous" when referring to polypeptides, refer comparatively to two amino acid sequences which, when optimally aligned, are at least about 75% homologous, preferably at least about 85% homologous more preferably at least about 90% homologous, and still more preferably at least about 95% homologous. Optimal alignment of sequences for aligning a comparison window may be conducted by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Natl. Acad. Sci.* (USA) 85:2444, or by computerized implementations of these algorithms (GAP, BESTFIT, FASTA, and TFASTA in the Wisconsin Genetics Software Package Release 7.0, Genetics Computer Group, 575 Science Dr., Madison, Wis.).

The polypeptides of the present invention may also be characterized by their ability to bind antibodies raised against proteins having the amino acid sequence shown in FIG. 10 (SEQ ID NO:2). These antibodies recognize polypeptides that are homologous to the GA5Ptase polypeptide (SEQ ID NO:2). A variety of immunoassay formats may be used to select antibodies specifically immunoreactive with a particular protein or domain. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity. Antibodies to the polypeptides of the present invention are discussed in greater detail, below.

The polypeptides of the present invention may generally be prepared using recombinant or synthetic methods well known in the art. Recombinant techniques are generally described in Sambrook, et al., *Molecular Cloning: A Laboratory Manual*, (2nd ed.) Vols. 1–3, Cold Spring Harbor Laboratory, (1989). Techniques for the synthesis of polypeptides are generally described in Merrifield, *J. Amer. Chem. Soc.* 85:2149–2456 (1963), Atherton, et al., Solid Phase Peptide Synthesis: *A Practical Approach*, IRL Press (1989), and Merrifield, Science 232:341–347 (1986). In preferred aspects, the polypeptides of the present invention may be expressed by a suitable host cell that has been transfected with a nucleic acid of the invention, as described in greater detail below.

Biologically active fragments of the above described polypeptides may generally be identified and prepared using methods well known in the art. For example, selective proteolytic digestion, recombinant deletional methods or de novo peptide synthesis methods may be employed to identify portions of the above described peptides that possess the desired biological activity, e.g., GRB2 binding, substrate binding, catalytic activity and the like. See, e.g. Sambrook, et al.

Isolation and purification of the polypeptides of the present invention can be carried out by methods that are generally well known in the art. For example, the polypeptides may be purified using readily available chromatographic methods, e.g., ion exchange, hydrophobic interaction, HPLC or affinity chromatography, to achieve the desired purity. Affinity chromatography may be particularly attractive in allowing the investigator to take advantage of the specific biological activity of the desired peptide, e.g., ligand binding, presence of antigenic determinants or the like. For example, the polypeptides of the present invention may be purified by taking advantage of their ability to associate with GRB2. Such affinity purification methods are well known in the art. In particular, GRB2 may be coupled to a suitable solid support and contacted with a mixture of proteins containing the polypeptides of the invention under conditions conducive the association of these polypeptides with GRB2. Once bound to the immobilized GRB2, the solid support is washed to remove unbound material and/or nonspecifically bound proteins. The polypeptides of the invention may then be eluted from the solid support in substantially pure form by, e.g. a change in salt, pH or buffer concentration. Suitable solid supports for affinity purifications are well known in the art and are generally commercially available from, e.g. Pharmacia, Inc., or Sigma Chemical Co. Examples of such solid supports include agarose, cellulose, dextran, silica, polystyrene or similar solid supports.

In addition to those polypeptides and fragments described above, the present invention also provides fusion proteins which contain these polypeptides or fragments. The term "fusion protein" as used herein, generally refers to a composite protein, i.e., a single contiguous amino acid sequence, made up of two distinct, heterologous polypeptides which are not normally fused together in a single amino acid sequence. Thus, a fusion protein may include a single amino acid sequence that contains two similar or identical polypeptide sequences, provided that these sequences are not normally found together in a single amino acid sequence. Fusion proteins may generally be prepared using either recombinant nucleic acid methods, i.e. as a result of transcription and translation of a gene fusion, which fusion comprises a segment encoding a polypeptide of the invention and a segment encoding a heterologous protein, or by chemical synthesis methods well known in the art.

These fusion proteins may be prepared to exhibit a combination of properties or activities of the derivative proteins. Typical fusion proteins may include a polypeptide of the invention fused to a reporter polypeptide, e.g., a substrate, cofactor, inhibitor, affinity ligand, antibody binding epitope tag, or an enzyme which is capable of being assayed. Because of their ability to associate with the GRB2 protein, the polypeptides of the invention, when included as a portion of the fusion protein, may act as an affinity ligand to direct the activity of the fused protein directly to the GRB2 protein. In the case of a fusion protein including a reporter group, this allows the presence and or location of the GRB2 protein to be determined. More importantly, such fusions can also be readily used as a marker for determining the level of fusion protein/GRB2 interaction. Examples of some useful fusion partners which can also serve as reporter groups include affinity ligands and antibody binding epitopes, such as the influenza virus hemagglutinin (IHA) epitope tag, or glutathione-S-transferase. Other typical fusion partners include bacterial β-galactosidase, trpE, protein A, β-lactamase, α-amylase, alcohol dehydrogenase and yeast α-mating factor. See, e.g., Godowski et al., *Science* 241:812–816 (1988).

Also included within the present invention are amino acid variants of the above described polypeptides. These variants may include insertions, deletions and substitutions with other amino acids. For example, in some aspects, amino acids may be substituted with different amino acids having similar structural characteristics, e.g. net charge, hydrophobicity, or the like. For example, phenylalanine may be substituted with tyrosine, as a similarly hydrophobic residue. Glycosylation modifications, either changed, increased amounts or decreased amounts, as well as other sequence modifications are also envisioned.

Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo and Gierasch (1992) *Ann. Rev. Biochem.* 61: 387; for example, by adding internal cysteine residues capable of forming intramolecular disulfide bridges which cyclize the peptide. Similarly, modification of the amino or carboxy terminals may also be used to confer stabilizing properties upon the polypeptides of the invention, e.g., amidation of the carboxy-terminus or acylation of the amino-terminus. Substitution of amino acids involved in catalytic activity can be used to generate dominant negative inhibitors of signaling pathways.

Furthermore, although primarily described in terms of "proteins" or "polypeptides" one of skill in the art, upon reading the instant specification, will appreciate that these terms also include structural analogs and derivatives of the above-described polypeptides, e.g., polypeptides having conservative amino acid insertions, deletions or substitutions, peptidomimetics and the like. For example, in addition to the above described polypeptides which consist only of naturally-occurring amino acids, peptidomimetics of the polypeptides of the present invention are also provided. Peptide analogs are commonly used in the pharmaceutical industry as non-peptide drugs with properties analogous to those of the template peptide. These types of non-peptide compounds are termed "peptide mimetics" or "peptidomimetics" (Fauchere, J. (1986) *Adv. Drug Res.* 15:29; Veber and Freidinger (1985) *TINS* p.392; and Evans et al. (1987) *J. Med. Chem* 30:1229, and are usually developed with the aid of computerized molecular modeling. Peptide mimetics that are structurally similar to therapeutically useful peptides may be used to produce an equivalent therapeutic effect. Generally, peptidomimetics are structurally similar to a paradigm polypeptide (i.e., a polypeptide that has a biological or pharmacological activity), such as naturally-occurring receptor-binding polypeptide, but have one or more peptide linkages optionally replaced by a linkage selected from the group consisting of: —CH$_2$NH—, —CH$_2$S—, —CH$_2$—CH$_2$—, —CH=CH— (cis and trans), —COCH$_2$—, —CH(OH)CH$_2$—, and —CH$_2$SO—, by methods known in the art and further described in the following references: Spatola, A. F. in *Chemistry and Biochemistry of Amino Acids, Peptides, and Proteins*, B. Weinstein, eds., Marcel Dekker, New York, p. 267 (1983); Spatola, A. F., Vega Data (March 1983), Vol. 1, Issue 3, "Peptide Backbone Modifications" (general review); Morley, J. S., *Trends Pharm Sci* (1980) pp. 463–468 (general review); Hudson, D. et al., *Int J Pept Prot Res* (1979) 14:177–185 (—CH$_2$NH—, CH$_2$CH$_2$—); Spatola, A. F. et al., *Life Sci* (1986) 38:1243–1249 (—CH$_2$—S); Hann, M. M., *J Chem Soc Perkin Trans I* (1982) 307–314 (—CH—CH—, cis and trans); Almquist, R. G. et al., *J Med Chem* (1980) 23:1392–1398 (—COCH$_2$—); Jennings-White, C. et al., *Tetrahedron Lett* (1982) 23:2533 (—COCH$_2$—); Szelke, M. et al., European Appln. EP 45665 (1982) CA: 97:39405 (1982) (—CH(OH)CH$_2$—); Holladay, M. W. et al., *Tetrahedron Lett* (1983) 24:4401–4404 (—C(OH)CH$_2$—); and Hruby, V. J., *Life Sci* (1982) 31:189–199 (—CH$_2$—S—).

Peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others.

For many applications, it may be desirable to provide the polypeptides of the invention as labeled entities, i.e., covalently attached or linked to a detectable group, to facilitate identification, detection and quantification of the polypeptide in a given circumstance. These detectable groups may comprise a detectable protein group, e.g. an assayable enzyme or antibody epitope as described above in the discussion of fusion proteins. Alternatively, the detectable group may be selected from a variety of other detectable groups or labels, such as radiolabels (e.g., $^{125}$I, $^{32}$P or $^{35}$S) or a chemiluminescent or fluorescent group. Similarly, the detectable group may be a substrate, cofactor, inhibitor or affinity ligand. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the molecules to which the peptidomimetic binds (e.g., GRB2) to produce the therapeutic effect. Derivitization (e.g., labeling) of peptidomimetics should not substantially interfere with the desired biological or pharmacological activity of the peptidomimetic. Generally, peptidomimetics of peptides of the invention bind to their ligands (e.g., GRB2) with high affinity and/or possess detectable biological activity (i.e., are agonistic or antagonistic to one or more inositol polyphosphate 5-phosphatase mediated phenotypic changes).

III. Pharmaceutical Compositions

For a variety of applications, it may be desirable to provide the polypeptides or polypeptide fragments of the invention as part of a pharmaceutical composition, e.g., in combination with a pharmaceutically acceptable carrier. In such pharmaceutical compositions, the polypeptide of the present invention is also referred to as "the active ingredient." Pharmaceutical formulations suitable for use in the present invention are generally described in *Remington's Pharmaceutical Sciences*, Mack Publishing Co., 17th ed. (1985).

The pharmaceutical compositions of the present invention are intended for parenteral, topical, oral, or local administration. Where the pharmaceutical compositions are administered parenterally, the invention provides pharmaceutical compositions that comprise a solution of the agents described above, e.g., proteins or polypeptides of the invention, dissolved or suspended in a pharmaceutically acceptable carrier, preferably an aqueous carrier. A variety of aqueous carriers may be used, e.g., water, buffered water, saline, glycine and the like. These compositions may be sterilized by conventional, well known methods, e.g., sterile filtration. The resulting aqueous solutions may be packaged for use as is, or lyophilized for combination with a sterile solution prior to administration. The compositions may also contain pharmaceutically acceptable auxiliary substances as required to approximate physiological conditions, such as pH adjusting and buffering agents, tonicity adjusting agents, wetting agents, and the like, for example sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose starch, magnesium stearate, sodium saccharin, talcum, cellulose, glucose, sucrose, magnesium carbonate, and the like. For oral administration, a pharmaceutically acceptable nontoxic composition may be formed by incorporating any of the normally employed excipients, such as the previously listed carriers, and generally, 10–95% of active ingredient, and more preferably 25–75% active ingredient. In addition, for oral administration of peptide based compounds, the pharmaceutical compositions may include the active ingredient as part of a matrix to prevent proteolytic degradation of the active ingredient by digestive process, e.g., by providing the pharmaceutical composition within a liposomal composition, according to methods well known in the art. See, e.g., *Remington's Pharmaceutical Sciences*, Mack Publishing Co., 17th Ed. (1985).

For aerosol administration, the polypeptides are generally supplied in finely divided form along with a surfactant or propellant. Preferably, the surfactant will be soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids, with an aliphatic polyhydric alcohol or its cyclic anhydride. Mixed esters, such as mixed or natural glycerides may be employed. A carrier can also be included, as desired, as with, e.g., lecithin for intranasal delivery.

The amount of the above compositions to be administered to the patient will vary depending upon what is to be administered to the patient, the state of the patient, and the manner of administration. Typically, the polypeptides are administered in an amount sufficient to affect the growth factor activation cascade, and thereby cure or at least partially arrest the symptoms of the disease which is sought to be treated, and its associated complications. An amount adequate to accomplish this is termed "a therapeutically effective amount" as described below. Amounts effective for this use will depend many factors, including the severity of the disorder and the weight and general state of the patient, but will generally be in the range of from about 1 mg to about 5 g of active agent per day, preferably from about 50 mg per day to about 500 mg per day, and more preferably, from about 50 mg to about 100 mg per day, for a 70 kg patient.

IV. Nucleic Acids and Expression Vectors

In addition to the above described polypeptides, the present invention also provides isolated nucleic acids encoding these polypeptides, as well as expression vectors which include these polynucleotides. Generally, the isolated nucleic acids of the present invention encode a polypeptide which is capable of associating with GRB2, and/or possesses inositol polyphosphate 5-phosphatase activity. In preferred aspects, the nucleic acids of the invention encode a polypeptide having an amino acid sequence that is substantially homologous to the amino acid sequence shown in FIG. 10. More preferred are those isolated nucleic acid sequences that are substantially homologous to the nucleotide sequence shown in FIG. 10, or fragments thereof, and most preferred are those nucleic acid sequences having the nucleotide sequence shown in FIG. 10.

"Nucleic acids" of the present invention include RNA, cDNA, genomic DNA, synthetic forms and mixed polymers, both sense and antisense strands. Furthermore, different alleles of each isoform are also included. The present invention also provides recombinant nucleic acids which are not otherwise naturally occurring. The nucleic acids described herein also include self replicating plasmids and infectious polymers of DNA or RNA. Unless specified otherwise, conventional notation for nucleic acids is used herein. For example, as written, the left hand end of a single stranded polynucleotide sequence is the 5'-end, whereas the right-hand end is the 3'-end. The left hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The nucleic acids of the present invention may be present in whole cells, cell lysates or in partially pure or substantially pure or isolated form. When referring to nucleic acids, the terms "substantially pure" or "isolated" generally refer to the nucleic acid separated from contaminants with which it is generally associated, e.g., lipids, proteins and other nucleic acids. The substantially pure or isolated nucleic acids of the present invention will be greater than about 50% pure. Typically, these nucleic acids will be more than about 60% pure, more typically, from about 75% to about 90% pure, and preferably, from about 95% to about 98% pure.

The DNA compositions will generally include a coding region which encodes a polypeptide possessing inositol polyphosphate 5-phosphatase activity and capable of associating with GRB2. Preferred nucleic acids will typically encode polypeptides having an amino acid sequence which is substantially homologous to the amino acid sequence shown in FIG. 10 (SEQ ID NO:2), or biologically active fragments thereof. More preferred nucleic acids will comprise a segment having more than about 20 contiguous nucleotides from the nucleotide sequence shown in FIG. 10 (SEQ ID NO:1), with still more preferred nucleic acids having a nucleotide sequence that is substantially homologous to the nucleotide sequence shown in FIG. 10 (SEQ ID NO:1). Most preferred nucleic acids are those which include the nucleotide sequence shown in FIG. 10 (SEQ ID NO:1).

The phrase "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length protein. It being further understood that the sequence includes the degenerate codons of the native sequence or sequences which may be introduced to provide codon preference in a specific host cell.

Substantial homology in the nucleic acid context means that the segments, or their complementary strands, when compared, are the same when properly aligned, with the appropriate nucleotide insertions or deletions, in at least about 60% of the nucleotides, typically, at least about 70%, more typically, at least about 80%, usually, at least about 90%, and more usually, at least about 95% to 98% of the nucleotides. Alternatively, substantial homology exists when the segments will hybridize under selective hybridization conditions to a strand, or its complement, typically using a sequence of at least about 20 contiguous nucleotides derived from the nucleotide sequence shown in FIG. 10. However, larger segments will usually be preferred, e.g., at least about 30 contiguous nucleotides, more usually about 40 contiguous nucleotides, and preferably more than about 50 contiguous nucleotides. Selective hybridization exists when hybridization occurs which is more selective than total lack of specificity. See, Kanehisa, *Nucleic Acid Res.* 12:203–213 (1984).

There are various methods of isolating the nucleic acids which encode the polypeptides of the present invention. Typically, the DNA is isolated from a genomic or cDNA library using labeled oligonucleotide probes specific for sequences in the desired DNA. Restriction endonuclease digestion of genomic DNA or cDNA containing the appropriate genes can be used to isolate the DNA encoding the polypeptides of the invention. From the nucleotide sequence given in FIG. 10, a panel of restriction endonucleases can be constructed to give cleavage of the DNA in desired regions, i.e., to obtain segments which encode biologically active fragments of the polypeptides of the invention. Following restriction endonuclease digestion, DNA encoding the polypeptides of the invention is identified by its ability to hybridize with a nucleic acid probe in, for example a Southern blot format. These regions are then isolated using standard methods. See, e.g., Sambrook, et al., supra.

The polymerase chain reaction, or "PCR" can also be used to prepare nucleic acids which encode the polypeptides of the present invention. PCR technology is used to amplify nucleic acid sequences of the desired nucleic acid, e.g., the DNA which encodes the polypeptides of the invention, directly from mRNA, cDNA, or genomic or cDNA libraries. Alternatively, solid phase oligonucleotide synthesis methods may also be employed to produce the nucleic acids described herein. Such methods include the phosphoramidite method described by, e.g., Beaucage and Carruthers, *Tetrahedron Lett.* 22:1859–1862 (1981), or the triester method according to Matteucci, et al., *J. Am. Chem. Soc.*, 103:3185 (1981), both incorporated herein by reference. A double stranded fragment may then be obtained, if desired, by annealing the chemically synthesized single strands together under appropriate conditions or by synthesizing the complementary strand using DNA polymerase with an appropriate primer sequence.

Appropriate primers and probes for amplifying the nucleic acids described herein, may be generated from analysis of the nucleic acid sequences described herein, e.g. at FIG. 10. Briefly, oligonucleotide primers complementary to the two 3' borders of the DNA region to be amplified are synthesized. The PCR is then carried out using the two primers. See, e.g., *PCR Protocols: A Guide to Methods and Applications* (Innis, M., Gelfand, D., Sninsky, J. and White, T., eds.) Academic Press (1990). Primers can be selected to amplify various sized segments from the nucleic acid sequence.

The present invention also includes fragments of the above described nucleic acids. Such fragments will generally comprise a segment of from about 15 to about 150 nucleotides. These fragments can be useful as oligonucleotide probes in the methods of the present invention, or alternatively to encode the polypeptides or biologically active fragments of the present invention, described herein. Also provided are substantially similar nucleic acid sequences, allelic variations and natural or induced sequences of the above described nucleic acids. Also included are chemically modified and substituted nucleic acids, e.g., those which incorporate modified nucleotide bases or which incorporate a labelling group.

In one aspect, cDNA encoding the polypeptides of the present invention, or fragments thereof, may be readily employed as nucleic acid probes useful for obtaining genes which encode the polypeptides of the present invention. "Nucleic acid probes" may be DNA or RNA fragments. DNA fragments can be prepared, for example, by digesting plasmid DNA, or by use of PCR, or synthesized by either the phosphoramidite method described above. Where a specific sequence for a nucleic acid probe is given, it is understood that the complementary strand is also identified and included. The complementary strand will work equally well in situations where the target is a double-stranded nucleic acid.

Typical nucleic acid probes may be readily derived from the nucleotide sequence shown in FIG. 10 (SEQ ID NO:1), or alternatively, may be prepared from the amino acid sequence of the GA5Ptase protein, as shown in FIG. 10 (SEQ ID NO:2). In particular, probes may be prepared based upon segments of the amino acid sequence which possess relatively low levels of degeneracy, i.e., few or one possible nucleic acid sequences which encode therefor. Suitable synthetic DNA fragments may then be prepared. Such cDNA probes may be used in the design of oligonucleotide probes and primers for screening and cloning genes which encode the polypeptides of the invention or related polypeptides, e.g., using well known PCR techniques. These nucleic acids, or fragments may comprise part or all of the cDNA sequence that encodes the polypeptides of the present invention. Effective cDNA probes may comprise as few as 15 consecutive nucleotides in the cDNA sequence, but will often comprise longer segments. Further, these probes may further comprise an additional nucleotide sequence, such as a transcriptional primer sequence for cloning, or a detectable group for easy identification and location of complementary sequences.

cDNA or genomic libraries of various types may be screened for new alleles or related sequences using the above probes. The choice of cDNA libraries normally corresponds to tissue sources which are abundant in mRNA for the desired polypeptides. Phage libraries are normally preferred, but plasmid libraries may also be used. Clones of a library are spread onto plates, transferred to a substrate for screening, denatured, and probed for the presence of the desired sequences.

In addition to comprising a segment which encodes one or more of the above described polypeptides or biologically active fragments, the nucleic acids of the present invention may also comprise a segment encoding a heterologous protein, such that the gene is expressed to produce the two proteins as a fusion protein, as substantially described above.

Typically, the nucleic acids of the present invention will be used in expression vectors for the preparation of the polypeptides of the present invention, namely those polypeptides which possess inositol polyphosphate 5-phosphatase activity and that are capable of associating with GRB2. The phrase "expression vector" generally refers to nucleotide sequences that are capable of affecting expression of a structural gene in hosts compatible with such sequences. These expression vectors typically include at least suitable promoter sequences and optionally, transcription termination signals. Additional factors necessary or helpful in effecting expression may also be used as described herein. DNA encoding the polypeptides of the present invention will typically be incorporated into DNA constructs capable of introduction into and expression in an in vitro cell culture. Often, the nucleic acids of the present invention may be used to produce a suitable recombinant host cell. Specifically, DNA constructs will be suitable for replication in a prokaryotic host, such as bacteria, e.g., *E. coli*, or may be introduced into a cultured mammalian, plant, insect, yeast, fungi or other eukaryotic cell line. DNA constructs prepared for introduction into a particular host, e.g., bacteria or yeast, will typically include a replication system recognized by the host, the intended DNA segment encoding the desired polypeptide, and transcriptional and translational initiation and termination regulatory sequences operably linked to the polypeptide encoding segment. A DNA segment is operably linked when it is placed into a functional relationship with another DNA segment. For example, a promoter or enhancer is operably linked to a coding sequence if it stimulates the transcription of the sequence. DNA for a signal sequence is operably linked to DNA encoding a polypeptide if it is expressed as a preprotein that participates in the secretion of the polypeptide. Generally, DNA sequences that are operably linked are contiguous, and in the case of a signal sequence both contiguous and in reading phase. However, enhancers need not be contiguous with the coding sequences whose transcription they control. Linking is accomplished by ligation at convenient restriction sites or at adapters or linkers inserted in lieu thereof. The selection of an appropriate promoter sequence will generally depend upon the host cell selected for the expression of the DNA segment. Examples of suitable promoter sequences include prokaryotic, and eukaryotic promoters well known in the art. See, e.g., Sambrook et al., *Molecular Cloning: A Laboratory Manual* (2d ed.), vols. 1–3 Cold Spring Harbor Laboratory (1989). The transcriptional regulatory sequences will typically include a heterologous enhancer or promoter which is recognized by the host. The selection of an appropriate promoter will depend upon the host, but promoters such as the trp, lac and phage promoters, tRNA promoters and glycolytic enzyme promoters are known and available. See Sambrook et al., (1989).

Conveniently available expression vectors which include the replication system and transcriptional and translational regulatory sequences together with the insertion site for the polypeptide encoding segment may be employed. Examples of workable combinations of cell lines and expression vectors are described in Sambrook et al., and in Metzger et al., *Nature* 334:31–36 (1988). For example, where an insect host cell is selected as the host cell of choice to express the polypeptide, the cDNA encoding the polypeptides of the invention may be cloned into a baculovirus expression vector (e.g. pV-IKS). The recombinant baculovirus may then be used to transfect a suitable insect host cell, e.g., Sf9 cells, which may then express the polypeptide. See, e.g., D. K. Morrison et al., Cell 58:649–657 (1989), M. D. Summers and G. E. Smith, A Manual of Methods for Baculovirus Vectors and Insect Cell Culture Procedures, Texas Agricultural Station, College Station, Texas (1987).

V. Cell Lines

The vectors containing the DNA segments of interest, e.g., those encoding polypeptides of the invention as described above, can be transferred into the host cell by well known methods which may vary depending upon the type of host cell used. For example, calcium chloride transfection is commonly used for prokaryotic cells, whereas calcium phosphate treatment may be used for other hosts. See, Sambrook et al. The term "transformed cell" as used herein, includes the progeny of originally transformed cells, which progeny express the nucleic acids of the invention.

Techniques for manipulation of nucleic acids which encode the polypeptides of the present invention, i.e., subcloning the nucleic acids into expression vectors, labeling probes, DNA hybridization and the like, are generally described in Sambrook, et al., supra.

In recombinant methods, generally the nucleic acid encoding a peptide of the present invention is first cloned or isolated in a form suitable for ligation into an expression vector. After ligation, the vectors containing the nucleic acid fragments or inserts are introduced into a suitable host cell, for the expression of the polypeptide of the invention. The polypeptides may then be purified or isolated from the host cells. Methods for the synthetic preparation of oligonucleotides are generally described in Gait, *Oligonucleotide Synthesis: A Practical Approach*, IRL Press (1990).

VI. Antibodies The nucleic acids and polypeptides of the present invention or fragments thereof, are also useful in producing antibodies, either polyclonal or monoclonal, which are specifically immunoreactive with the polypeptides of the present invention.

The phrase "specifically immunoreactive," when referring to the interaction between an antibody of the invention and a particular protein, refers to an antibody that specifically recognizes and binds with relatively high affinity to the particular protein, such that this binding is determinative of the presence of the protein in a heterogeneous population of proteins and other biologics. Thus, under designated immunoassay conditions, the specified antibodies bind to a particular protein and do not bind in a significant amount to other proteins present in the sample. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

For production of polyclonal antibodies, an appropriate target immune system is selected, typically a mouse or rabbit, but also including goats, sheep, cows, guinea pigs, monkeys and rats. The substantially purified antigen or plasmid is presented to the immune system in a fashion determined by methods appropriate for the animal. These and other parameters are well known to immunologists. Typically, injections are given in the footpads, intramuscularly, intradermally or intraperitoneally. The immunoglobulins produced by the host can be precipitated, isolated and purified by routine methods, including affinity purification.

For monoclonal antibodies, appropriate animals will be selected and the desired immunization protocol followed. After the appropriate period of time, the spleens of these animals are excised and individual spleen cells are fused, typically, to immortalized myeloma cells under appropriate selection conditions. Thereafter, the cells are clonally separated and the supernatants of each clone are tested for the production of an appropriate antibody specific for the desired region of the antigen. Techniques for producing antibodies are well known in the art. See, e.g., Goding et al., *Monoclonal Antibodies: Principles and Practice* (2d ed.) Acad. Press, N.Y., and Harlow and Lane, *Antibodies: A Laboratory Manual*, Cold Spring Harbor Laboratory, New York (1988). Other suitable techniques involve the in vitro exposure of lymphocytes to the antigenic polypeptides or alternatively, to selection of libraries of antibodies in phage or similar vectors. Huse et al., Generation of Large Combinatorial Library of the Immunoglobulin Repertoire in Phage Lambda, *Science* 246:1275–1281 (1989). Monoclonal antibodies with affinities of $10^8$ liters/mole, preferably $10^9$ to $10^{10}$ or stronger, will be produced by these methods.

The antibodies generated can be used for a number of purposes, e.g., as probes in immunoassays, for inhibiting GRB2/GA5Ptase interaction, or interaction with other ligands, thereby inhibiting or reducing the growth factor signaling cascade, in diagnostics or therapeutics, or in research to further elucidate the mechanism of growth factor activation pathways, and particularly, the growth factor activation of Ras. Where the antibodies are used to block the interaction between two signaling molecules, e.g. GRB2 and GA5Ptase, the antibody will generally be referred to as a "blocking antibody."

The antibodies of the present invention can be used with or without modification. Frequently, the antibodies will be labeled by joining, either covalently or non-covalently, a substance which provides for a detectable signal. Such labels include those that are well known in the art, such as the labels described previously for the polypeptides of the invention. Additionally, the antibodies of the invention may be chimeric, human-like or humanized, in order to reduce their potential antigenicity, without reducing their affinity for their target. Chimeric, human-like and humanized antibodies have generally been described in the art. Generally, such chimeric, human-like or humanized antibodies comprise hypervariable regions, e.g., complementarity determining regions (CDRs) from a mammalian animal, i.e., a mouse, and a human framework region. See, e.g., Queen, et al., Proc. Nat'l Acad. Sci. USA 86:10029 (1989), Verhoeyan, et al., *Science* 239:1534–1536 (1988). By incorporating as little foreign sequence as possible in the hybrid antibody, the antigenicity is reduced. Preparation of these hybrid antibodies may be carried out by methods well known in the art.

Preferred antibodies are those monoclonal or polyclonal antibodies which specifically recognize and bind the polypeptides of the invention. Accordingly, these preferred antibodies will specifically recognize and bind the polypeptides which have an amino acid sequence that is substantially homologous to the amino acid sequence shown in FIG. 10 (SEQ ID NO:2). Still more preferred are antibodies which are capable of forming an antibody-ligand complex with the polypeptides of the invention, whereby the ability of the polypeptide to associate with GRB2, in vitro, is reduced, e.g. blocking antibodies.

VII. Methods of Use

The polypeptides, antibodies and nucleic acids of the present invention may be used in a variety of important applications. Such applications include but are not limited to screening applications for identifying compounds that affect the growth factor signal transduction pathways, also termed "signaling cascades," and therapeutic applications for the treatment of proliferative cell disorders.

A. Screening Applications

In a particular aspect, the present invention provides methods of screening test compounds to determine whether the test compounds are capable of affecting growth factor activation signal transduction pathways. More particularly, the methods described herein are used to screen compounds for there ability to affect the interaction of the polypeptides of the invention, and their respective substrates and ligands, as these interactions are involved in growth factor activation signal transduction pathways, and particularly, the growth factor activation of Ras.

In one aspect, the present invention provides methods of screening whether a test compound is an agonist or antagonist of GRB2-mediated signal transduction. More specifically, the polypeptides of the present invention can be used as a model system of GRB2/GA5Ptase interaction, to screen for compounds which affect this interaction. An agonist, antagonist or test compound may be a chemical compound, a mixture of chemical compounds, a biological macromolecule, or an extract made from biological materials such as bacteria, plants, fungi, or animal cells or tissues. Typically, test compounds may include structural analogs or peptidomimetics which are derived from the polypeptides described herein, and particularly the biologically active fragments. Test compounds are evaluated for potential activity as agonists or antagonists of functions which result in signal transduction, by inclusion in screening assays described herein. An "agonist" will enhance the particular observed activity, e.g. GRB2 association or 5-phosphate cleavage, while an "antagonist" will diminish the particular observed activity. The terms "agonist" and "antagonist", as used herein, do not imply a particular mechanism of function. Particularly targeted test compounds include polypeptide fragments of the polypeptides of the present invention and structural analogs or peptidomimetics of these peptides.

In a first aspect, the screening methods of the present invention typically involve the incubation of a polypeptide of the present invention, or a GRB2 associating fragment thereof, in the presence of GRB2 as well as a particular test compound. The mixture is then assayed to determine the levels of GRB2/polypeptide interaction by determining the amount of GRB2/polypeptide complex formed in the presence and absence of the test compound. Where the presence of the test compound results in an increase or decrease in the amount of complex formed, it will be indicative that the test compound is an agonist or antagonist of GRB2-mediated signal transduction, respectively.

For determination of the amount of GRB2/polypeptide complex formed, one may employ any number of a variety of well known assay methods. For example, immunoprecipitation of one polypeptide or protein that participates in the complex, followed by assaying the immunoprecipate for the other participant, will generally indicate the amount of complex formed. For example, following co-incubation of the polypeptide of the invention with GRB2, in the presence of the test compound, the polypeptide may be immunoprecipitated using an antibody that recognizes and specifically binds an epitope in the polypeptide's sequence. This epitope may be a sequence that is endogenous to the polypeptide or may be exogenously introduced as a labeling group, e.g., an antibody binding epitope tag or assayable enzyme. Following immunoprecipitation, the precipitate may be assayed for the presence of the other participant in the complex, e.g., GRB2, which may also be labelled, albeit in a distinguishing manner, e.g., a radiolabel, separately assayable enzyme, distinct antibody binding epitope tag or the like.

In an alternative method, one of the participants in complex formation, e.g., a polypeptide of the invention, may be coupled with an appropriate reporter group, while another participant, e.g., GRB2, is immobilized upon a solid support. Useful reporter groups, or labels have been previously described herein, including, e.g. radiolabels, such as, $^{125}I$, $^{32}P$ or $^{35}S$, fluorescent or chemiluminescent groups, substrates, cofactors, inhibitors, affinity ligands, antibody binding epitope tags, or enzymes which are capable of being assayed, e.g. horseradish peroxidase, luciferase, or other readily assayable enzymes. These enzyme groups may be attached to the polypeptide of the present invention by chemical means or expressed as a fusion protein, as already described.

Screening is then carried out by contacting the labeled participant with the immobilized participant in the presence and absence of the test compound. The amount of reporter group that binds to the solid support-bound participant is indicative of the amount of complex formed. The level of polypeptide bound in the presence of the test compounds may then be compared to the levels bound in control experiments, e.g., in the absence of the test compounds.

A variety of solid supports may be used in these screening methods. For example, blot formats may be employed where the protein or polypeptide is spotted on an appropriate substrate, e.g., nitrocellulose, PVDF and the like. Alternatively, resin or bead formats may also be used as the solid supports, including beads of agarose, cellulose, silica, polystyrene, divinylbenzene and the like.

Where the test compound results in an increase in the level of polypeptide which associates with GRB2, it is indicative that the test compound is an agonist of GRB2/GA5Ptase interaction, and more particularly, the GRB2-mediated signal transduction pathway. Similarly, where the presence of the test compound results in a decrease in the level of polypeptide GRB2 complex formed, it is indicative that the test compound is an antagonist of that interaction and signal transduction pathway.

In another aspect, the polypeptides of the present invention can be used as a model system for screening test compounds to identify agonists or antagonists of inositol polyphosphate 5-phosphatase activity generally, and in particular the inositol polyphosphate 5-phosphatase activity of GA5Ptase. Because the processing of phosphatidylinositols and particularly, the cleavage of the 5-phosphate from PtdIns(3,4,5)$P_3$ has been linked to the activation of Ras, it will be desirable to provide a model system for screening compounds which block or otherwise inhibit this conversion, and thereby block Ras activation.

The methods for determining whether a test compound is an agonist or antagonist of the inositol polyphosphate 5-phosphatase activity of the polypeptides of the invention, are generally similar to the above described methods. In particular, these methods comprise incubating a polypeptide having the desired inositol polyphosphate 5-phosphatase activity, e.g., GA5Ptase or catalytically active fragments thereof, with its substrate in the presence and absence of the test compound. This incubation may be carried out in vitro or in vivo, e.g., using a transgenic animal model which has been engineered to express the polypeptides of the invention. For the polypeptides of the present invention, the appropriate substrate may generally be selected from, e.g. D-myo-Inositol 1,3,4,5-tetrakisphosphate ("Ins(1,3,4,5)$P_4$") and Phosphatidylinositol 3,4,5-trisphosphate ("PtdIns(3,4,5) $P_3$"). Following a prescribed reaction time the reaction mixture is assayed for the production of the products of inositol polyphosphate 5-phosphatase activity on these substrates. Assaying for production of the various reaction products, e.g. Ins(1,3,4)$P_3$ from Ins(1,3,4,5)$P_4$, or PtdIns(3,4)$P_2$ from PtdIns(3,4,5)$P_3$, may be carried out by a variety of methods known in the art. For example, HPLC analysis can be readily used to quantitatively identify the above described reaction products, using, e.g. tritiated substrates, and the like (see Example 2, below). Similarly, on a more qualitative level, thin layer chromatography (TLC) can also be used to identify reaction products. The levels of the above described reaction products produced in the presence and absence of the test compound are then compared. Where the presence of the test compound results in an increase or decrease in the level of the reaction product produced by the polypeptide, it is indicative that the test compound is an agonist or antagonist of inositol polyphosphate 5-phosphatase activity, respectively, and more particularly, the inositol polyphosphate 5-phosphatase activity described herein.

In a related embodiment, the present invention also provides kits for carrying out the above described screening methods. The kits of the present invention generally include a polypeptide of the present invention, e.g. the GA5Ptase polypeptide or a biologically active fragment thereof, as well as a ligand of the polypeptide where the binding activity is to be screened, e.g., GRB2, or a substrate of that polypeptide where the inositol polyphosphate 5-phosphatase activity is to be screened, e.g., Ins(1,3,4,5)$P_4$, or PtdIns(3,4,5)$P_3$. One or more of these components may generally be provided in premeasured aliquots. The aliquots can be contained in any suitable container such as a vial or a tube. The polypeptide component can be provided in solution or in lyophilized form, and may be immobilized. The polypeptide preparation may also contain preservatives such as sodium azide or protease inhibitors such as EDTA. A carrier protein such as BSA or ovalbumin, usually between 0.5–5%, may also be included to stabilize the polypeptide. The solution form of GA5Ptase may contain up to 50% glycerol if the enzyme is to be stored frozen, e.g., at −20° C. to −70° C. If the GA5Ptase is provided in lyophilized form, the kit can include a reconstitution buffer to reconstitute the polypeptide, as well as a reaction buffer. Alternatively, the polypeptide can be added to the reaction buffer and the solution freeze dried. This form can be readily reconstituted in distilled water with the necessary salt components already present for the particular reaction to be screened, so that no additional reaction buffer need be supplied. Thus, depending on the form and composition of the polypeptide preparation, different buffers may be included in the kit and they may be provided in more than one aliquot. Although described in substantial detail herein, these buffers are generally optional. The appropriate substrate or ligand, depending upon the particular screening method used, may be provided in a similar fashion to that of the polypeptide component. The kits will also typically include additional reagents for carrying out the particular method, e.g. stains for detection, antibodies, solid supports, and the like, as well as detailed operating specifications for their use. For example, where binding interactions are being screened, the ligand component may generally be supplied within the kit, already coupled to an appropriate support.

Once identified, particular agonists or antagonists may then be used to enhance or block the activity of the polypeptides of the present invention. This may be particularly useful in therapeutic applications (see discussion, below).

B. Therapeutic Applications

In addition to the above described uses, the polypeptides and nucleic acids of the present invention may also be used in therapeutic applications for the treatment of human or non-human mammalian patients. The term "treatment" refers to the full spectrum of treatment for a given disorder from which the patient is suffering, including alleviation of some, most or all symptoms resulting from that disorder, to an outright cure for the particular disorder to prevention of the onset of the disorder.

As described previously herein, the polypeptides of the present invention have been implicated as providing a critical step in the growth factor activation cascade, and particularly the activation of Ras. Activation of Ras has been associated with a variety of proliferative disorders including atherosclerosis, inflammatory joint diseases, psoriasis, restenosis following angioplasty, and cancer.

Accordingly, treatment of the above described disorders can generally be carried out by blocking or inhibiting activation of Ras. This may generally be accomplished by blocking or inhibiting one or more of the activities of the GA5Ptase polypeptide which are involved in the signal transduction pathway which activates Ras, e.g., the polypeptide's ability to bind GRB2, or the polypeptide's ability to bind to or catalyze the dephosphorylation of its substrate.

Generally, inhibition of the particular activity may be carried out by providing a polypeptide of the invention which will compete with the endogenous GA5Ptase protein. For example, by administering to a patient an effective amount of a GRB2 associating fragment of the polypeptides, as described herein, one can out compete the endogenous GRB2 associating activity of the endogenous GA5Ptase protein, and thereby reduce the level of Ras activation. Similarly, by administering to the patient an effective amount of a substrate binding, although non-catalytic, fragment of the GA5Ptase peptide, as described herein, one can effectively out compete the naturally occurring GA5Ptase protein, and thus block cleavage of the substrate, and the ensuing activation cascade reactions.

The quantities of reagents necessary for effective therapy, also referred to herein as an "effective amount," or "therapeutically effective amount," will depend upon many different factors, including means of administration, target site, physiological state of the patient and other medicants administered. Thus, treatment doses will need to be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Generally, therapeutically effective amounts of the GA5Ptase containing polypeptides of the present invention will be from about 0.0001 to about 10 mg/kg, and more usually, from about 0.001 to about 0.1 mg/kg of the host's body weight. Various considerations are described, e.g., in Gilman et al., (Eds.), *Goodman and Gilman's: The Pharmacological Basis of Therapeutics*, (8th ed. 1990), Pergamon Press, and *Remington's Pharmaceutical Sciences* (7th ed. 1985) Mack Publishing Co., Easton, Penn. Methods of administration, also discussed in the above references, include, e.g., oral, intravenous, intraperitoneal or intramuscular administration, and local administration, including topical, transdermal diffusion and aerosol administration, for therapeutic, and/or prophylactic treatment. The active agent, i.e., the polypeptide component, will generally be administered in a composition additionally comprising a pharmaceutically acceptable carrier. Suitable pharmaceutically acceptable carriers include water, saline, buffers and other compounds described in, e.g., the Merck Index, Merck and Co., Rahway, N.J.

Constituents of pharmaceutical compositions, in addition to the active agents, include those generally known in the art for the various administration methods used. For example, oral forms generally include powders, tablets, pills, capsules, lozenges and liquids. Similarly, intravenous, intraperitoneal or intramuscular formulations will generally be dissolved or suspended in a pharmaceutically acceptable carrier, e.g., water, buffered water, saline and the like. Additionally, these compositions may include additional constituents which may be required to approximate physiological conditions, such as pH adjusting and buffering agents, tonicity adjusting agents, wetting agents and the like. For solid compositions, conventional nontoxic solid carriers may be used which include, e.g., pharmaceutical grades of mannitol, lactose, starch, magnesium stearate, sodium saccharin, talcum, cellulose, glucose, sucrose, magnesium carbonate and the like.

Administration may also be carried out by way of a controlled release composition or device, whereby a slow release of the active ingredient allows continuous administration over a longer period of time.

Additionally, inositol polyphosphates play important roles in cell signaling pathways, the present invention can provide an exogenous regulatory mechanism in the treatment of disorders where these regulatory mechanisms are disfunctional. In particular, the treatment of a particular disorder may comprise gene therapy techniques involving the mutation, dysregulation or augmentation of levels of GA5ptase. For example, gene therapy techniques may involve the introduction into afflicted cells, of genes which encode a protein or polypeptide which possesses the activity of GA5ptase. This exogenously introduced protein may then augment existing levels of this activity in cells that may be otherwise deficient.

Strategies for gene therapy are reviewed in Friedmann, *Science* 244:1275 (9189). Genetic constructs encoding the PTB domain or functional derivative of that domain, can be used in these gene therapy techniques. Delivery of the genetic construct of interest, i.e., the nucleic acid encoding a GA5ptase protein or fragment, may be accomplished in vivo by administering the therapy vector to an individual patient, typically by systemic administration (e.g., intravenous, intraperitoneal, intramuscular, subdermal, or intracranial administration). Alternatively, the vector may be used to deliver nucleic acids to cells ex vivo, such as cells explanted from an individual patient or universal donor hematopoietic stem cells, neurons, etc, e.g., by transfection of the cells with nucleic acids of interest cloned into retroviruses. Following transfection, the cells are reimplanted into the patient, usually after selection for cells which have incorporated the nucleic acid. The infusion into the patient of transfected cells can replace cells which are dysfunctional for the particular regulatory scheme which results in the disorder being treated.

C. Affinity Probes

Because the polypeptides of the present invention associate with GRB2 proteins, and specifically, via the SH3 domains, these proteins or their biologically active fragments may be particularly useful as affinity probes or ligands. In particular, the proteins can be used to identify or capture GRB2 proteins from a mixture of different proteins.

Typically, use of the polypeptides of the present invention in identifying GRB2 proteins in a mixture of proteins may be carried out using a Western blotting format. In particular, the mixture of proteins may be immobilized on a solid support, as described above. Immobilization may include simple spotting, electroblotting of SDS-PAGE gels and the like. The blot is then blocked using a nonspecific protein, i.e., BSA. Labeled polypeptides of the present invention may then be used to interrogate the blot, binding to the immobilized GRB2.

The polypeptides of the present invention may also be used as affinity ligands to purify Grb2 proteins from a mixture of proteins. In particular, the polypeptide of the invention is coupled to a solid support. The support bound polypeptide is then contacted with the mixture of proteins containing the GRB2 protein under conditions that are conducive to GA5Ptase/GRB2 binding. The support is then washed to remove unbound and nonspecifically bound proteins. Substantially pure GRB2 may then be readily eluted from the support by, e.g. a change in salt, pH or buffer concentrations.

The present invention is further illustrated by the following examples. These examples are merely to illustrate aspects of the present invention and are not intended as limitations of this invention.

VIII. EXAMPLES

Example-1

Cloning and Sequence Analysis of GA5Ptase

A bacterially expressed GST-GRB2 fusion protein containing a 5 amino acid RRASV heart muscle kinase site was purified and radioactively labeled with [$^{32}$P]ATP. The purified protein was used to screen a human placental λgt11 oligo dT primed cDNA library (Clonetech) using the guanidine-HCl denaturation/renaturation screening technique initially described by Blanar and Rutter, Science 256:1014–1018 (1992). A schematic of this protein is shown in FIG. 1. Because all GRB2 interacting clones obtained in the first round of screening encoded catalytic regions of protein tyrosine kinases, duplicate filters were probed with antiphosphotyrosine antibody to screen against SH2 domain interactions. One clone was identified that specifically interacted with GRB2 and was not tyrosine phosphorylated. Sequencing of this clone indicated that it was a partial cDNA clone with no similarity to any other protein or cDNA. Multiple PXXP motifs were present, indicating the likely contact region with the SH3 domains of GRB2. Northern blot analysis indicated a 4.3 kb long transcript with broad tissue distribution, the highest being in placenta. Purified GST-GA5Ptase fragment was produced by cloning the original λgt11 cDNA fragment (nucleotides 2687–4146) into pGex1. Smith, et al., Gene 67:31–40 (1988).

Figure 2:
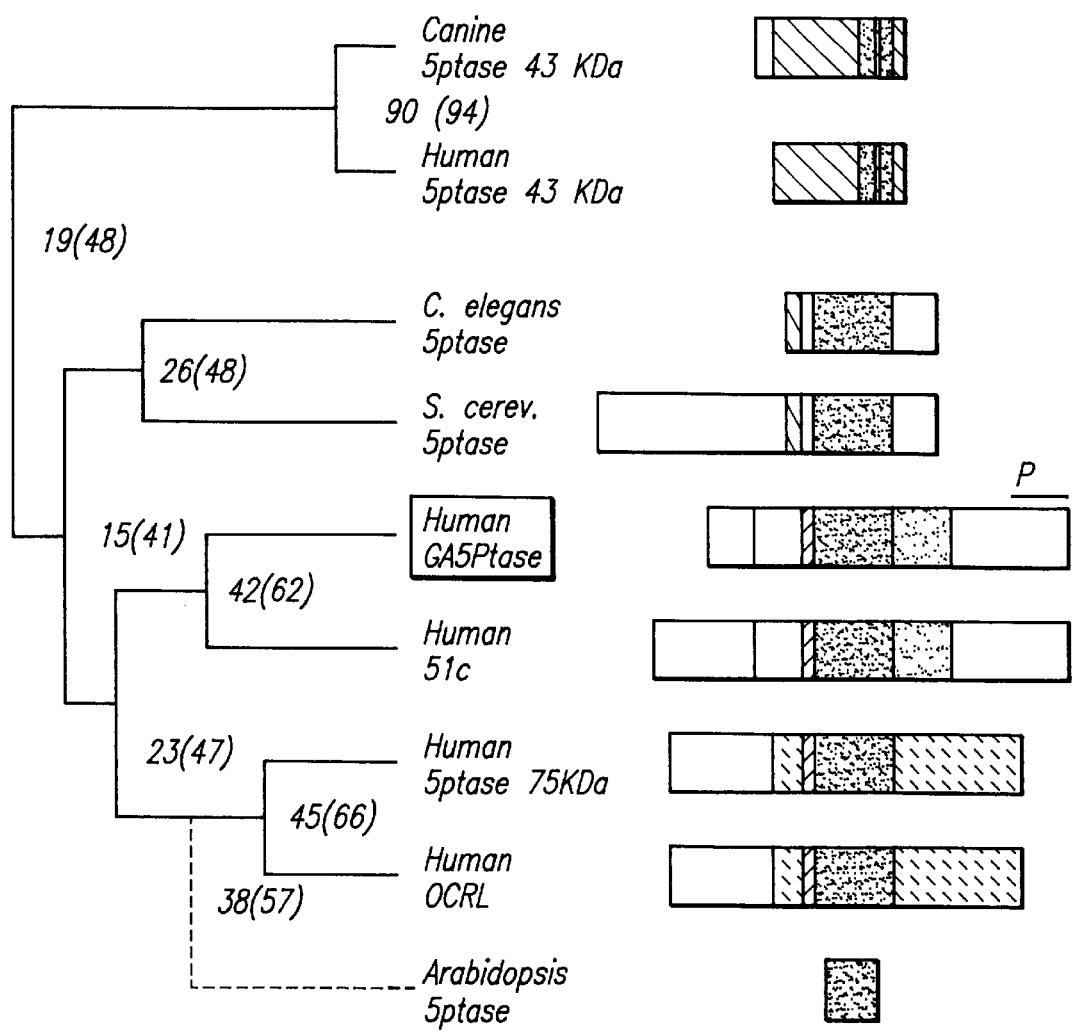
FIG. 2 shows a ribbon diagram and dendrogram illustrating relative similarities between inositol polyphosphate 5-phosphatases. Numbers beside the nodes of the dendrogram indicate the percent identity and (similarity). The black bar above the ribbon representation of GA5Ptase indicates the region cloned by interaction with GRB2, whereas the "P" indicates the location of PXXP motifs.
Figure 11:
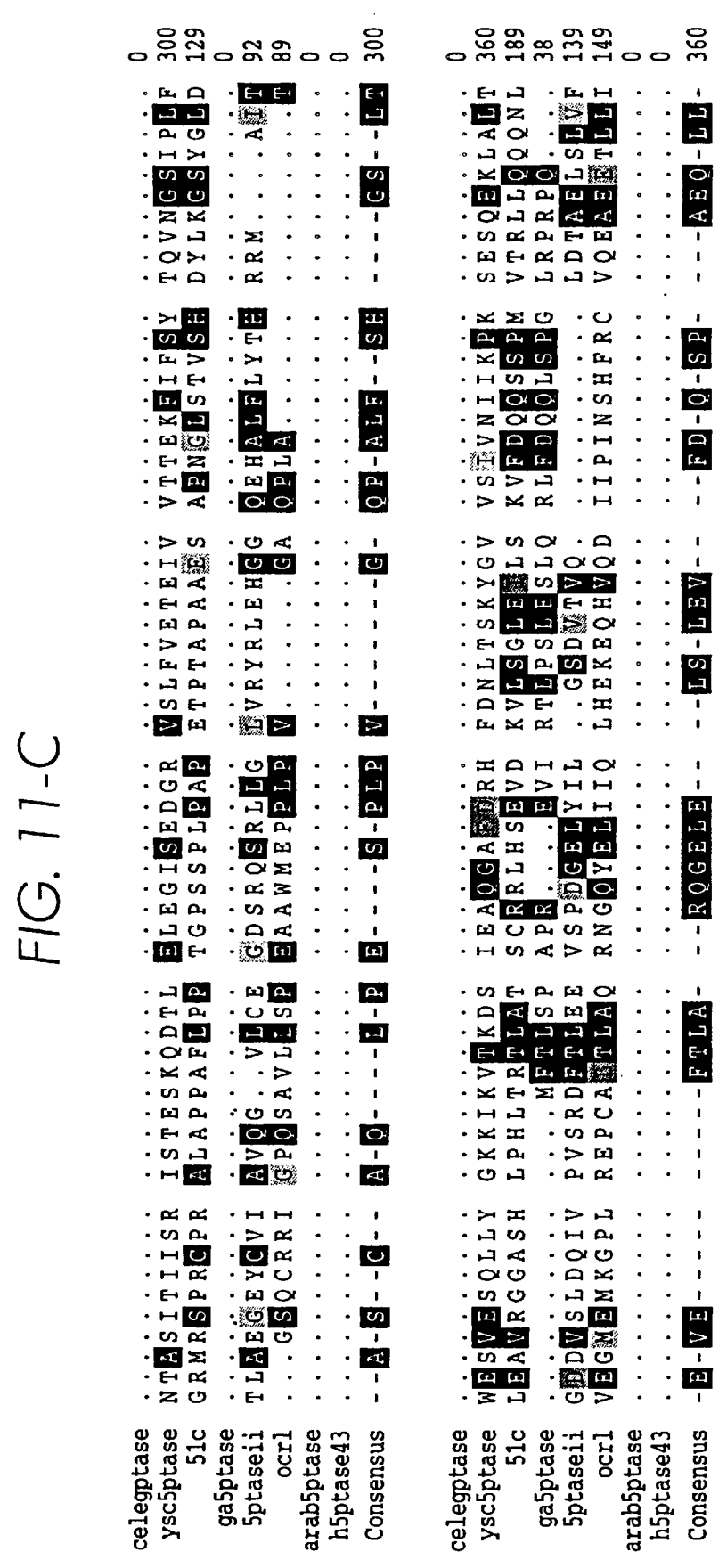
Figure 11:
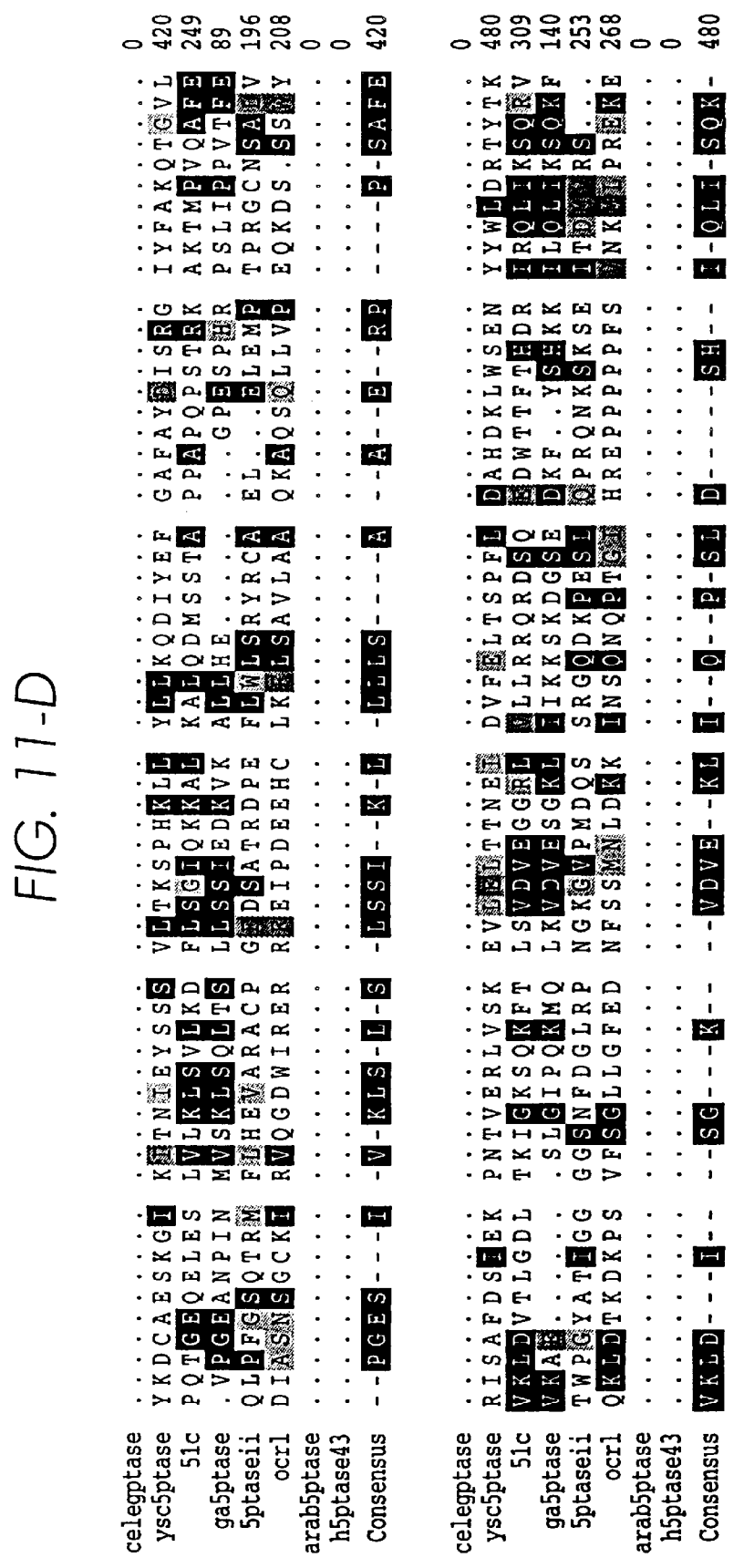
Figure 11:
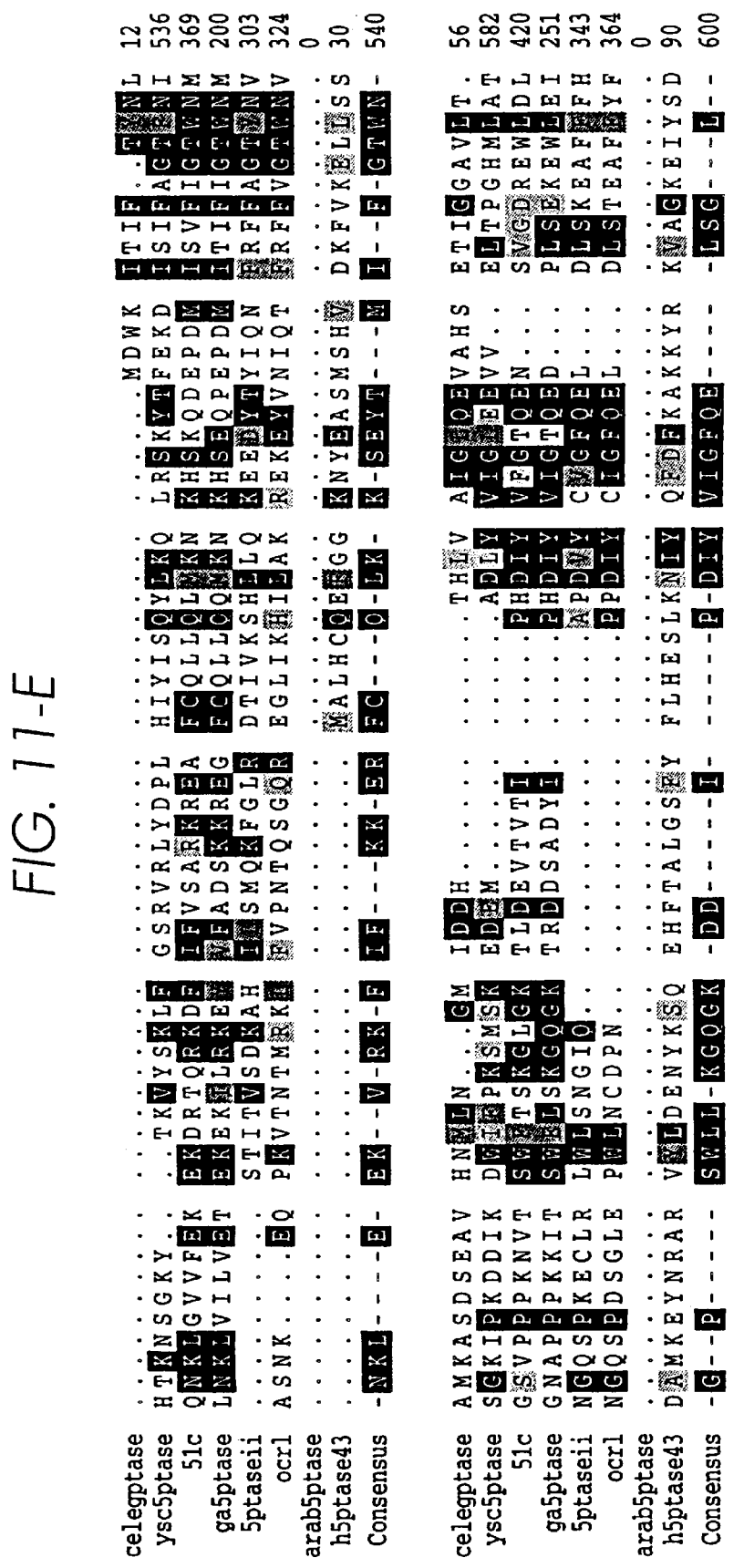
Figure 11:
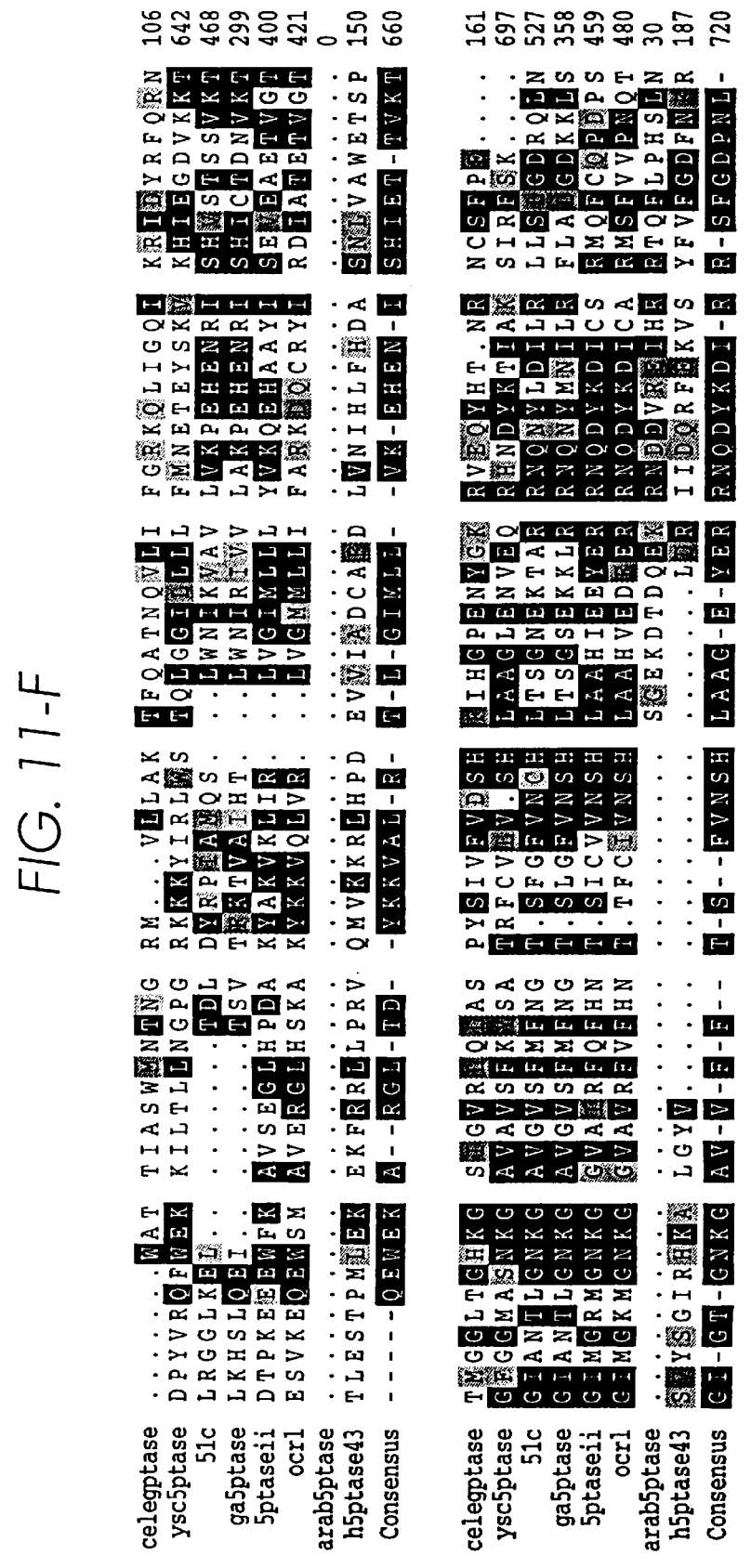
Figure 11:
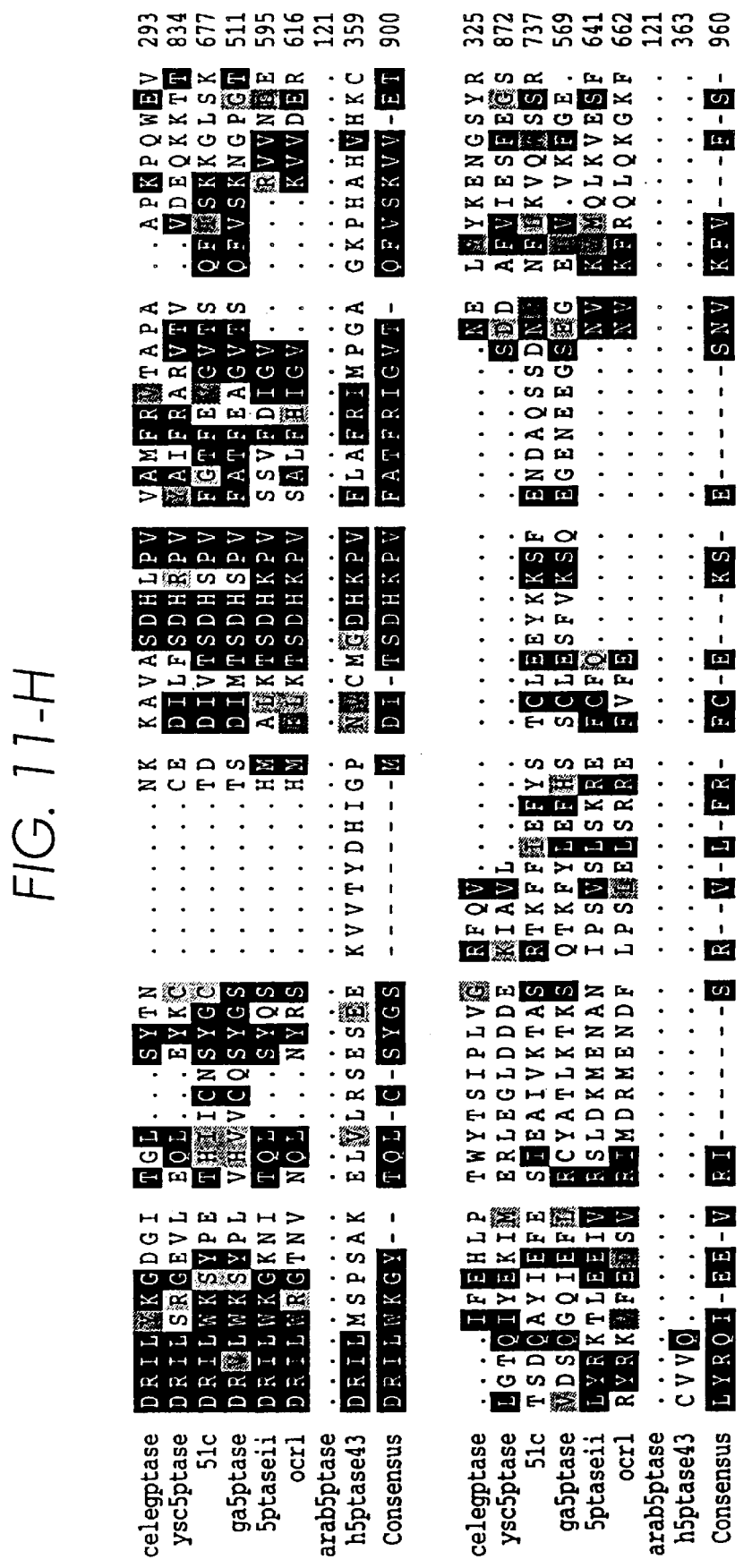
Figure 11:
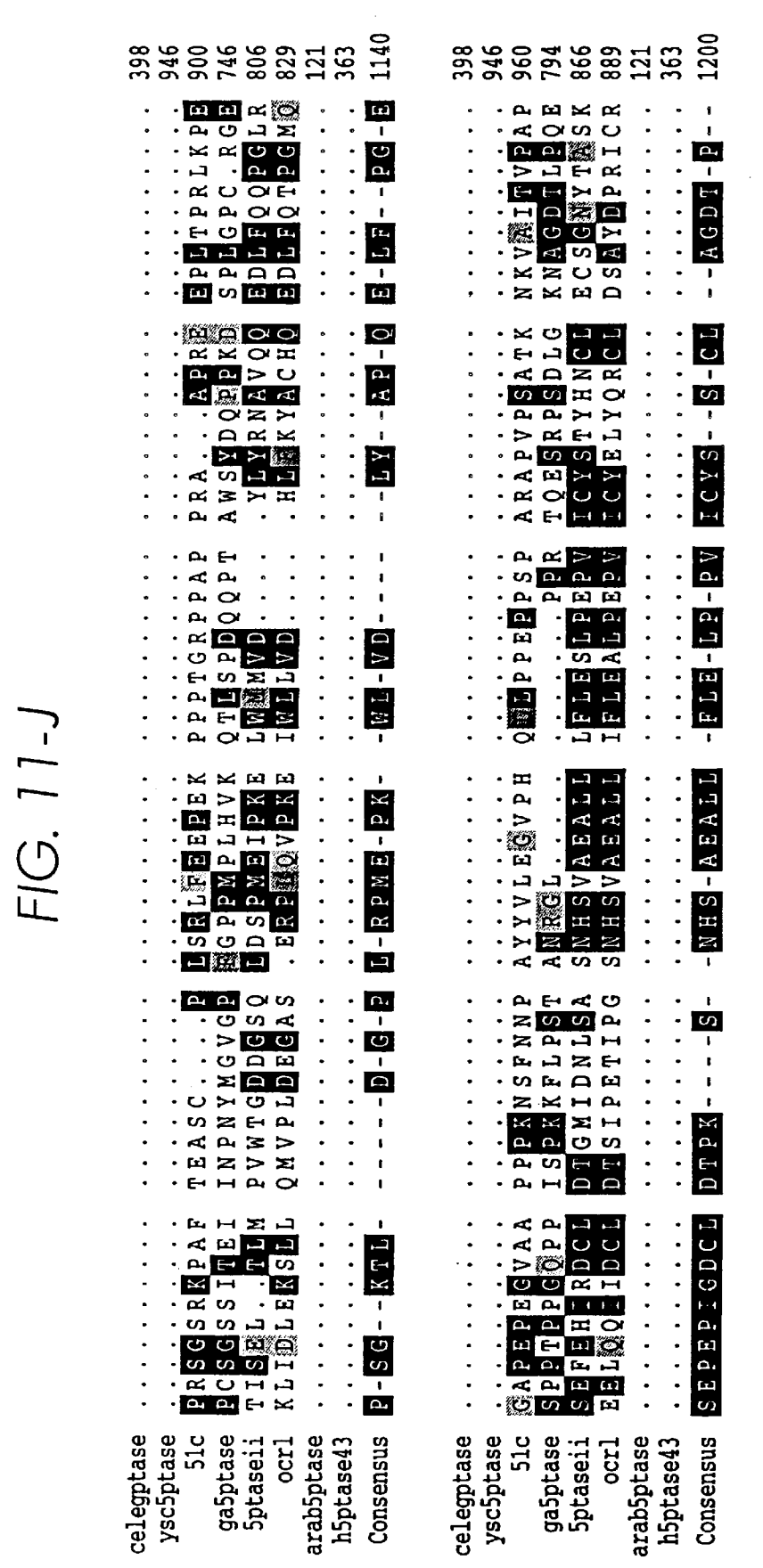
Figure 11:
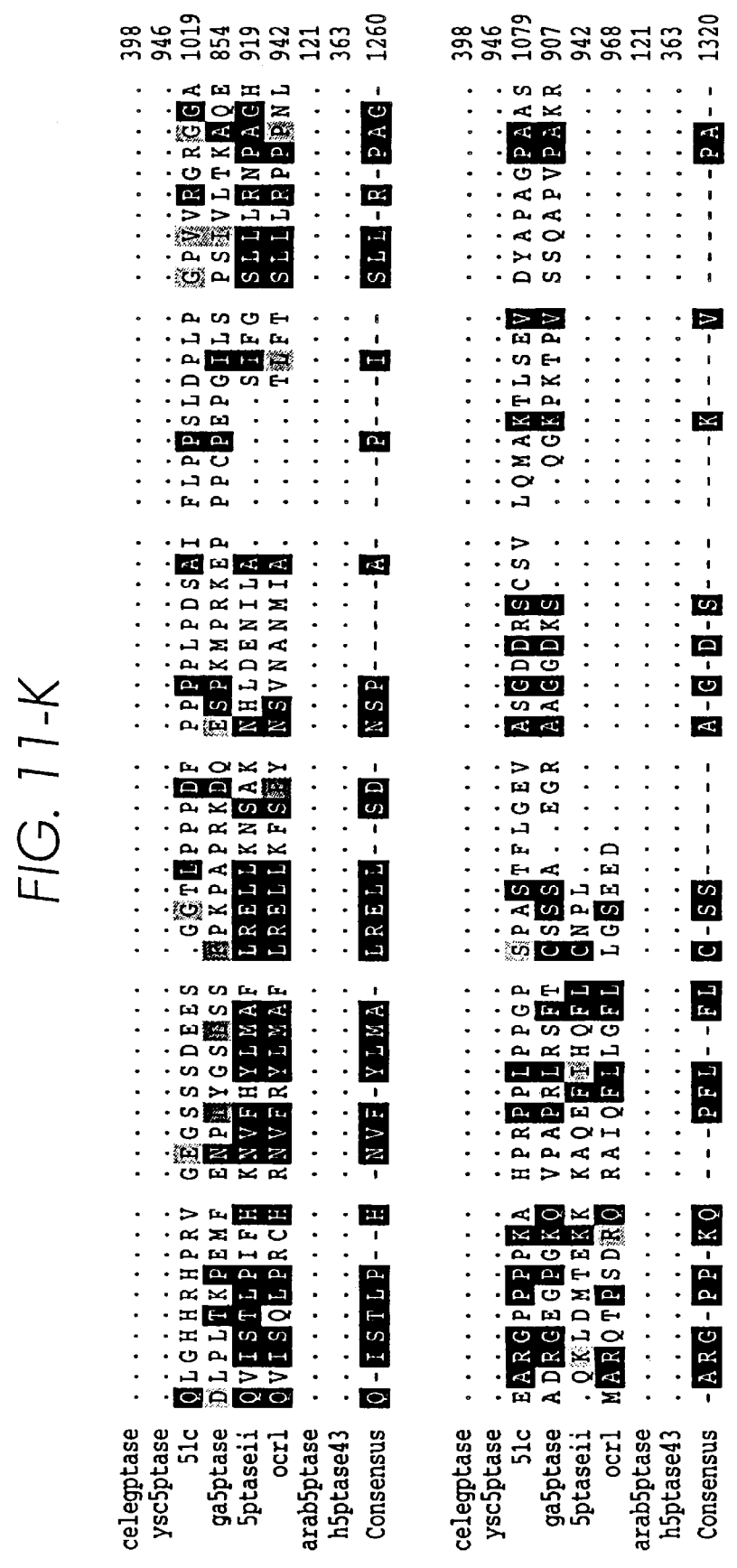

Binding specificity of this protein fragment for GRB2 was evaluated by Far-Western blots of the protein with roughly equal amounts of radioactively labeled GRB2, Vav SH3-SH2-SH3 domains (amino acids 648–844, Katzav, et al., Embo J. 8:2283–2290 (1989)), Nck SH3—SH3—SH3 domains (amino acids 1-249, Hu, et al., Mol. Cell. Biol. 15:1169–1174 (1995)) and p85 SH3 domain (amino acids 1–81, Klippel, et al., Mol. Cell. Biol. 12:1451–1459 (1992)). Only GRB2 bound specifically to the GST fused fragment of the newly cloned protein and no proteins bound GST itself. A full length cDNA clone was obtained by screening a λgt10 human placental cDNA library. This 4146 bp clone contained an open reading frame encoding a 976 amino acid protein. The predicted 110 kDa protein showed that it has significant homology to a family of proteins known as inositol polyphosphate 5-phosphatases. FIG. 2 shows a ribbon diagram and dendrogram indicating relative homology of GA5Ptase to a number of inositol polyphosphate 5-phosphatases. FIG. 11 also shows a direct sequence comparison of GA5Ptase to these other phosphatase sequences. Included in the comparison are the C. elegans inositol polyphosphate 5-phosphatase ("celegptase") (SEQ ID NO:3), S. cereviseae inositol polyphosphate 5-phosphatase ("ysc5ptase") (SEQ ID NO:4), GA5Ptase (SEQ ID NO:2), human 5lc ("5lc") (SEQ ID NO:5), the 75 kDa human platelet inositol polyphosphate 5-phosphatase type-II ("5ptaseii") (SEQ ID NO:6), the human ocr1 protein responsible for human oculocerebrorenal syndrome ("ocr1") (SEQ ID NO:7), Arabidopsis inositol polyphosphate 5-phosphatase ("arab5ptase") (SEQ ID NO:8) and canine inositol polyphosphate 5-phosphatase 43 kDa ("h5ptase43") (SEQ ID NO:9). The identified consensus sequence is also provided ("consensus") (SEQ ID NO:10).

Example-2

Characterization of Enzymatic Activity of GA5Ptase

Figure 6:
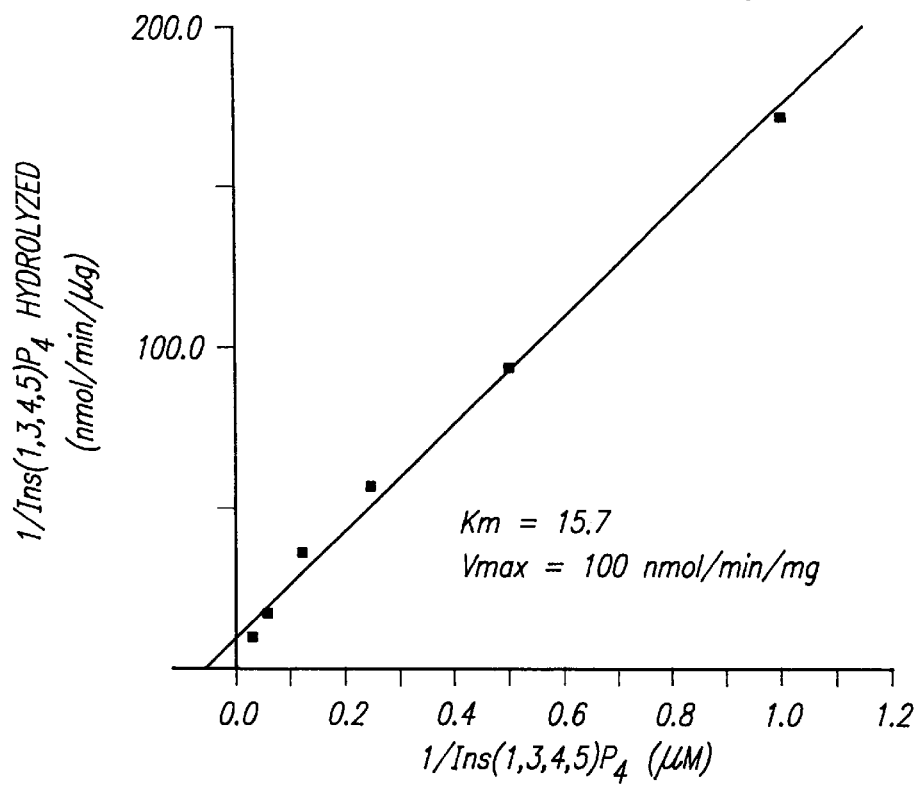
FIG. 6 shows the effect of varying concentration of Ins(1,3,4,5)P$_4$ on the rate of its hydrolysis by GA5Ptase.
Figure 7A:
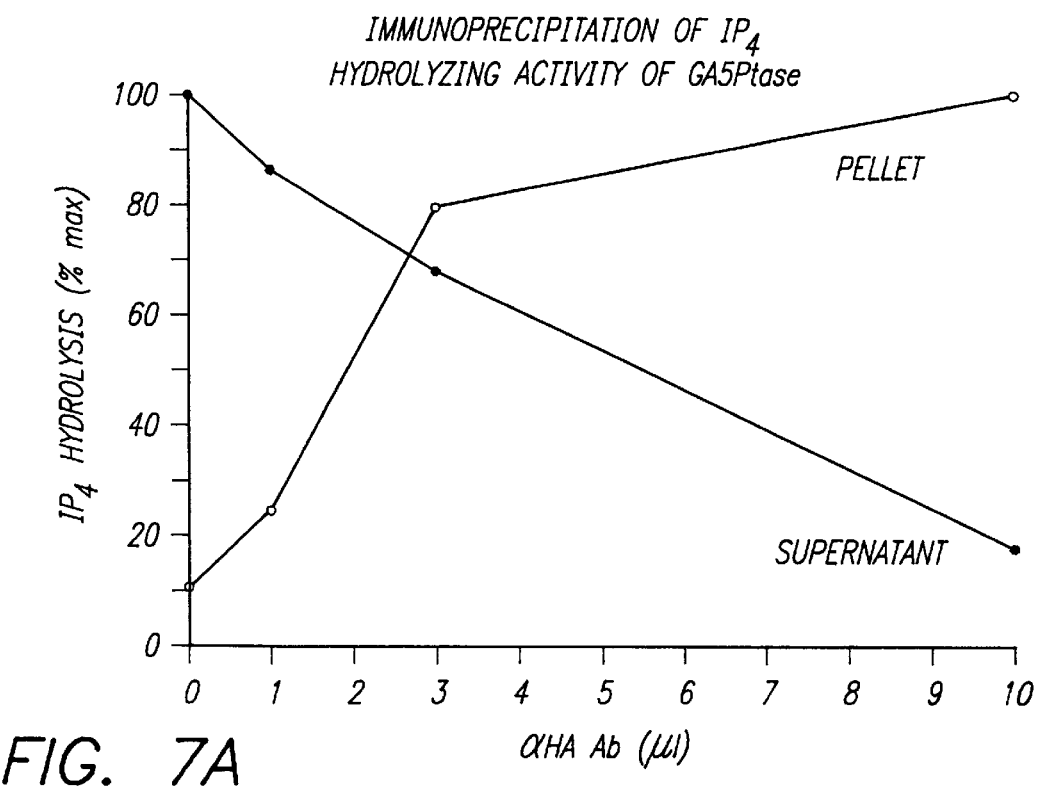
FIGS. 7A and 7B show the immunoprecipitation of both GA5Ptase protein and Ins(1,3,4,5)P$_4$ hydrolyzing activity of GA5Ptase. HA-tagged GA5Ptase was immunoprecipitated with αHA antiserum. Following contact with protein A sepharose, the supernatant (●) and protein A sepharose pellet (○) were Western blotted against αHA antiserum (FIG. 7B) and assayed for ability to hydrolyze Ins(1,3,4,5)P$_4$ (FIG. 7A).
Figure 7B:
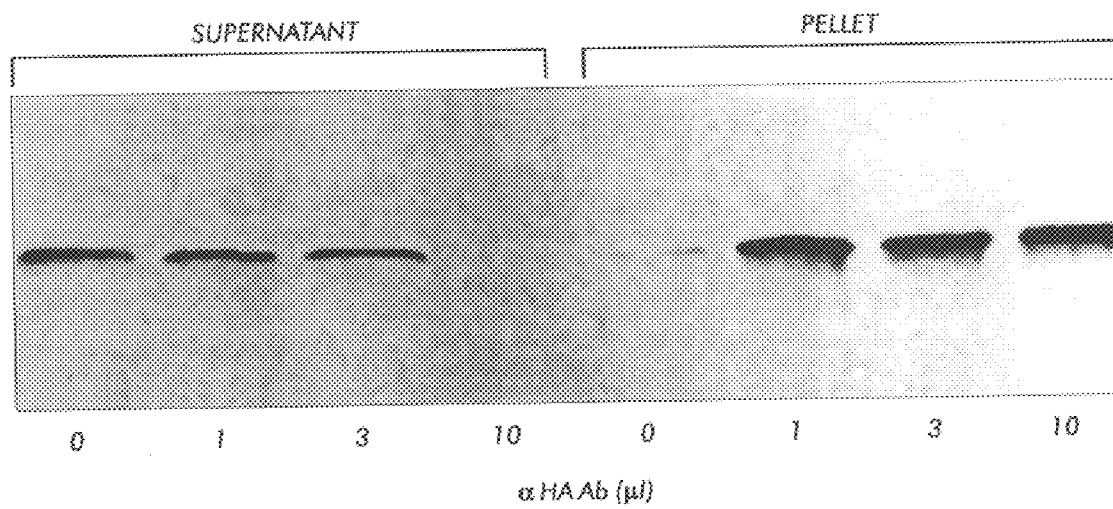

The next step was to characterize the nature of the activity of the GA5ptase protein. FIG. 6 illustrates the effect of varying concentration of Ins(1,3,4,5)P$_4$ on the rate of its hydrolysis by GA5Ptase. FIG. 7 illustrates the coprecipitation of GA5ptase and IP$_4$ hydrolyzing activity.

Figure 8A:
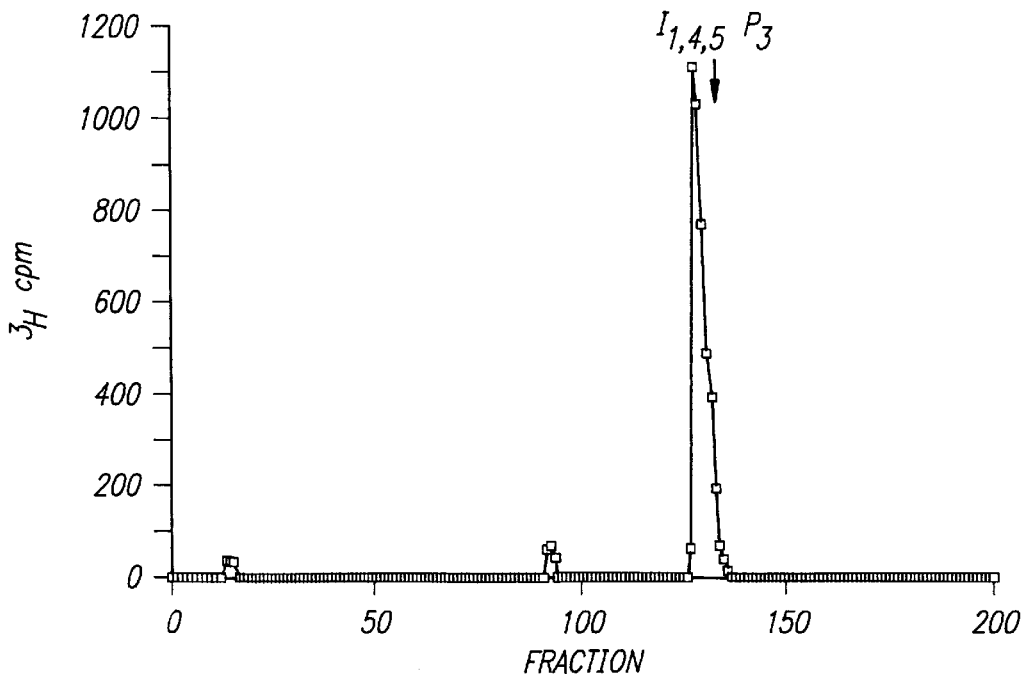
FIGS. 8A–C show HPLC analysis of reaction products from incubation of GA5Ptase with Ins(1,3,4,5)P$_4$.

To ensure that GA5Ptase was in fact an inositol polyphosphate 5-phosphatase, $^3$H-Ins(1,3,4,5)P$_4$ (200 pmoles) was incubated with GA5Ptase (1 μg) for 1 hour at 37° C. An aliquot of the reaction mix was quenched with 500 μl cold water, mixed with 300 cpm $^{32}$P-Ins(1,4,5)P$_3$ as an internal standard, and analyzed by Absorbosphere™ Sax HPLC using a NaPO$_4$ gradient. FIG. 8A shows the resulting chromatogram showing conversion of the Ins(1,3,4,5)P$_4$ to Ins(1,3,4)P$_3$ by GA5Ptase.

Figure 8B:
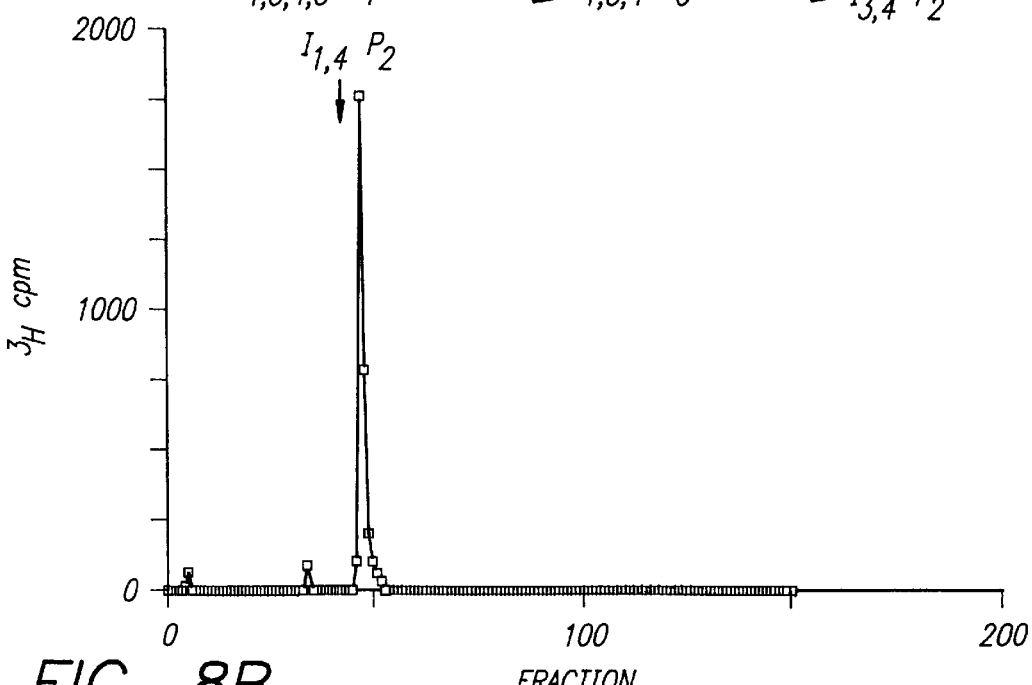

An aliquot of the reaction mix was then incubated with a purified recombinant inositol polyphosphate 1-phosphatase (York, et al., Proc. Nat'l Acad. Sci. USA 87:9548–9552 (1990)), quenched with 500 μl cold water, mixed with 300 cpm $^{32}$P-Ins(1,4)P$_2$ as an internal standard, and analyzed using Partisil™ 10 Sax HPLC using an NH$_4$COOH gradient. FIG. 8B shows that the product of GA5Ptase was converted by the inositol polyphosphate 1 phosphatase to Ins(3,4)P$_2$.

Figure 8C:
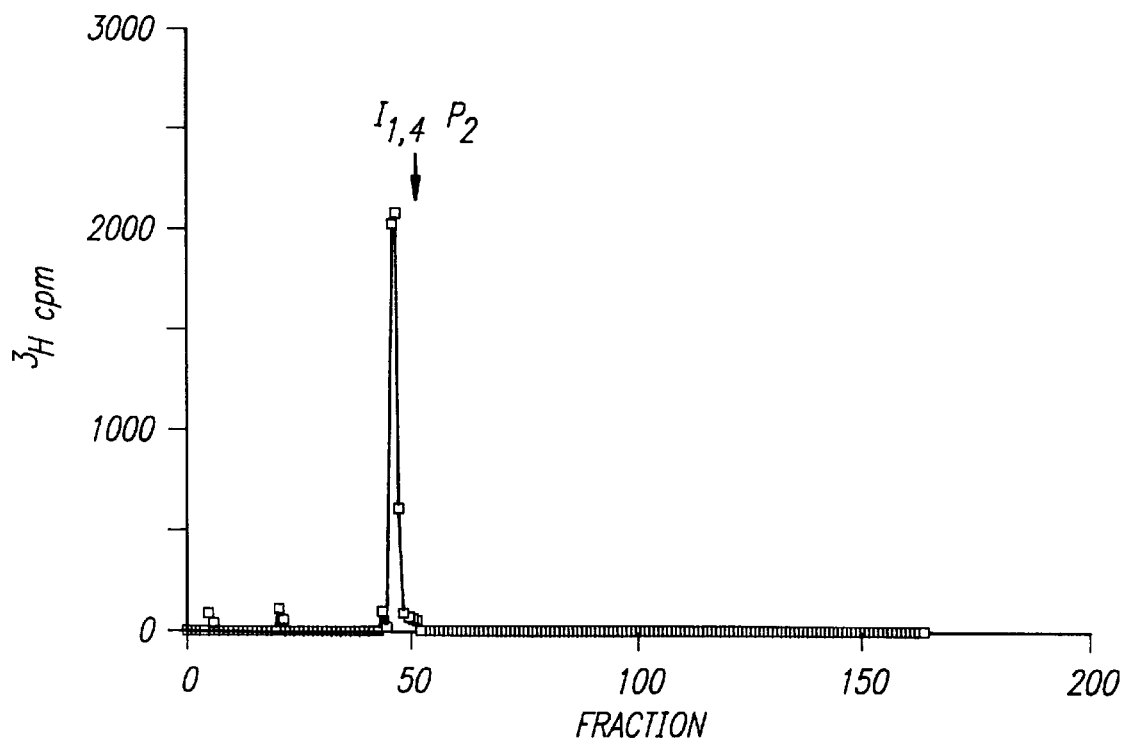

A further aliquot of the original reaction mix was incubated with a purified recombinant inositol polyphosphate 4-phosphatase, quenched with 500 μl cold water, mixed with $^{32}$P-Ins(3,4)P$_2$ as an internal standard and again analyzed using Partisil 10 Sax HPLC using an NH$_4$COOH gradient. FIG. 8C shows that the product of GA5Ptase action on Ins(1,3,4,5)P$_4$ was converted by inositol polyphosphate 4-phosphatase to Ins(1,3)P$_2$. These assays confirm that GA5Ptase has inositol polyphosphate 5-phosphatase activity.

Figure 9:
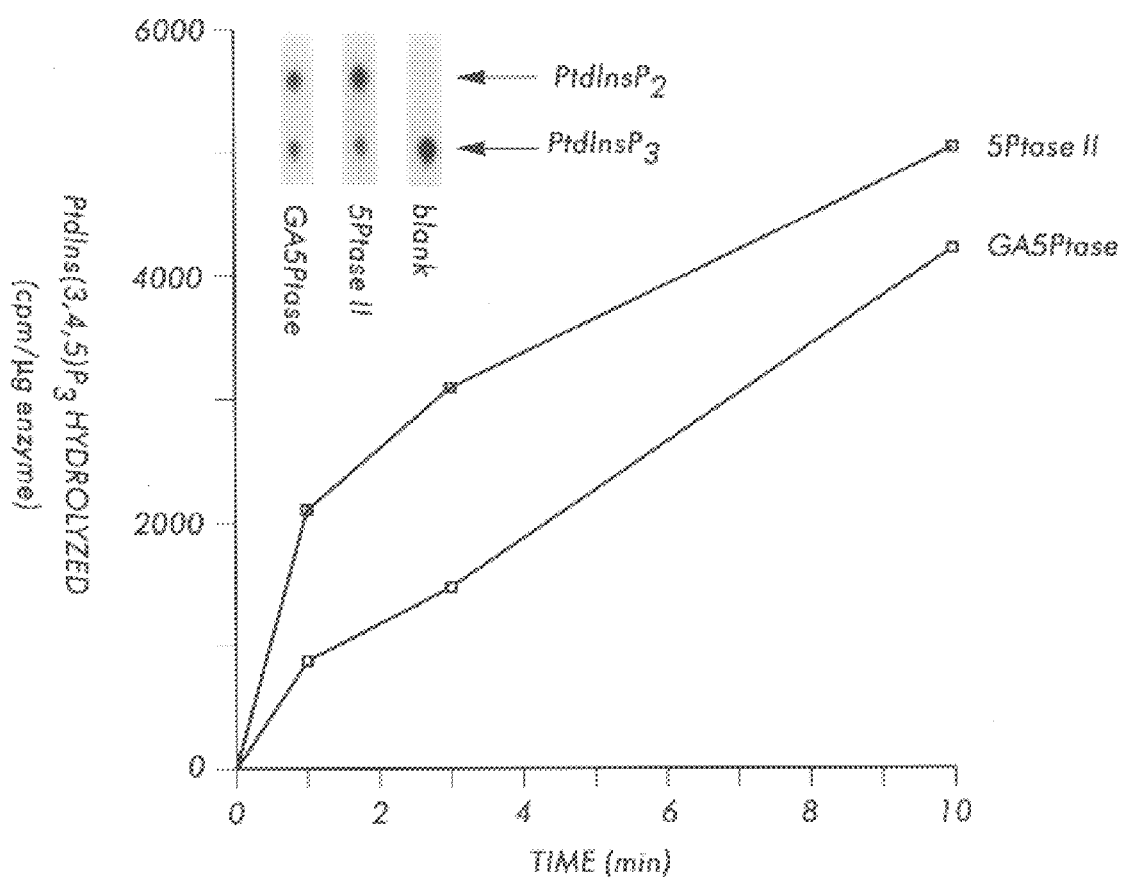
FIG. 9 shows the hydrolysis of PtdIns(3,4,5)P$_3$ by recombinant inositol polyphosphate 5-phosphatases. Specifically shown is a graph showing hydrolysis with GA5Ptase (open squares) and human inositol polyphosphate 5-phosphatase II ("5-Ptase II") (closed squares). Also shown is a TLC autoradiogram indicating conversion of PtdIns(3,4,5)P$_3$ to PtdInsP$_2$ by GA5Ptase and 5-Ptase II (inset).

GA5Ptase (20 ng) and 5ptase II (31 ng) were separately incubated with 1400 cpm $^{32}$P-PtdIns(3,4,5)P$_3$ in phosphatidylserine vesicles for 1, 3 or 10 minutes at 37° C. The reaction was stopped by addition of 3μl chloroform/methanol (1:1). The chloroform layer was spotted on an oxalate-dipped silica gel TLC plate and developed using a solvent mixture of chloroform/acetone/methanol/acetic acid/water from the TLC plate and quantified by Cerenkov radiation. Production of PtdInsP$_2$ from PtdIns(3,4,5)P$_3$ is shown in FIG. 9, plotted as a function of time. Each point shown is the average of quadruplicate assays. The inset shows an autoradiogram of a TLC plate indicating conversion of PtdIns(3,4,5)P$_3$ to PtdInsP$_2$ by both GA5Ptase and 5ptase II. Example-3

Co-immunoprecipitation of GA5Ptase

Figure 4:
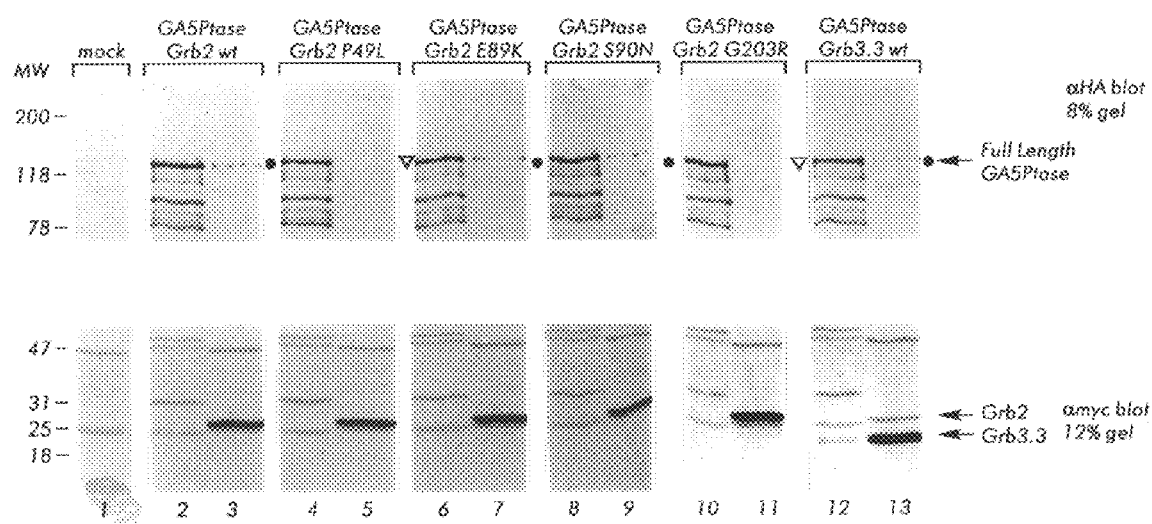
FIG. 4 shows results of co-immunoprecipitation of GA5Ptase with wild type GRB2 ("GRB2 wt"), point mutations of GRB2 ("GRB2 P49L", "GRB2 E89K", "GRB2 S90N", "GRB2 G203R") and GRB3.3.

Lysates from Balb 3T3 cells were immunoprecipitated with GRB2 antibody (Transduction Laboratories) and blotted with preimmune (P) and immune (I) GA5Ptase polyclonal antibodies. Co-immunoprecipitation of endogenous GA5Ptase with endogenous GRB2 was detected in unstimulated Balb 3T3 cells using antibodies raised against two different regions of GA5Ptase (amino acids 47–231 and 891–983). To define the interaction of GA5Ptase with GRB2, both molecules were co-expressed in Cos cells and co-immunoprecipitated (FIG. 4).

Figure 3:
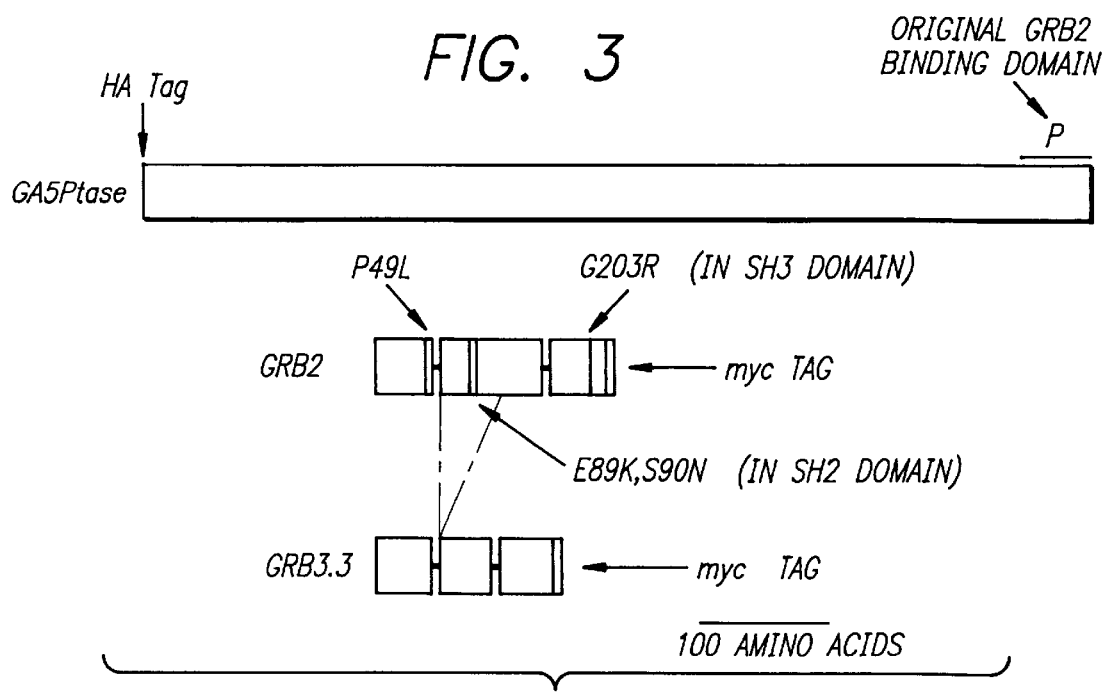
FIG. 3 shows a schematic representation of GA5Ptase, GRB2 and GRB3.3 molecules used in Cos7 Immunoprecipitations.
Figure 5A:
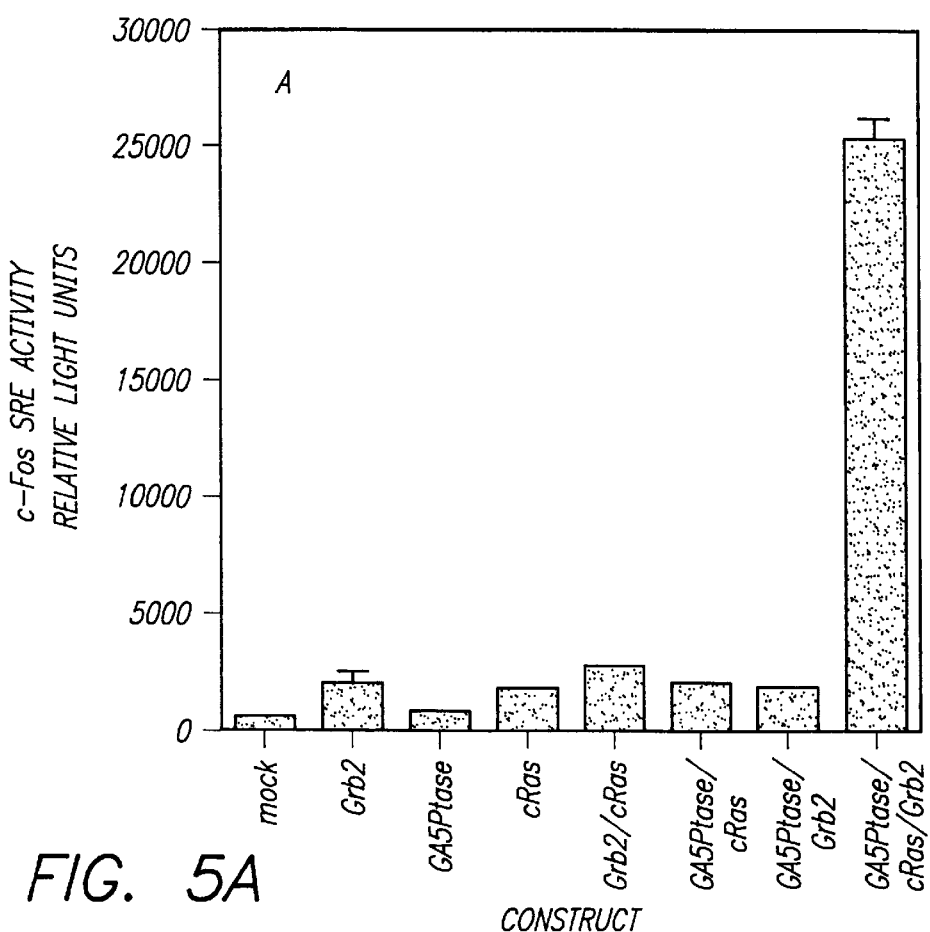
FIG. 5A shows c-Fos Serum Responsive Element (SRE) activation when co-expressed with various combinations of GRB2, c-Ras and GA5Ptase. The error bars indicate standard error of the mean of triplicate transfections.

Cos7 cells were transiently transfected with GA5Ptase and either wild type or single point mutations of GRB2 or GRB3.3. Schematic illustrations of the sequence structure of each of these proteins is shown in FIG. 3. Point mutations were the human counterparts of natural C. elegans Sem-5 point mutations. After 2 days of growth, cell lysates were immunoprecipitated with either myc antibody 9E10 (FIG. 4, odd numbered lanes) or HA antibody 12CA5 (even numbered lanes) and blotted with the same HA and myc antibodies. Wild type GRB2 or molecules having 2 intact SH3 domains (E89K, S9ON, GRB3.3) did bind to full length GA5Ptase (closed circles) but not shorter GA5Ptase proteins. Mutations that disrupt binding of either SH3 domain (P49L, G203R) markedly reduced (shaded triangle) or eliminated (open triangle) full length GA5Ptase binding. This illustrates that GRB2 associates with GA5Ptase through both of its SH3 domains. Example-4

Activation of Serum Response Element upon Co-expression with Ras and GRB2

NIH 3T3 cells were transiently transfected with constructs encoding GRB2, GA5Ptase, c-Ras, GRB2/c-Ras, GA5Ptase/c-Ras, GA5Ptase/GRB2 and GA5Ptase/c-Ras/GRB2, as listed in FIG. 5A-D, and the luciferase indicator plasmid p2FTL. This plasmid contains two copies of the c-fos serum response element (SRE) (−357 to −276) and the herpes simplex virus (HSV) thymidine kinase (TK) gene promoter (−200 to +70) driving the firefly luciferase gene. After growth for two days in serum depleted media, the cells were harvested and endogenous luciferase activity was measured in relative light units. Each value is the average of triplicate transfections, error bars represent standard error of the mean. Point mutations in GRB2 are the same as those indicated above.

Figure 5B:
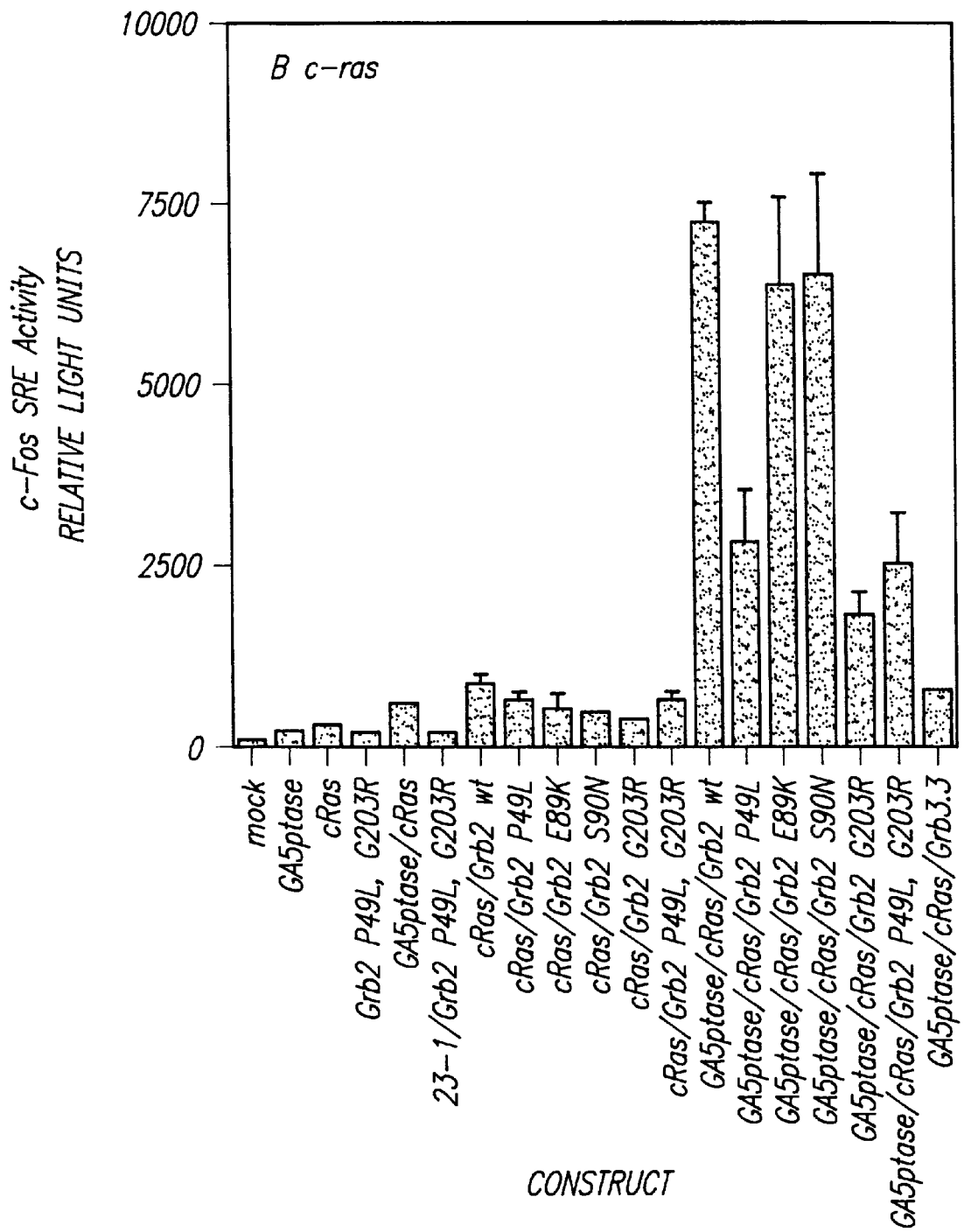
FIG. 5B shows SRE activation when co-expressed as indicated with GA5Ptase, c-Ras and the various GRB2 point mutations used in the Cos7 co-immunoprecipitation experiments shown in FIG. 4.
Figure 5C:
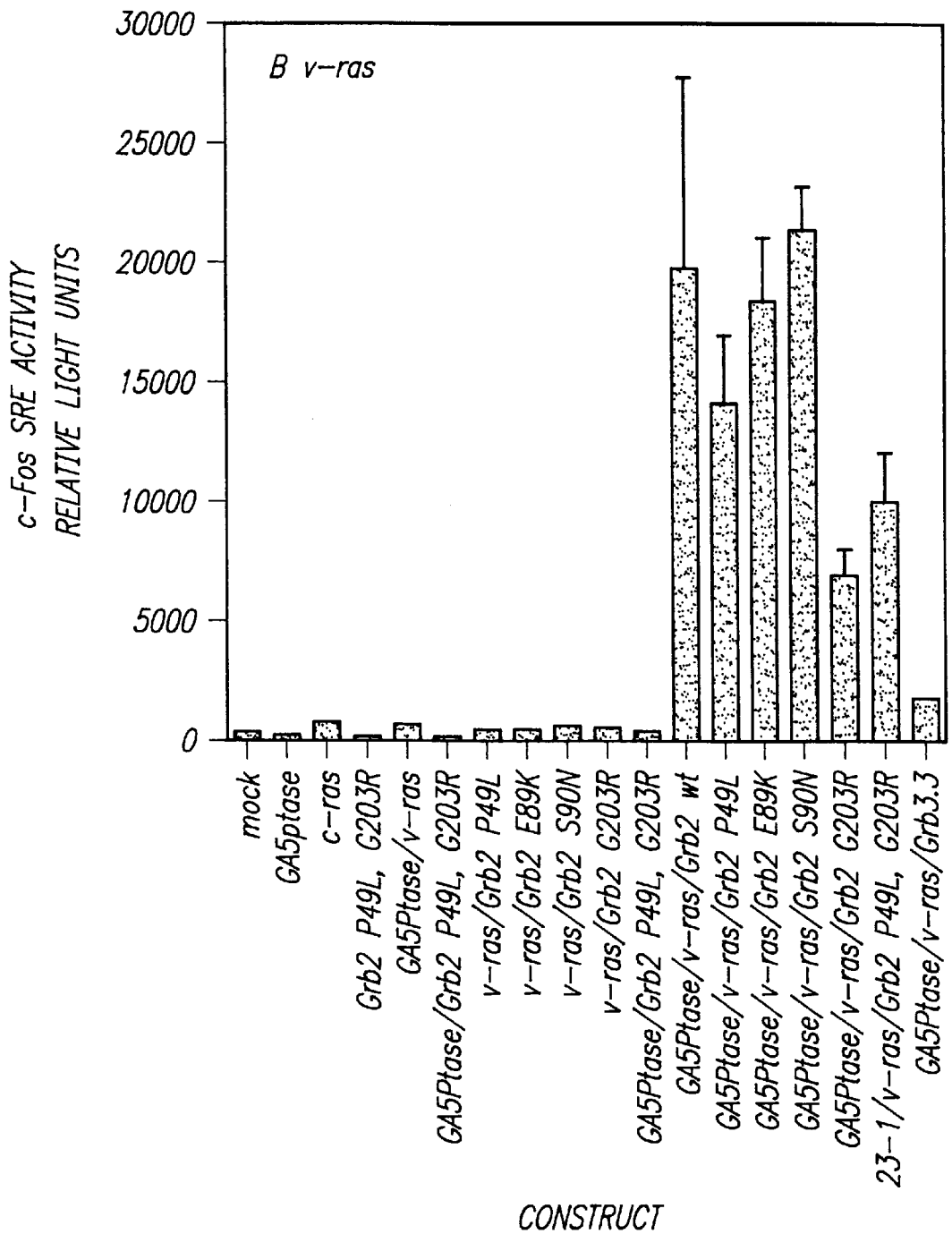
FIG. 5C shows SRE activation when co-expressed as indicated with GA5Ptase, v-Ras and GrbRB2 point mutations.
Figure 5D:
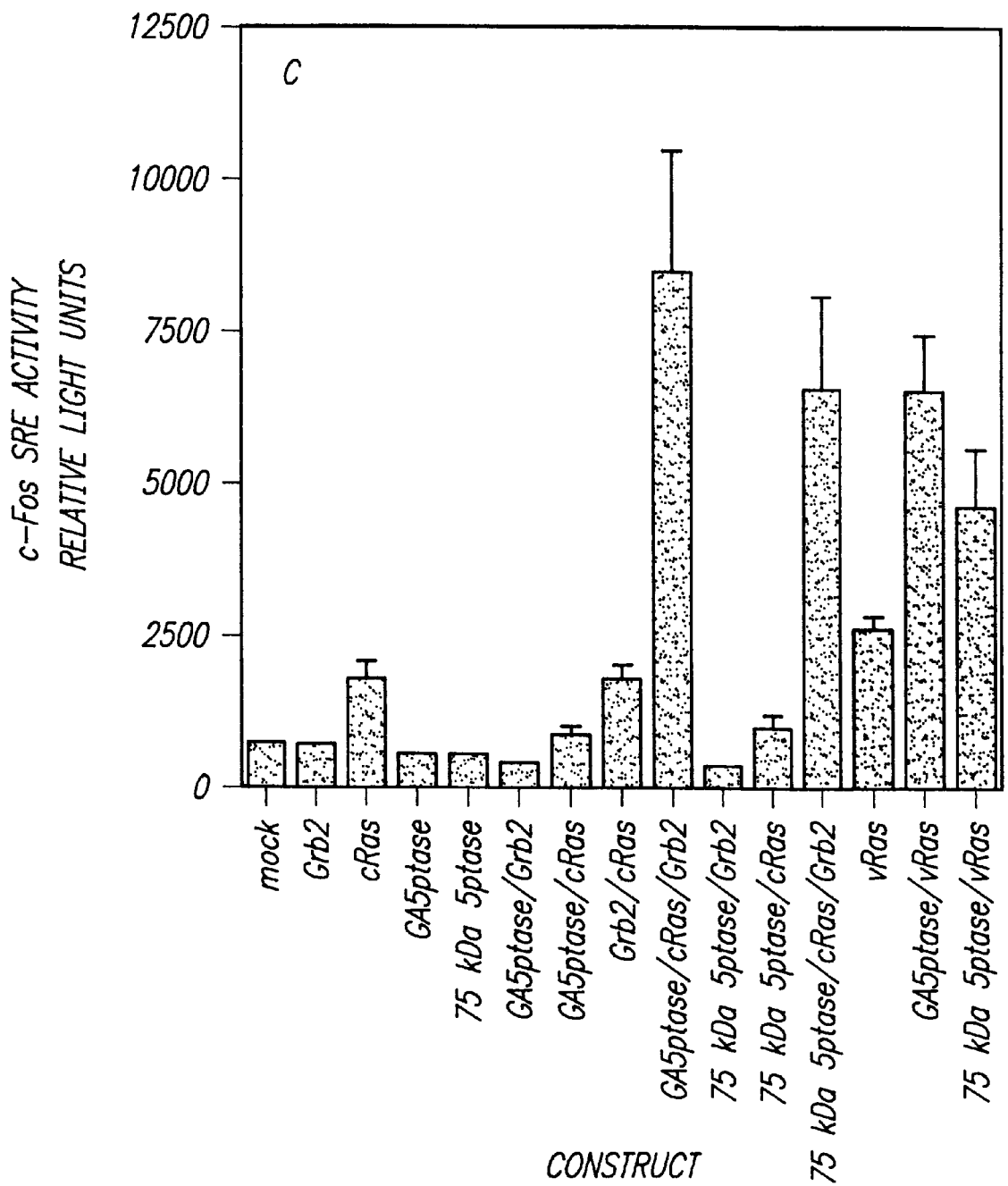
FIG. 5D shows a comparison of SRE activation when co-expressed with GA5Ptase versus platelet inositol polyphosphate 5-phosphatase type-II ("5Ptase II").

Substantial synergistic activation of the Fos promoter occurred when all three cDNAs were expressed. GRB2 mutants that reduce or eliminate the binding to GA5Ptase did not activate the Fos SRE as well as wild type (FIG. 5B and 5C), indicating the importance of the interaction between GA5Ptase and GRB2. Platelet inositol polyphosphate 5-phosphatase type II ("5Ptase II"), a 5ptase family member also possessing Ins(1,3,4,5)P$_4$ and PtdIns(3,4,5)P$_3$ hydrolyzing activity can substitute for GA5Ptase in its activation of cFos transcription (FIG. 5D). These results indicate the importance of GA5Ptase activity in Fos SRE activation.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

What is claimed is:

1. An isolated polypeptide, comprising an amino acid sequence of FIG. 10 (SEQ ID NO:2).

2. The isolated polypeptide of claim 1, wherein said polypeptide consists of the amino acid sequence shown in FIG. 10 (SEQ ID NO:2).

3. The isolated polypeptide of claim 1, wherein said polypeptide further comprises a heterologous protein fused to said amino acid sequence of FIG. 10 (SEQ ID NO:2).

4. A pharmaceutical composition, comprising an effective amount of the polypeptide of claim 1 in combination with a pharmaceutically acceptable carrier.

5. A kit for determining whether a test compound is an agonist or antagonist of GA5Ptase activity, comprising:
   a polypeptide, said polypeptide comprising a GA5Ptase polypeptide which comprises an amino acid sequence shown in FIG. 10 (SEQ ID NO:2);
   a GA5Ptase substrate; and
   instructions for assaying for the presence of said substrate and a product of GA5Ptase.

6. The kit of claim 5, wherein said GA5Ptase substrate is selected from the group consisting of $Ins(1,3,4,5)P_4$ and $PtdIns(3,4,5)P3$.

7. The kit of claim 5, wherein said GA5Ptase polypeptide and said GA5Ptase substrate are lyophilized, and further comprising a buffer solution for reconstituting said GA5Ptase polypeptide and said GA5Ptase substrate.

8. An isolated polypeptide, said polypeptide being immunologically cross-reactive with an antibody to a GA5Ptase protein which comprises an amino acid sequence shown in FIG. 10 (SEQ ID NO:2).

9. An isolated polypeptide, comprising an amino acid sequence of FIG. 10 (SEQ ID NO:2). wherein said polypeptide associates with GRB2.

10. The isolated polypeptide of claim 9, wherein the amino acid sequence shown in FIG. 10 (SEQ ID NO:2) binds a GRB2-SH3 domain.

11. The isolated polypeptide of claim 9, wherein said polypeptide is the amino acid sequence shown in FIG. 10 (SEQ ID NO:2) or a GRB2-associating fragment thereof.

12. The isolated polypeptide of claim 9, wherein said polypeptide further comprises a heterologous protein fused to said amino acid sequence of FIG. 10 (SEQ ID NO:2).

13. A pharmaceutical composition, comprising an effective amount of the polypeptide of claim 9 in combination with a pharmaceutically acceptable carrier.

14. A kit for determining whether a test compound is an agonist or antagonist of GA5Ptase activity, comprising:
   a polypeptide of claim 9;
   a GA5Ptase substrate; and
   instructions for assaying for the presence of said substrate and a product of GA5Ptase.

15. An isolated polypeptide, comprising an amino acid sequence of FIG. 10 (SEQ ID NO:2), wherein said polypeptide comprises an inositol polyphosphate 5-phosphatase activity such that said polypeptide hydrolyzes a 5-phosphate from $Ins(1,3,4,5)P4$ and $PtdIns(3,4,5)P3$, but not $Ins(1,4,5)P3$ or $PtdIns(4,5)P2$.

* * * * *